US009816991B2

(12) United States Patent
Dattwyler et al.

(10) Patent No.: US 9,816,991 B2
(45) Date of Patent: Nov. 14, 2017

(54) DIAGNOSTIC PEPTIDES FOR LYME DISEASE

(71) Applicant: Biopeptides Corp., New York, NY (US)

(72) Inventors: Raymond J. Dattwyler, East Setauket, NY (US); Paul M. Arnaboldi, Ozone Park, NY (US)

(73) Assignee: BIOPEPTIDES CORPORATION, East Setauket, NY (US)

( * ) Notice: Subject to any disclaimer, the term of this patent is extended or adjusted under 35 U.S.C. 154(b) by 0 days.

(21) Appl. No.: 14/376,409

(22) PCT Filed: Feb. 1, 2013

(86) PCT No.: PCT/US2013/024370
§ 371 (c)(1),
(2) Date: Aug. 1, 2014

(87) PCT Pub. No.: WO2013/116668
PCT Pub. Date: Aug. 8, 2013

(65) Prior Publication Data
US 2015/0017666 A1 Jan. 15, 2015

Related U.S. Application Data

(60) Provisional application No. 61/593,605, filed on Feb. 1, 2012, provisional application No. 61/680,583, filed on Aug. 7, 2012, provisional application No. 61/705,344, filed on Sep. 25, 2012.

(51) Int. Cl.
*A61K 39/02* (2006.01)
*A61K 39/00* (2006.01)
*A61K 39/38* (2006.01)
*G01N 33/569* (2006.01)
*C07K 14/20* (2006.01)

(52) U.S. Cl.
CPC ........ *G01N 33/56911* (2013.01); *A61K 39/02* (2013.01); *C07K 14/20* (2013.01); *G01N 2333/20* (2013.01)

(58) Field of Classification Search
CPC ...... A61K 38/10; A61K 38/16; A61K 38/164; A61K 39/00; A61K 39/02
USPC ................. 424/184.1, 185.1, 234.1
See application file for complete search history.

(56) References Cited

U.S. PATENT DOCUMENTS

| 5,656,451 A | * | 8/1997 | Flavell | C07K 14/20 435/320.1 |
| 6,054,296 A | * | 4/2000 | Bergstrom | C07K 16/1207 424/184.1 |
| 6,214,355 B1 | * | 4/2001 | Guo | C07K 14/20 424/234.1 |
| 6,486,130 B1 | * | 11/2002 | Livey | C07K 14/20 424/202.1 |
| 6,902,893 B1 | * | 6/2005 | Choi | C07K 14/20 435/6.16 |
| 7,060,281 B1 | * | 6/2006 | Dattwyler | A61K 39/0225 424/184.1 |
| 7,794,727 B2 | * | 9/2010 | Marconi | C07K 14/20 424/190.1 |
| 7,824,868 B2 | * | 11/2010 | Hook | C07K 14/78 435/7.1 |
| 2005/0147999 A1 | * | 7/2005 | Choi | C07K 14/20 435/6.16 |
| 2006/0194267 A1 | | 8/2006 | Vojdani | |
| 2009/0162875 A1 | | 6/2009 | Dattwyler et al. | |
| 2009/0214593 A1 | * | 8/2009 | Sallberg | A61K 39/12 424/227.1 |
| 2010/0136039 A1 | * | 6/2010 | Lundberg | C07K 7/08 424/190.1 |
| 2010/0278866 A1 | | 11/2010 | Barbour et al. | |

FOREIGN PATENT DOCUMENTS

| CA | 2708753 A1 | 12/2011 |
| WO | WO-1995/04145 A1 | 2/1995 |
| WO | WO-1997/27301 A1 | 7/1997 |
| WO | WO-1998/59071 A1 | 12/1998 |
| WO | WO-2002/077183 A2 | 10/2002 |
| WO | WO-2008/031133 A2 | 3/2008 |
| WO | WO-2009/022236 A2 | 2/2009 |
| WO | 2009106073 A2 | 9/2009 |
| WO | WO-2009/135118 A2 | 11/2009 |
| WO | WO-2011/112805 A2 | 9/2011 |

OTHER PUBLICATIONS

European Search Report corresponding to EP 13743514, and communication regarding European Search Report dated Aug. 21, 2015.
Adam S. Coleman, "BBK07 Immunodominant Peptides as Serodiagnostic Markers of Lyme Disease", Clinical and Vaccine Immunology, vol. 18, No. 3, Mar. 2011, pp. 406-413.
Peter D. Burbelo et al., "Rapid, Simple, Quantitative, and Highly Sensitive Antibody Detection for Lyme Disease", Clinical and Vaccine Immunology, vol. 17, No. 6, Jun. 2010, pp. 904-909.

* cited by examiner

*Primary Examiner* — Rodney P Swartz
(74) *Attorney, Agent, or Firm* — Millen, White, Zelano, Branigan, P.C.

(57) ABSTRACT

The present invention relates, e.g., to a composition comprising peptides represented by SEQ ID NO:1-SEQ ID NO:28 and/or SEQ ID NO:41-SEQ ID NO:47, or active variants thereof, wherein the peptides or active variants can bind specifically to an antibody induced by a causative agent of Lyme disease (a pathogenic *Borrelia*), e.g. in a sample from a subject having Lyme disease. Compositions of the invention may comprise multiple peptides, from multiple proteins. Diagnostic kits comprising the peptides are described, as are diagnostic assays using the peptides.

43 Claims, 15 Drawing Sheets

```
Strain
(OspC Type)          OspC 1                        OspC 30              PepC10
    B31 (A)     MTLFLFISCNNSGKDGNTSA---AKEAILKTNGT-KTKG---PVVAESPKKP
   PBre (B)     MTLFLFISCNNSGKDGNTSA---AKKAILKANAAGKDKG---PVVAESPKKP
    OC3 (C)    ·MTLFLFISCNNSGKDGNASA---AKEAILKTNGT-KDKG---PVV-------
 CA-11.2A (D)   MTLFLFISCNNSGKDGNTSA---AKKAILKTHNA-KDKG---PVVAESPKKP
    N40 (E)     MTLFLFISCNNSGKDGNASA---AQRAILKKHAN-KDKG---PIVAESPKKP
 B. pacificus (F) MTLFLFISCNNSGKDGNTSA---AKAAILKTNGT-NDKG---PVVAESPKKP
    OC8 (G)     MTLFLFISCNNSGKDGNAST---AKRAILKTHGH-EDKG--------------
   LDS79 (H)   ·----------NNSGKDGNASA---AKKAILKTHGN-TDKG---PVVAESPKKP
    OC9 (H)    ·MTLFLFISCNNSGKDGNTSA---AKKAILKTHGN-TDKG--------------
   HB19 (I)     MTLFLFISCNNSGKDGNTSA---AKKAILKTNND-KTKG---PVVAESPKKP
    MIL (J)    ·-TLFLFISCNNSGKDGNTSA---AKKAILKTNQA-NDKG--------------
   OC10 (J)    ·MTLFLFISCNNSGKDGNTSA---AKKAILKTNQA-NDKG--------------
   OC12 (K)   ··MTLFLFISCNNSGKDGNTSA---AKKAILITDAA-KDKG---PIV-------
   LDP74 (K)   ·----------NNSGKDGNTSA---AKKAILITDAA-KDKG---PIVAESPKKP
    T255 (L)    MTLFLFISCNNSGKDGNASV---AKKAILKTHND-ITKG---PVVAESPKKP
    8356 (M)   ·MTLFLFISCNNSGKDGNTSA---AKAAILKTNGT-KDKG---PVVAESPKKP
    2591 (M)   ·MTLFLFISCNNSGKDGNTSA---AKAAILKTNGT-KDKG---PVVAENPKKP
   26815 (N)   ·----------CNNSGKDGNAST---AKKAILRTNAI-KDKG---PVVAETPKKP
     CS5 (U)    MTLFLFISCNNSGKDGNASA---AKDAILKTNPT-KTKG---LLWPESP----
 Consensus      MTLFLFISCNNSGKDGNTSA---AKKAILKTNGX-KDKG---PVVAESPKKP
```

FIG. 6

|                      |                   |                   |                   |       |
|----------------------|-------------------|-------------------|-------------------|-------|
| OppA (191-225)       | YGQNWTSPEN        | MVTSGPFKLK        | ERIPNEKYVF        | EKNNK 35 |
| Borrelia burgdorferi | YGQNWTSPEN        | MVTSGPFKLK        | ERIPNEKYVF        | EKNNK 35 |
| Borrelia burgdorferi 80a | YGQNWTSPEN    | MVTSGPFKLK        | ERIPNEKYVF        | EKNNK 35 |
| Borrelia burgdorferi 156a | YGQRWTDPEN   | MVVSGPFKLK        | SRVLNEKVVL        | EKNNK 35 |
| Borrelia garinii PBi | YGQSWTSPEN        | IVTSGPFKLK        | ERIPNEKYVV        | EKNNK 35 |
| Borrelia garinii Far04 | YGQSWTSPEN      | MVTSGPFKLK        | ERIPNEKYVV        | EKNDK 35 |
| Borrelia garinii BgVir | YGQEWTNPEN      | MVVSGPFKLK        | SRVLNEKVVL        | EKNDK 35 |
| Borrelia afzelii PKo | HGQEWTNPEN        | MVVSGPFKLK        | SRVLNEKIIL        | EKNNK 35 |
| Borrelia afzelii ACA-1 | YGENWTNPEN      | IVVSGAYKLK        | ERSINDKIVI        | EKNEK 35 |
| Consensus            | YGQNWTSPEN        | MVTSGPFKLK        | ERIPNEKYVX        | EKNNK |

FIG. 9

|  |  |  | 20 |
|---|---|---|---|
| OppA (381-400) | KKICEFIQNQ | WKKNLNIDVE | 20 |
| Borrelia burgdorferi 80a | KKICEFIQNQ | WKKNLNIDVE | 20 |
| Borrelia burgdorferi ZS7 | RKIAEFIQNQ | WKKNLNINVQ | 20 |
| Borrelia burgdorferi WI91-23 | RKIAEFIQNQ | WKKNLNINVQ | 20 |
| Borrelia garinii BgVir | KKICEFIQNQ | WKKNLNIDVE | 20 |
| Borrelia garinii PBi | KKICEFIQNQ | WKKILNIDVE | 20 |
| Borrelia garinii Far04 | RKIAEFIQNQ | WKKNLNINVQ | 20 |
| Borrelia afzelii PKo | KKICEFIQNQ | WKKILNIDVE | 20 |
| Borrelia afzelii ACA-1 | RKIAEFIQNQ | WKKNLNINVQ | 20 |
| Consensus | KKICEFIQNQ | WKKNLNIDVE | |

FIG. 10

DIAGNOSTIC PEPTIDES FOR LYME DISEASE

This application is a National Stage of International Application No. PCT/US2013/024370, filed Feb. 1, 2013, which claims the benefit of the filing dates of U.S. provisional applications No. 61/593,605, filed Feb. 1, 2012; No. 61/680,583, filed Aug. 7, 2012; and No. 61/705,344, filed Sep. 25, 2012; each of which is incorporated by reference herein in its entirety.

This application was made with U.S. government support (NIH-NIAID, grant number 1R44 AI07092). Therefore, the government has certain rights in the invention.

SEQUENCE LISTING

The instant patent application contains a Sequence Listing which has been submitted via EFS-Web and is hereby incorporated by reference in its entirety. Said ASCII copy, created on Mar. 11, 2013, is named 64557-343983_SL.txt and is 96,530 bytes in size.

FIELD OF THE INVENTION

This invention relates, e.g., to agents and methods for diagnosing Lyme disease.

BACKGROUND INFORMATION

Lyme disease (sometimes referred to herein as LD or Lyme borreliosis) is a common vector-borne disease that is a significant public health concern. The disease is transmitted by the bite of various species of *Ixodes* ticks carrying the etiologic agent, a pathogenic *Borrelia* bacterium (a spirochete). Organisms of the *Borrelia burgdorferi* sensu lato group belong to the family Spirochaetaceae, genus *Borrelia*. There are at least 11 species in the *B. burgdorferi* complex and an unknown but large number of substrains. At least three genospecies of the *Borrelia burgdorferi* sensu lato group have been identified as pathogens: *B. burgdorferi* sensu stricto, *B. afzelii*, and *B. garinii*. In addition, other species of *Borrelia* have been implicated as being causative pathogenic agents. The major reservoir of the infection in the United States is the white footed mouse, and the infection can be transmitted to many mammalian species, including various other forms of wildlife, e.g. Eastern chipmunks, and dogs, cats, and humans.

Clinically, Lyme disease is a progressive disease with a wide array of manifestations. Early diagnosis and treatment is critical to prevent progression. Late disseminated infection can be associated with permanent damage to the nervous and musculoskeletal systems. Unlike most bacterial diseases that can be defined microbiologically by direct observation or culture of the pathogen, *B. burgdorferi* is difficult to culture or observe in clinical samples. Therefore, Lyme disease is defined indirectly. Erythema migrans (EM) is the classic marker for this infection at early stages. However, not all patients infected with pathogenic *Borrelia* develop EM. In the absence of EM, the current basis for diagnosis is the demonstration of an antibody response against a pathogenic *Borrelia* in an appropriate clinical setting.

Unfortunately, current serologic assays for such antibodies suffer from both low sensitivity and specificity, especially in early disease. The U.S. Centers for Disease Control and Prevention (CDC) currently recommends that in order for a patient to be considered seropositive, two assays must be positive: a first tier assay, such as an ELISA, IFA or lateral flow assay, followed by a second tier assay, such as a western blot. This approach is expensive and can delay diagnosis for a week or more, but it is necessary because of the poor specificity of the most commonly used first tier assays. There is a need for a simple, sensitive and specific diagnostic method for the detection of Lyme disease, e.g. at early times after infection.

DESCRIPTION OF THE DRAWINGS

FIG. 6 shows amino acid sequence alignment of different OspC types depicting the regions corresponding to OspC1, OspC 30, and PepC10. Sequences were aligned using CLC workbench and were trimmed to show only the regions corresponding to the peptides of interest. In several instances complete sequences for the OspC types containing all three peptides were not available. When possible multiple partial sequences for that OspC type were aligned, depicting the presence or absence of a particular peptide sequence. *=partial sequence. **=partial sequence used for epitope mapping. The sequence identifiers of the peptides, reading from the top to the bottom of the figure, are, respectively in order of appearance, SEQ ID NOS 217-236.

FIG. 9 shows that OppA2 linear epitopes are conserved among pathogenic *Borrelia* species. The sequences, shown from the top to the bottom of the figure, are represented, respectively in order of appearance, by SEQ ID NOS 11 and 237-245.

FIG. 10 shows that OppA2 linear epitopes are conserved among pathogenic *Borrelia* species. The sequences, shown from the top to the bottom of the figure, are represented by SEQ ID NOS 45 and 246-254, respectively, in order of appearance.

DESCRIPTION

Figure 1A:
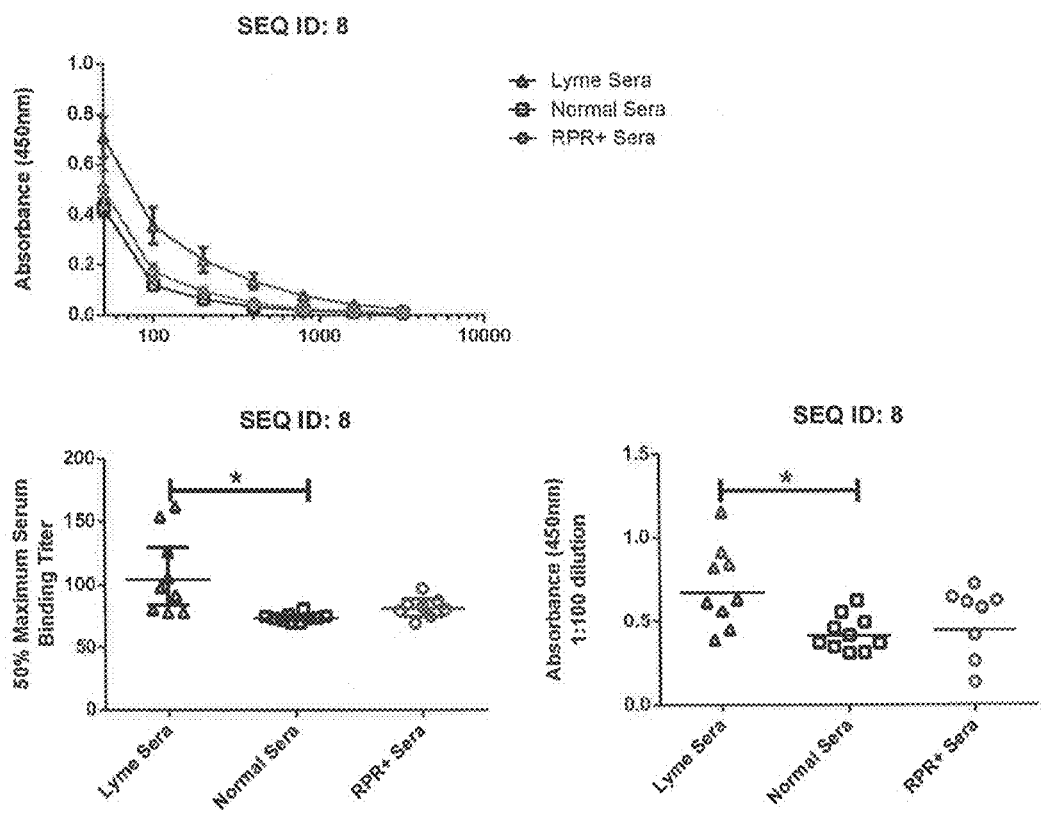
FIG. 1A shows representative data demonstrating enhanced binding of serum from Lyme disease patients to peptide SEQ ID NO:8 compared to serum from healthy individuals (normal sera) or patients with Syphilis (RPR+ sera). The upper panel demonstrates serum binding at several different dilutions. The lower left panel compares the binding of antibody from individual patient sera at the 50% maximal serum binding titer, which is the serum dilution at which the absorbance of a particular binding curve (as depicted in the upper panel) reaches 50% of the maximal absorbance recorded for that curve. The lower right panel compares the absorbance values generated by binding of antibody from individual patient sera at a single dilution (1:100). Data were generated using standard ELISA techniques and a goat anti-human IgG and IgM secondary antibody to detect serum antibody binding.
Figure 1B:
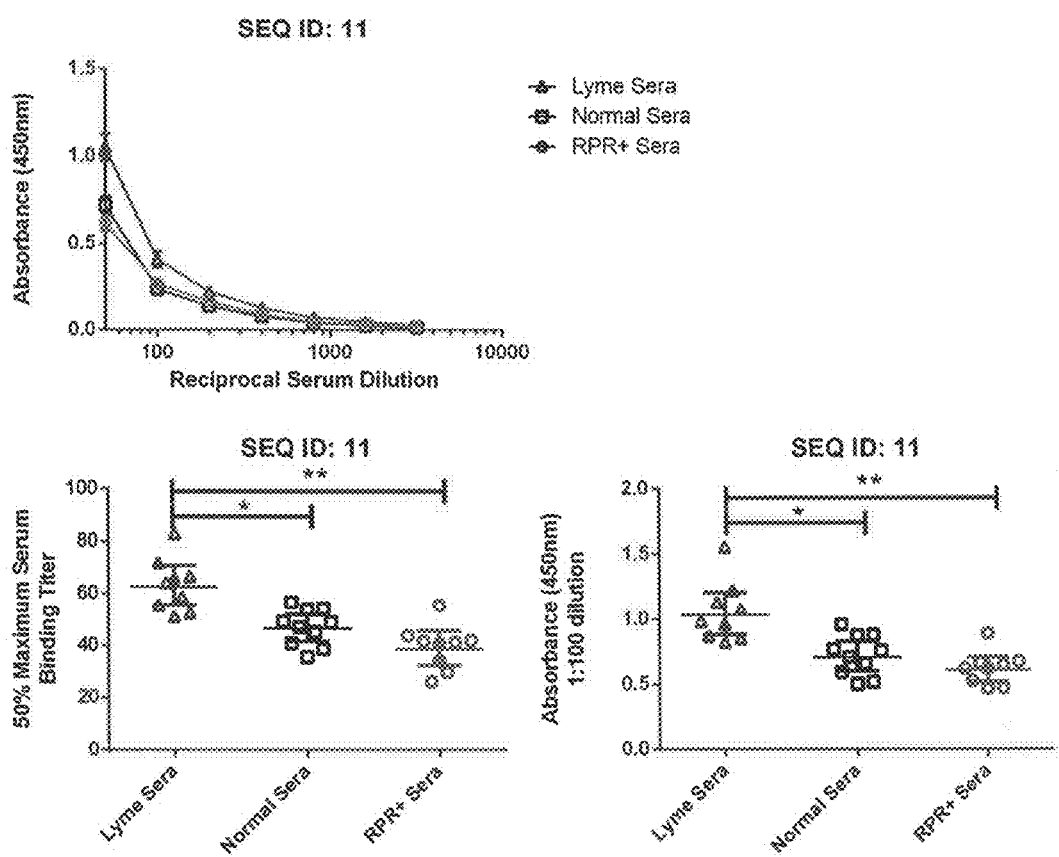
FIG. 1B shows representative data demonstrating enhanced binding of serum from Lyme disease patients to peptide SEQ ID NO:11 compared to serum from healthy individuals (normal sera) or patients with Syphilis (RPR+ sera). The upper panel demonstrates mean serum antibody binding at several different dilutions (n=10 patients/group). The lower left panel compares the binding of antibody from individual patient sera at the 50% maximal serum binding titer, which is the serum dilution at which the absorbance of a particular binding curve (as depicted in the upper panel) reaches 50% of the maximal absorbance recorded for that curve. The lower right panel compares the absorbance values generated by binding of antibody from individual patient sera at a single dilution (1:100). Data were generated using standard ELISA techniques and a goat anti-human IgG and IgM secondary antibody to detect serum antibody binding. Similar data have been generated for all peptides discussed in this application.

The present inventors, by using a finely detailed epitope mapping strategy, have identified at least 22 peptides that can specifically and efficiently recognize antibodies to a pathogenic *Borrelia* which develop in a subject infected with a pathogen from the *Borrelia burgdorferi* sensu lato group. The peptides identified by the inventors were derived from the North American pathogenic species of *B. burgdorferi*, *B. burgdorferi* sensu stricto. The peptides which are discussed in the present application are represented by SEQ ID NOs: 1-28 and 41-47, as shown in Table 1.

TABLE 1

| Protein name/ position in the protein | Sequence |
| --- | --- |
| p66 (516-530) | FEDAMKLGLALYLDY (SEQ ID NO: 1) |
| p66 (576-590) | LIRFTTISLGWDSNN (SEQ ID NO: 2) |
| RecA (231-245) | KFYSSLRLEVRKIEQ (SEQ ID NO: 3) |
| LA-7 (91-110) | IPSKENAKLIVYFYDNVYAG (SEQ ID NO: 4) |
| LA-7 (91-105) | IPSKENAKLIVYFYD (SEQ ID NO: 5) |
| LA-7 (96-110) | NAKLIVYFYDNVYAG (SEQ ID NO: 6) |
| OspC-type A (66-85) | KNEGLKEKIDAAKKCSETFT (SEQ ID NO: 7) |
| OspC-type K (11-30) | MTLFLFISCNNSGKDGNTSA (SEQ ID NO: 8) |
| OspC-type K (146-160) | AKKAILITDAAKDKG (SEQ ID NO: 9) |

TABLE 1-continued

| Protein name/ position in the protein | Sequence |
|---|---|
| OppA (11-25) | IFFLTFLCCNNKERK (SEQ ID NO: 10) |
| OppA (191- 225) | YGQNWTSPENMVTSGPFKLKERIPNEKYVFEKNNK (SEQ ID NO: 11) |
| OppA (276-290) | SDYYSSAVNAIYFYA (SEQ ID NO: 12) |
| OppA (286-300) | IYFYAFNTHIKPLDN (SEQ ID NO: 13) |
| OppA (276-300) | SDYYSSAVNAIYFYAFNTHIKPLDN (SEQ ID NO: 14) |
| Bbg33 (176-190) | DMFSLEQRLEIKLEA (SEQ ID NO: 15) |
| DbpB (11-25) | LVACSIGLVERTNAA (SEQ ID NO: 16) |
| BmpA (56-70) | KEEFKIELVLKESSS (SEQ ID NO: 17) |
| FLi1B (46-60) | IVSYFVSKMVVSQSG (SEQ ID NO: 18) |
| FLi1B (91-110) | NTLDVPPKTFVVKLALGYAE (SEQ ID NO: 19) |
| FLi1B (16-30) | VSRKGGLLPDIIIKI (SEQ ID NO: 20) |
| FLi1B (126-140) | LKDIIREYFSQRTGQ (SEQ ID NO: 21) |
| Bbk32 (16-30) | GFISCDLFIRYEMKE (SEQ ID NO: 22) |
| Bbk32 (51-80) | KKPMNKKGKGKIARKKGKSKVSRKEPYIHS (SEQ ID NO: 23) |
| P35 (101-115) | DTGSERSIRYRRRVY (SEQ ID NO: 24) |
| ErpP (51-65) | KIEFSKFTVKIKNKD (SEQ ID NO: 25) |
| CRASP 2 (206-225) | NSRSRYNNFYKKEADFLGAA (SEQ ID NO: 26) |
| OspF (86-105) | INKLEAKKTSLKTYSEYEEQ (SEQ ID NO: 27) |
| OspF (216-230) | IDDSIKKIDEELKNT (SEQ ID NO: 28) |
| DbpA (6-20) | NKTFNNLLKLTILVN (SEQ ID NO: 41) |
| DbpA (6-30) | NKTFNNLLKLTILVNLLISCGLTGA (SEQ ID NO: 42) |
| DbpA (16-30) | TILVNLLISCGLTGA (SEQ ID NO: 43) |
| DbpA (76-90) | PFILEAKVRATTVAE (SEQ ID NO: 44) |
| OppA (381-400) | KKICEFIQNQWKKNLNIDVE (SEQ ID NO: 45) |
| OppA (286-310) | IYFYAFNTHIKPLDNVKIRKALTLA (SEQ ID NO: 46) |
| OppA (356-375) | LAEAGYPNGNGFPILKLKYN (SEQ ID NO: 47) |

The numbering of the amino acid residues of the peptides corresponds to the numbering of the amino acids in the corresponding full-length proteins.

One aspect of the invention is a composition comprising 10 (or fewer) of the following 10 peptides, or active variants thereof, in which one or more of the amino acids is substituted with an amino acid replacement, wherein the peptide or active variant can bind specifically to an antibody against a pathogenic Borrelia:

YGQNWTSPENMVTSGPFKLKERIPNEKYVFEKNNK (SEQ ID NO: 11)

KKPMNKKGKGKIARKKGKSKVSRKEPYIHS (SEQ ID NO: 23)

MTLFLFISCNNSGKDGNTSA (SEQ ID NO: 8)

KFYSSLRLEVRKIEQ (SEQ ID NO: 3)

KEEFKIELVLKESSS (SEQ ID NO: 17)

INKLEAKKTSLKTYSEYEEQ (SEQ ID NO: 27)

TILVNLLISCGLTGA (SEQ ID NO: 43)

KIEFSKFTVKIKNKD (SEQ ID NO: 25)

```
                            (SEQ ID NO: 24)
DTGSERSIRYRRRVY (SEQ ID NO: 28)
IDDSIKKIDEELKNT.
```

This group of peptides is sometimes referred to herein as Group I peptides. In one embodiment of this aspect of the invention, the composition comprises the 10 peptides of Group I, but not the active variants. In some embodiments, the composition comprises any 9, any 8, any 7, any 6, any 5, any 4, any 3, any 2, or any 1 of the 10 peptides or active variants thereof. In some embodiments, the composition comprises the peptide or active variant of SEQ ID NO: 11; or it comprises the peptide or active variant of SEQ ID NO: 23; or it comprises the peptide or active variant of SEQ ID NO: 8; or it comprises the peptide or active variant of SEQ ID NO:3; or it comprises the peptides or active variants of SEQ ID NOs:11 and 23; or it comprises the peptides or active variants of SEQ ID NOs:11 and 8; or it comprises the peptides or active variants of SEQ ID NOs:8 and 23. In some embodiments, the peptides in a composition of this aspect of the invention are from 3 or more, or 4 or more, or 5 or more, or 6 or more, or 7 or more different proteins from *Borellia burgdorferi* sensu lato. The proteins can be, e.g., OppA, Bbk32, OspC-typeK, RecA, BmpA, OspF, DbpA, ErpP, p35, OspF, CRASP 2, FlilB, p66, OspC-typeA, or DdpB. For example, in one embodiment of the invention, the composition comprises at least 7 or at least 8 of the peptides or active variants of Group I, wherein the peptide of SEQ ID NO:11, or the peptide of SEQ ID NO:23, or both of these peptides, is present in the composition. The composition can comprise peptides from at least 6 different proteins. Other combinations of the peptides of Group I are also encompassed by this aspect of the present invention.

Another aspect of the invention is a composition comprising one or more (e.g., at least 2, at least 3, at least 4, at least 5, at least 6, at least 7, at least 8, or at least 9) of the peptides of Group I, or active variants thereof, in which one or more of the amino acids is substituted with an amino acid replacement, wherein the peptide or active variant can bind specifically to an antibody against a pathogenic *Borrelia*. For example, in embodiments of this aspect of the invention, a composition comprises a peptide or active variant of any one of SEQ ID NOs: 11, 23, 8, 3, 17, 27, 43, 25, 24, 28, or 26. In other embodiments, the composition further comprises, in addition to one of the indicated peptides of Group I, a peptide or active variant of SEQ ID NO:11, or a peptide or active variant of SEQ ID NO:23, or a peptide or active variant of SEQ ID NO:8, or peptide or active variant of SEQ ID NO:3; or peptides or active variants of both SEQ ID NO:11 and SEQ ID NO:23; or peptides or active variants of both SEQ ID NO:11 and SEQ ID NO:8, or peptides or active variants of both SEQ ID NO:8 and SEQ ID NO:23. In some embodiments, the peptides in a composition of this aspect of the invention are from 3 or more, or 4 or more, or 5 or more, or 6 or more, or 7 or more, or 8 or more, different proteins from *Borellia burgdorferi* sensu lato. The proteins can be, e.g., OppA, Bbk32, OspC-typeK, RecA, BmpA, OspF, DbpA, ErpP, p35, OspF, CRASP 2, FlilB, p66, OspC-typeA, or DdpB. Other combinations of the peptides of Group I are also encompassed by this aspect of the present invention.

Compositions of either of the aspects of the invention discussed above can further comprise one or more of the following 12 peptides, or active variants thereof, in which one or more of the amino acids is substituted with an amino acid replacement, wherein the peptide or variant can bind specifically to an antibody against a pathogenic *Borrelia*:

```
                            (SEQ ID NO: 26)
NSRSRYNNFYKKEADFLGAA (SEQ ID NO: 22)
GFISCDLFIRYEMKE (SEQ ID NO: 19)
NTLDVPPKTFVVKLALGYAE (SEQ ID NO: 45)
KKICEFIQNQWKKNLNIDVE (SEQ ID NO: 20)
VSRKGGLLPDIIIKI (SEQ ID NO: 41)
NKTFNNLLKLTILVN (SEQ ID NO: 2)
LIRFTTISLGWDSNN (SEQ ID NO: 1)
FEDAMKLGLALYLDY (SEQ ID NO: 13)
IYFYAFNTHIKPLDN (SEQ ID NO: 9)
AKKAILITDAAKDKG (SEQ ID NO: 7)
KNEGLKEKIDAAKKCSETFT (SEQ ID NO: 16)
LVACSIGLVERTNAA.
```

This group of peptides is sometimes referred to herein as Group II peptides. For example, a composition can comprise 2, 3, 4, 5, 6, 7, 8, 9, 10, 11 or 12 of the peptides or active variants thereof of Group II, in any combination which is desirable.

Another aspect of the invention is a composition comprising 12 (or fewer) of the peptides of Group II, or active variants thereof, in which one or more of the amino acids is substituted with an amino acid replacement, wherein the peptide or variant can bind specifically to an antibody against a pathogenic *Borrelia*.

In one embodiment of the invention, a composition comprises from about 4 to about 15 (e.g., from about 5 to about 12) of the peptides or active variants thereof of Group I and Group II combined, and the peptides come from at least 5 or 6 different proteins. Additional peptides or active variants thereof can also be present in a composition of the invention. As used herein, "about" means plus or minus 10% of the value.

One or more of any of the peptides noted above can further comprise an N-terminal cysteine residue; and/or it can further comprise 1-3 additional and/or 1-3 fewer amino acids at one or both ends of the peptide.

A composition of the invention discussed above can further comprise one or more additional peptides which are specific for antibodies against the same or different proteins of the same or a different pathogenic *Borrelia*. For example, one aspect of the invention is a composition comprising, in addition to the peptides in the compositions discussed above, a peptide which comprises an epitope from *Borrelia* flagellin p41 (e.g., the peptide having the sequence VQEGVQQEGAQQP (SEQ ID NO:39)), and/or an epitope from *Borrelia* OspC (e.g., the peptide having the sequence PVVAESPKKP (SEQ ID NO:40)). Alternatively, or in addition, a composition of the invention as discussed above can further comprise a peptide from the VLsE (region IR6) *Borrelia* protein (e.g. the 26 amino acid peptide CMKKD-DQIAAA MVLRGMAKDGQFALK (SEQ ID NO 48), which is currently in commercial use), or a shorter, 17 amino acid peptide from this region, MKKNDQI(V or G)AAIAL-RGVA (SEQ ID NO49), or active variants thereof. The 17 amino acid peptide and active variants thereof are described in detail in U.S. Pat. No. 7,887,815, which is incorporated by reference herein.

Another aspect of the invention is an isolated peptide comprising the sequence of any one of SEQ ID NOs: 11, 23, 8, 3, 17, 27, 43, 25, 24, 28, or 26, or any one of SEQ ID NOs: 26, 22, 19, 45, 20, 41, 2, 1, 13, 9, 7 or 16, or an active variant thereof in which one or more of the amino acids is substituted with an amino acid replacement, wherein the peptide or variant can bind specifically to an antibody against a pathogenic *Borrelia*. The isolated peptide can further comprise an N-terminal cysteine residue; and/or it can further comprise 1-3 additional and/or 1-3 fewer amino acids at one or both ends of the peptide.

Another aspect of the invention is an isolated compound comprising such an isolated peptide, linked to at least one further moiety, via a terminal amino acid linker or a chemical coupling agent. The further moiety can be, e.g., a second peptide that specifically recognizes an antibody against a pathogenic *Borrelia*, wherein the peptide and the second peptide are covalently linked. In embodiments of the invention, the peptide and the second peptide are separated from one another by a spacer of 1-5 Glycine or Alanine residues. The second peptide can be any of the peptides of Group I or Group II, or an active variant thereof, or a peptide which comprises an epitope from *Borrelia* flagellin p41 (e.g., which has the sequence VQEGVQQEGAQQP (SEQ ID NO:39)) or from *Borrelia* OspC (e.g., which has the sequence PVVAESPKKP (SEQ ID NO:40)). Any of these isolated compounds can be included in a composition of the invention.

Another aspect of the invention is a diagnostic reagent comprising one or more of the isolated peptides, isolated compounds, or compositions described herein, and a system for detecting the peptide(s) and/or a substrate for immobilizing the peptide(s).

Another aspect of the invention is a kit for diagnosing Lyme borreliosis, comprising one or more isolated peptides, isolated compounds, or compositions of the invention, and a system for detecting the peptide(s) bound to an antibody to a pathogenic *Borrelia* protein and/or a substrate (e.g. a surface in a well or a bead, such as a polystyrene bead, for immobilizing the peptide(s). The peptides in a kit of the invention may be distributed in one or more containers.

Another aspect of the invention is a method diagnosing Lyme disease in a subject, comprising contacting a sample from a subject suspected of having antibodies against a causative agent of Lyme disease with an isolated peptide, isolated compound, or composition of the invention, under conditions effective for the formation of a peptide-antibody complex, and detecting the presence of the peptide-antibody complex. In embodiments of the invention, the peptide-antibody complex is detected by adding a binding partner which is labeled, or which can be labeled with a signal generating reagent. The binding partner can be, e.g., an antibody attached to an enzyme, and a signal is generated when the enzyme reacts with a suitable substrate. In another embodiment, the detecting is performed with an ELISA assay. In another embodiment, the detecting is performed with a Luminex bead based assay; by microarray analysis, or lateral flow methods. The subject may be a mammal, such as, e.g., a cat, a dog, or a human.

Active variants of the peptides represented by SEQ ID NOs:1-28 and 41-47 are also included in the invention. Such active variants include, e.g., peptides in which one or more of certain amino acids is substituted with a conservative or non-conservative amino acid replacement.

The inventors have aligned and compared the sequences of the 35 peptides indicated in Table 1 from a wide variety of individual subspecies or isolates of *Borrelia burgdorferi* sensu lato, which includes all of the pathogenic *Borellia* genospecies that can cause Lyme disease, including *B. burgdorferi* sensu stricto, *B. garinii* and *B. afzelli* as well as a few other minor ones that can cause disease in limited geographical regions. Each genospecies of the bacteria has multiple strains. Thus, each BLAST alignment may have dozens of different variants among the different strains in each genospecies. Using such alignments, a skilled worker can readily determine which amino acid residues are conserved and may be important for the ability to bind specifically and efficiently to antibodies to pathogenic *Borrelia* which develop in a subject infected with a pathogen from *Borrelia*; and which amino acids differ between peptides from these strains, but the peptides appear to retain at least some of the binding specificity and efficacy, and thus these amino acids appear to be nonessential (or at least not very important) for this activity.

Below are consensus sequences for some of the peptides of the invention, derived in part on the basis of such alignments, in part on confirmatory ELISA analysis as described elsewhere herein, and in part on studies with in vitro generated mutant peptides. Consensus sequences derived from two algorithms are shown. The analysis also indicates active variants of the peptides; the active variants can bind specifically to an antibody against a pathogenic *Borrelia*. In the active variants, one or more of the indicated amino acids can be substituted with an amino acid replacement, such as a conservative amino acid replacement. Also shown are some particular active variants for each of the peptides.

1. KEEFKIELVLKESSS (BmpA (56-70); SEQ ID NO:17).

In active variants of this peptide, one or more of amino acids E2, F4, K5, I6, and/or S15 can be substituted with an amino acid replacement; or amino acids E2, E3, F4, K5, I6, L8, and/or S15 can be substituted.

```
Consensus sequence:
                                             (SEQ ID NO: 54)
K (E or A) E (F or R) (K or E) (I or F)

E L V L K E S S (S or T);

Particular active variants:
                                             (SEQ ID NO: 55)
KEEFKIELVLKESST;

(SEQ ID NO: 56)
KAERKIELVLKE---;

(SEQ ID NO: 57)
KEEFKFELVLKESST;

(SEQ ID NO: 58)
KEEFEIELVLKESST;

(SEQ ID NO: 59)
KAERKIELV(N)(L)LKE;

(SEQ ID NO: 60)
-EIFKIEKVL----,
```

2. YGQNWTSPENMVTSGPFKLKERIP-NEKYVFEKNNK (OppA (191-225); SEQ ID NO:11).

In active variants of this peptide, one or more of amino acids Y1, G2, Q3, N4, S7, M11, T13, P16, F17, E21, I23, P24, E26, Y28, V29, F30, and/or N34 can be substituted with an amino acid replacement.

```
Consensus sequence #1:
                                        (SEQ ID NO: 61)
(Y, H, or F) (G or K) (Q, G, E, or N) (N, K, S, R, or E) W T (S, N, or D) P E N (M or I) V (T or V) S G (P or A) (F or Y) K L K (E, K, S or R) R (I, S, L, or V) (P, L, or I) N (E or D) K (Y, V or I) (V or I) (F, V, L or I) E K N (N, D, or E) K.

Consensus sequence #2:
                                        (SEQ ID NO: 62)
Y1, G2, Q3, N4, S7, P8, M11, T13, P16, F17, E21,
I23, P24, E26, K27, Y28, V29, F30, N34, and/or K35

Particular active variants:
                                       (SEQ ID NO: 257)
YGQNWTNPENMVTSGPFKLKERIPNEKIVFEKNNK, (SEQ ID NO: 63)
YGENWTNPENIVVSGAYKLKERLINDKIVIENNEK, (SEQ ID NO: 64)
YGQEWTNPENMVVSGPFKLKSRVLNEKVVLEKNDK, (SEQ ID NO: 65)
YKGNWTNPENMVTSGPFKLKKRLPNEKIIFEKN--, (SEQ ID NO: 66)
HGQNWTNPENMVVSGPFKLKSRVLNEKIILEKNNK, (SEQ ID NO: 67)
YGQSWTNPENIVTSGPFKLKERIPNEKYVVEKNDK, (SEQ ID NO: 68)
YKGNWTSPENMVTSGPFKLKKRLPNEKIIFEKNER, (SEQ ID NO: 69)
YGQRWTDPENMVVSGPFKLKSRVLNEKVVLEKNNK, (SEQ ID NO: 70)
HGQEWTNPENMVVSGPFKLKSRVLNEKIILEKNNK, (SEQ ID NO: 71)
FGNKWTNPENMVTSGPFKLKRRILNEEISLEKNKK, (SEQ ID NO: 72)
FGNKWTSSENMVTSGPFKLKRRILNEEISLEKNEK,
```

3. MTLFLFISCNNSGKDGNTSA (OspC-type K (11-30); SEQ ID NO:8).

In active variants of this peptide, one or more of amino acids K14, G15, N17, T18, S19, and/or A20 can be substituted with an amino acid replacement, or one or more of amino acids F4, C9, N11, D15, G16, N17, T18, S19, and/or A20 can be substituted.

```
Consensus sequence #1:
                                        (SEQ ID NO: 73)
M T L F L F I S C N N S G (K or G) (D or G) G
(N or D) (T, A, or S) (S, A, or T) (A or S).

Consensus sequence #2:
                                        (SEQ ID NO: 74)
M T L (F, L, or Y) L F I S (C or S) N (N or T)
S G K (D or G) (G, V, or A) (N, D, T or S) (T,
A, or S) (S, A, or T) (A or T).

Particular active variants:
                                        (SEQ ID NO: 75)
---FLFISCNNSGKDGNTSA, (SEQ ID NO: 76)
-TLFLFISCNNSGGD----T, (SEQ ID NO: 31)
MTLFLFISCNNSGKGGDSAS, (SEQ ID NO: 77)
MTLFLFISCNNSGKDGNSAS, (SEQ ID NO: 78)
-----FISCNNSGKDGNTSA, (SEQ ID NO: 79)
---FLFISCNNSGKDGN---, (SEQ ID NO: 80)
MTLFLFISCNNSGKD-----, (SEQ ID NO: 81)
MTLFLFISCNNSGKGGDSA-, (SEQ ID NO: 82)
MTLFLFISCNNSGKDGNSA-, (SEQ ID NO: 83)
MTLLLFISSNTSGKDGNSSA, (SEQ ID NO: 84)
MTLFLFISCNNSGKDGNASA
```

4. KFYSSLRLEVRKIEQ (RecA (231-245); SEQ ID NO:3))

In active variants of this peptide, one or more of amino acids S4, and/or I13 can be substituted with an amino acid replacement, or one or more of amino acids K1, F2, Y3, S4, S5, L6, R7, L8, E9, V10, R11, and/or I13 can be replaced.

```
Consensus sequence #1:
                                        (SEQ ID NO: 85)
K F Y (S or A) SLRLEVRK (I or V) E Q.

Consensus sequence #2:
                                        (SEQ ID NO: 86)
(K or I) (F, I, or L) (Y, F, or D)

(S or A) (S or N) (L or R) (R, F,

N, or Q) (L, N or Y) (E or D)

(V, A, I, or E) (R, V, I, K, or N)

K (I, S, or V) E Q.

Particular active variants:
                                        (SEQ ID NO: 87)
KFYASLRLEVRKIEQ, (SEQ ID NO: 88)
KFYASLRLEVRKVEQ, (SEQ ID NO: 89)
KFYSNRFLEIVKSE-, (SEQ ID NO: 90)
-IFSNLQNEAKKIEQ, (SEQ ID NO: 91)
KFYSSLRLEVRKVEQ, (SEQ ID NO: 92)
-FYSSLNYDENKI--, (SEQ ID NO: 93)
KFYISVKLEYK----,
```

5. GFISCDLFIRYEMKE (SEQ ID NO: 22)

In active variants of this peptide, one or more of amino acids S4, and/or I13 can be substituted with an amino acid replacement, or one or more of amino acids G1, D6, I9, Y11, M13 can be substituted.

```
Consensus sequence:
                                            (SEQ ID NO: 94)
(G or S) FISC (D or N) L F (I or T)
R (Y or D) E (M or I) K E.
Particular active variants:
                                            (SEQ ID NO: 95)
GFISCDLFIRDEIKE,
                                            (SEQ ID NO: 96)
SFISCNLFTRDEIKE,
```

6. KKPMN KKGKG KIARK KGKSK VSRKE PYIHS (SEQ ID NO:23)

In active variants of this peptide, one or more of amino acids P3, M4, G8, G10, I12, K16, G17, K18, S19, K20, V21, S22, R23, E25, Y27, and/or I28 can be substituted with an amino acid replacement; or one or more of amino acids K2, P3, M4, N5, K6, K7, G8, G10, K11, I12, A13, R14, K16, G17, K18, S19, K20, V21, S22, R23, K24, E25, Y27, I28, H29 can be substituted.

```
Consensus sequence #1:
                                            (SEQ ID NO: 97)
K K (P or S) (M, I, or L) N K K (G or D)

K (G or D) K (I or V) A R K (K or N) (G or V) (K or E) (S or G) (K or N) (V or A)

(S or V) (R, G, or K) K (E or D) P (Y, S, or F) (I or N) H S.
Consensus sequence #2:
                                            (SEQ ID NO: 98)
K (K or N) (P, S, or D) (M, I, or L)

(N, S, D, or T) (K or N) (K, Q, or E)

(G, S, or D) K (G, S, or D) (K, E, or S)

(I or V) (A, S or V) (R or K) K (K, Q,

N, or L) (G, R, or V) (K, D, E, or N)

(S, N, G, A, D, or W) (K, N, I, D, or R)

(V, A, or E) (S, V, T, or F) (R, G, or K)

(K or Q) (E or D) P (Y, S, or F) (I, N,

T, or V) (H, N, or T) S.
Particular active variants:
                                            (SEQ ID NO: 99)
KNSMNKKGKGKIARKKGKSKVSRKEPSIHS,
                                            (SEQ ID NO: 100)
KKSLNKKGKDKVARKKVEGNAVKKDPFNH-,
                                            (SEQ ID NO: 101)
KKPMNKKGKGKIARKNGKSKVSGKEPFIHS,
                                            (SEQ ID NO: 102)
KKPMNKKGKGKIARKKVKSKVSRKEPYIHS,
                                            (SEQ ID NO: 103)
KKPIN KQGKS KVSRK QGKSN VSRKE PSIHS,
```

7. TILVNLLISCGLTGA (SEQ ID NO:43)

In active variants of this peptide, one or more of amino acids N5, I8, and/or S9 can be substituted with an amino acid replacement; or one or more of amino acids I2, V4, N5, L6, L7, I8, S9, G11, and/or T13 can be substituted.

```
Consensus sequence #1:
                                            (SEQ ID NO: 104)
T I L V (N or S) L L (I or V)

(S or A) C G L T G A.
Consensus sequence #2
                                            (SEQ ID NO: 105)
T (I, L, or V) L (V, I, or L) (N or S)

(L or F) (L or F) (I or V) (S or A) C (G or S) L (T or K) G A.
Particular active variants:
                                            (SEQ ID NO: 43)
TILVNLLISCGLTGA,
                                            (SEQ ID NO: 106)
TILVSLLISCGLTGA,
                                            (SEQ ID NO: 107)
TILVNLLVACGLTGA,
                                            (SEQ ID NO: 108)
TILVSLLVACGLTGA,
                                            (SEQ ID NO: 109)
---VSLLVACGLTG-,
                                            (SEQ ID NO: 110)
-ILVNLFLSCG----,
                                            (SEQ ID NO: 111)
TILVNLFLVS-----,
                                            (SEQ ID NO: 112)
TLIVGLLVACSLTG-,
                                            (SEQ ID NO: 113)
-ILVFFLISC-----,
                                            (SEQ ID NO: 114)
TVLI--LISCSL---,
                                            (SEQ ID NO: 115)
TLLVSLFIACSLTG-,
```

8. KIEFSKFTVKIKNKD (SEQ ID NO:25)

In active variants of this peptide, one or more of amino acids E3, K6, K10 and/or N13 can be substituted with an amino acid replacement; or one or more of amino acids I2, E3, S5, K6, T8, V9, K10, N13, and/or K14 is substituted.

```
Consensus sequence:
                                            (SEQ ID NO: 116)
K I (E or K) F S (K or E) F T V (K or N)
I K (N or Y) K D.
Particular active variants:
                                            (SEQ ID NO: 117)
KIKFSKFTVKIKNKD,
                                            (SEQ ID NO: 118)
KIEFSEFTVKIKYK-,
                                            (SEQ ID NO: 119)
-IKFSEFTVNIKNK-,
                                            (SEQ ID NO: 120)
-IKFSEFTVKIKYK-,
```

9. VSRKGGLLPDIIIKI (SEQ ID NO:20)

In active variants of this peptide, one or more of amino acids V1, S2, R3, K4, G5, G6, L7, L8, P9, D10, I11 can be substituted with an amino acid replacement.

```
Consensus sequence #1:
                                      (SEQ ID NO: 121)
(V or I) (S, or G) R K G G L L P D I
I I K I.

Consensus sequence #2: sequence
                                      (SEQ ID NO: 122)
(V or I) (S, G, or F) (R or S)
(K, D, or N) (G, A, or D)
(G, N, or E) (L, I, or F) (L or F)
(P, S, or A) (D or E) (I or L) I I K I Particular active variants:
                                      (SEQ ID NO: 123)
IGRKGGLLPDIIIKI, (SEQ ID NO: 124)
VGRKGGLLPDIIIKI, (SEQ ID NO: 125)
VSRKAGLLPDIIIKI, (SEQ ID NO: 126)
VFSNDNFLSELIIKI, (SEQ ID NO: 127)
VFSNDNFLSELIIKI, (SEQ ID NO: 128)
---KAGIFPDLII--,
```

10. NTLDVPPKTFVVKLALGYAE (SEQ ID NO: 19)

In active variants of this peptide, one or more of amino acids L3, D4, V5, P6, P7, T9, F10, V12, K13 can be substituted with an amino acid replacement, or one or more of amino acids L3, D4, V5, P6, P7, K8, T9, V12, K13 can be substituted.

```
Consensus sequence #1:
                                      (SEQ ID NO: 129)
N T (L or Q) (D or E) (V or T) (P or S)
(P or S) K (T or S) (F or I) V (V or I)
(K or R) L A L G Y A E.

Consensus sequence #2:
                                      (SEQ ID NO: 130)
N T (L or Q) (D or E) (V or T) (P or S)
(P or S) (K or R) (T or D) F V (V or I)
(K or R) L A L G Y A E.

Particular active variants:
                                      (SEQ ID NO: 123)
IGRKGGLLPDIIIKI, (SEQ ID NO: 124)
VGRKGGLLPDIIIKI, (SEQ ID NO: 131)
-TQDTPPKTFVIKLALGYAE, (SEQ ID NO: 132)
-TQDTPPKTFVIKLALGYA-, (SEQ ID NO: 133)
-TLEVSSKSIVVRL------,
```

11. IYFYAFNTHIKPLDN (SEQ ID NO: 13)

In active variants of this peptide, one or more of amino acids Y2, F3, Y4, A5, F6, T8, H9, I10, and/or N15 can be substituted with an amino acid replacement, or one or more of amino acids Y2, F3, Y4, A5, F6, T8, H9, I10, D14 can be substituted.

```
Consensus sequence #1:
                                      (SEQ ID NO: 134)
I (Y or G) (F, L, or Y) (Y, or I) (A or S)
(F or L) N (T or M) (H, T, K, or N) (I or V) K P
L D (N or D).

Consensus sequence #2:
                                      (SEQ ID NO: 135)
I (Y or G) (F, L, or Y) (Y, F, I, or L) (A, R, K
or S) (F or L) N (T or M) (H, T, K, or N) (I, V,
or A) K P L (D or N) N.

Particular active variants:
                                      (SEQ ID NO: 136)
IYFYAFNTTVKPLDN, (SEQ ID NO: 137)
IYFYAFNTKAKPLDN, (SEQ ID NO: 138)
IYLYSFNTKIKPLDD-,
```

12. KKICEFIQNQWKKNLNIDVE (SEQ ID NO:45)

In active variants of this peptide, one or more of amino acids K1, K2, I3, C4, E5, I7, N9, W11, N14, D18, V19, E20 can be substituted with an amino acid replacement. Or one or more amino acids K1, K2, I3, C4, E5, I7, Q8, N9, W11, K12, K13, N14, D18, V19, E20 is substituted.

```
Consensus sequence #1:
                                      (SEQ ID NO: 139)
(K or R) (K or E) (I, V, or G) (C, A,
or Y) (E, A, S, N, or T) F (I or L) Q
(N, S, or E) Q (W or F) K K (N, I, or V)
L N I (D or N) (V, I, or L) (E or Q).

Consensus sequence #2:
                                      (SEQ ID NO: 140)
(K or R) (K or E) (I, V, or G) (C, A,
or Y) (E, A, S, N, or D) F (I or L)
(Q or E) (N, S, or E) Q (W, E, F, or K)
(K, N, or I) (K or N) (N, I, or V) L N
I (D or N) (V, I, or L) (E, A, or Q).

Particular active variants:
                                      (SEQ ID NO: 141)
KKICEFIQNQWKKNLNINVE, (SEQ ID NO: 142)
KKICEFIQNQWKKILNIDVE, (SEQ ID NO: 143)
RKIAEFIQNQWKKNLNINVQ, (SEQ ID NO: 144)
KKIAAFIQNQWKKILNINL-, (SEQ ID NO: 145)
KEVASFIQSQWKKVLNIDVE, (SEQ ID NO: 146)
KKVATFIQNQWKKILNINI-,
```

```
KGAEFLQEQFKKILNIKIE,           (SEQ ID NO: 147)

KKIAEFIQNQWKKNLNIDVE,          (SEQ ID NO: 148)

KKICEFIQNQWKKILNIDVE,          (SEQ ID NO: 149)

KEIANFIQSQWKKVLNIDIE,          (SEQ ID NO: 150)

KITAEFLQEQFKKVLNINVA,          (SEQ ID NO: 151)

--AEFLQEQFKKILNINLE,           (SEQ ID NO: 152)
```

13. INKLEAKKTSLKTYSEYEEQ (SEQ ID NO:27)

In active variants of this peptide, one or more of amino acids N2, L4, E5, A6, K7, L11, K12, and/or E19 can be substituted with an amino acid replacement, or one or more of amino acids N2, L4, E5, A6, K7, K8, T9, S10, L11, K12, S15, E16, and/or E19 can be substituted.

```
Consensus sequence #1:
                               (SEQ ID NO: 153)
I (N, E, or D) K (L, S, or I) (E or D)

(A, S, E, or I) (K or E) K T S (L or I)

(K or E) T Y S E Y E (E or D) Q.

Consensus sequence #2:
                               (SEQ ID NO: 154)
I (N, E, or D) K (L, S, or I) (E or D)

(A, S, E, or I) (K or E) (K, N, or S)

(T or X) (S or X) (L, F, or I) (K, E, G, or T) T Y (S, N, or G) (E, D, or S) Y E (E or D) Q (where X is any amino acid).

Particular active variants:
IEKLEAKKTSLKTYSEYEE-,          (SEQ ID NO: 155)

IEKLDSKKTSLKTYSEYEE-,          (SEQ ID NO: 156)

IEKLDSKKTSIETYSEYEE-,          (SEQ ID NO: 157)

IDKSDAKKTSLKTYSEYE--,          (SEQ ID NO: 158)

IEKSDPKSVSLKTYSDY---,          (SEQ ID NO: 159)

--KIEIEKTELKTEYNEIED-,         (SEQ ID NO: 160)
```

14. IDDSIKKIDEELKNT (SEQ ID NO:28)

In active variants of this peptide, one or more of amino acids D2, D3, S4, I5, D9, E11, L12, K13, N14, and/or T15 can be substituted with an amino acid replacement, or one or more of amino acids D2, D3, S4, I5, K6, K7, I8, D9, E10, E11, L12, K13, N14, and/or T15 can be substituted.

```
Consensus sequence #1:
                               (SEQ ID NO: 161)
I (D, E, R, N, or T) (D, E, or N)

(S or X) (I, L, F, or A) K K I (D,

E, or N) E (E or S) (L, F, or I)

(K or L) (N, K, S, D, or E) (T, S, or A) (where X is any amino acid).

Consensus sequence #2:
                               (SEQ ID NO: 162)
I (D, E, G, N, or T) (D, E, or N)

(S or X) (I, L, F, V, or A) (K or

E) (K or N) (I or L) (D, E, or N)

(E or D) (E, A, or S) (L, F, I, or A) (K or N) (N, K, S, D, E, or

G) (T, S, V, or A) (where X is any amino acid).

Particular active variants:
IDDSIKKIEEELKNT,               (SEQ ID NO: 163)

IDDSLKKIEEELK--,               (SEQ ID NO: 164)

IDENFKKIEEEFKDT,               (SEQ ID NO: 165)

ITNSLKKIEEELKEA,               (SEQ ID NO: 166)

IDENFKKIEEEFKD,                (SEQ ID NO: 167)

IEDLIKKINEEILN-,               (SEQ ID NO: 168)

INDSLKKIEEEL---,               (SEQ ID NO: 169)

-DENFKKIEEEFKDT,               (SEQ ID NO: 170)

-DENFKKIEEEFKD-,               (SEQ ID NO: 171)

IDDALENINEELKK,                (SEQ ID NO: 172)

IRESAKKIDESLK-,                (SEQ ID NO: 173)

-EDLIKKINEEILN,                (SEQ ID NO: 174)

--NVIKRIEEEAKN-,               (SEQ ID NO: 175)
```

15. DTGSERSIRYRRRVY (SEQ ID NO:24)

In active variants of this peptide, one or more of amino acids G3, S4, R6, I8, R9, Y10, R12, R13, and/or V14 can be substituted with an amino acid replacement, or one or more of amino acids G3, S4, E5, R6, S7, I8, R9, Y10, R12, R13, V14 can be substituted.

```
Consensus sequence #1:
                               (SEQ ID NO: 176)
D T (G or S) (S or T) E (R or K) S (I, K, or R) (R, K, or A) (Y or F)

R (R or K) (R, H, or C) (V, T, I, or A) Y.
```

Consensus sequence #2:
(SEQ ID NO: 177)
D T (G or S) (S or T) (E or D) (R or K) (S or A) (I, K, or R) (R, K, or A) (Y or F) R (R or K) (R, H, C, or N) (V, T, I, or A) Y Particular active variants:
(SEQ ID NO: 178)
DTSSERSIRYRRHVY, (SEQ ID NO: 179)
DTGTERSIRYRKRTY, (SEQ ID NO: 180)
DTGTERSIRFRRHTY, (SEQ ID NO: 181)
DTGTERSIKFRRHTY, (SEQ ID NO: 182)
DTGTERSKAYRKRAY, (SEQ ID NO: 183)
DTGTERSIRYRRRTY, (SEQ ID NO: 184)
---TERSIRYRKRTY, (SEQ ID NO: 185)
---TERSIRYRRHTY, (SEQ ID NO: 186)
---TERSIRFRRHTY, (SEQ ID NO: 187)
---SEKARKYRRNVY, (SEQ ID NO: 188)
---TERSKAYRKRAY,

16. FEDAMKLGLALYLDY (SEQ ID NO: 1)

In active variants of this peptide, one or more of amino acids A4, L7, L9, and/or A10 can be substituted with an amino acid replacement.

Consensus sequence:
(SEQ ID NO: 189)
F E D (A or V) M K (L or I) G (L or I) (A or T) L Y L D Y.

Particular active variants:
(SEQ ID NO: 190)
FEDAMKLGIALYLDY, (SEQ ID NO: 191)
FEDAMKIGIALYLDY, (SEQ ID NO: 192)
FEDAMKLGLTLYLDY,

17. LIRFTTISLGWDSNN (SEQ ID NO: 2)

In active variants of this peptide, one or more of amino acids A4, L7, L9, and/or A10 can be substituted with an amino acid replacement.

Consensus sequence:
(SEQ ID NO: 193)
L (I or F) R F (T or S) (T or A) I S (L or I) G (W or S) D S N N.

Particular active variants:
(SEQ ID NO: 194)
LFRFSAISIGS----, (SEQ ID NO: 195)
LFRFSAISIGSDSNN, (SEQ ID NO: 196)
LFRFSAI-SIG----S, (SEQ ID NO: 197)
LIRFSAISLGSDSNN, (SEQ ID NO: 198)
LIRFTAISIGWDSNN,

18. NSRSRYNNFYKKEADFLGAA (SEQ ID NO: 26)

In active variants of this peptide, one or more of amino acids S4, N7, F9, G18 can be substituted with an amino acid replacement.

Consensus sequence:
(SEQ ID NO: 199)
N S R (S or G) R Y (N or D) N (F, S, or Y) Y K K E A D F L (G or I) A A.

Particular active variants:
(SEQ ID NO: 200)
NSRSRYDNFYKKEADFLGAA, (SEQ ID NO: 201)
NSRSRYNNYYKKEADFLGAA, (SEQ ID NO: 202)
NSRGRYNNSYKKEADFLIAA,

19. NKTFNNLLKLTILVN (SEQ ID NO: 41)

In active variants of this peptide, one or more of amino acids T3, F4, N5, L7, L8, and/or T11 can be substituted with an amino acid replacement.

Consensus sequence:
(SEQ ID NO: 203)
N K (T, E, or A) (F or Y) (N, K, or G) N (L, V, or I) (L or I) K L (T or G) I L V N.

Particular active variants:
(SEQ ID NO: 204)
NKAFGNLLKEGILVN, (SEQ ID NO: 205)
NKIYKDLLKIAILVN, (SEQ ID NO: 206)
NKTYKNLLKLTILVN, (SEQ ID NO: 207)
NKTFNNVIKLTILVN,

20. PFILEAKVRATTVAE (SEQ ID NO: 44)

In active variants of this peptide, one or more of amino acids P1, L4, E5, A6, V8, R9, A10, T11, T12 can be substituted with an amino acid replacement.

Consensus sequence:
(SEQ ID NO: 208)
(P or S) F I (L or K) (E, K, or Q) (A or S) K (V, M, or I) (R, K, or Q) (A or G) (T or I) (T, E, A, D, K, Q) V A E.

Particular active variants:

SFILEAKVRATTVAE, (SEQ ID NO: 209)

SFILEAKMRGTTVAE, (SEQ ID NO: 210)

PFILKAKMRGTEVTE, (SEQ ID NO: 211)

-FIKQAKVRAIKVAE, (SEQ ID NO: 212)

-FILKAKIKAIQVAE, (SEQ ID NO: 213)

-FILKAKIQAIQVAE, (SEQ ID NO: 214)

In another analysis, the inventors aligned and compared the sequences of Table 1 with comparable peptides from individual subspecies of *B. burgdorferi* as well as *B. garinii* and *B. afzelli*, to identify the conserved and dispensable amino acid residues. Sera from European Lyme disease patients, who have been exposed to *B. garinii* and/or *B. afzelli* (which, along with *B. burgdorferi*, are endemic in Europe), contain antibodies that bind to the peptides represented by SEQ ID NOs: 1-28 and 41-47, which are derived from the North American endemic strain, *B. burgdorferi*. In view of this cross-reactivity, it is clear that for a given peptide which binds to sera containing antibodies against all three strains, and which exhibits variability among particular amino acid residues in the three species, the variable regions are not essential for optimal binding of the peptide to the antibody.

The following four examples are representative of such alignments/comparisons, and depict the variability found in peptide populations among the three primary strains of Lyme disease-inducing *Borrelia*. (1) A peptide from *B. garinii* corresponding to the peptide identified as SEQ ID NO:11 has the sequence YGENWTNPENIVVSGAYKLK-ERLINDKIVIEKNEK (SEQ ID NO:29), which differs from SEQ ID NO:11 by twelve amino acids, at positions 3, 7, 11, 13, 16, 17, 23, 24, 26, 28, 30, 34, while a corresponding peptide from *B. afzelli* (YKGNWTNPENMVTSGPFKLK-KRLPNEKIIFEKN (SEQ ID NO:30)) differs from SEQ ID NO 11 by nine amino acids at positions 2, 3, 7, 21, 23, 28, 29, 34, 35. Thus, the sequences derived from *B. garinii* and *B. afzelli* are active variants of the peptide of SEQ ID NO:11. (2) A peptide from *B. garinii* corresponding to the peptide identified as SEQ ID NO:8 has the sequence MTLFLFIS-CNNSGKGGDSAS (SEQ ID NO:31), which differs from SEQ ID NO:8 by five amino acids, e.g. at positions 15, 17, 18, 19, and 20. Thus, the sequence derived from *B. garinii* is an active variant of the peptide of SEQ ID NO:8. (3) Peptides derived from both *B. garinii* and *B. afzelli* corresponding to the peptide identified as SEQ ID NO:20 have the sequence VGRKGGLLPDIIIKI (SEQ ID NO:32), which differs from SEQ ID NO:20 by one amino acid, at position 2. Thus, the sequences derived from *B. garinii* and *B. afzelli* are active variants of the peptide of SEQ ID NO:20. (4) A peptide from *B. garinii* corresponding to the peptide identified as SEQ ID NO:1 has the sequence FEDAMKIGIA-LYLDY (SEQ ID NO:33), which differs from SEQ ID NO:1 by two amino acids, at positions 7 and 9, while a corresponding peptide from *B. afzelli* (FEDAMKLGIALYLDY (SEQ ID NO:34) differs from SEQ ID NO 1 by one amino acid at positions 9. Thus, the sequences derived from *B. garinii* and *B. afzelli* are active variants of the peptide of SEQ ID NO: 1. A skilled worker, knowing the sequences represented by any one of SEQ ID NOs:1-28, in view of the observation that the peptide can bind to *Borrelia*-induced antibodies from all three of the Lyme-disease-inducing *Borrelia* described above, can readily determine the sequences of comparable peptides from *B. garinii* and *B. afzelli* and thereby derive a consensus sequence which encompasses active variants of the *B. burgdorferi* sensu lato peptide.

The term "a peptide of the invention," as used herein, refers to a peptide represented by any of the sequences shown in Table 1, or an active variant thereof, particularly those peptides which contribute to specific and sensitive assays, such as the peptides of Group I or Group II.

A number of the indicated peptides are cross-reactive. For example, three of the eight serum samples that were used for initial peptide screening were obtained from endemic European areas where *B. afzelli*, and *B. garinii* predominate.

Based on sequence comparisons such as the ones described above, a skilled worker can generate consensus sequences that represent each of the SEQ ID NOs: 1-28 and 41-47 and active variants thereof. For example, SEQ ID NO:11 can be represented by the consensus sequence: Y(K/G)(Q/E/G)NWT(S/N)PEN(M/I)V(T/V)SG(P/A)(F/Y) KLK(E/K)R(I/L)(P/I)N(E/D)K(Y/I)(V/I)(F/I)EKN(N/E/-) (K/-) (SEQ ID NO:35). Other amino acids (either homologous or non-homologous) can also be substituted at the variable positions, provided the substitutions do not significantly impact the ability of the peptide to bind to an antibody generated against infection with a pathogenic *Borrelia*.

Any of the peptides of the invention, can optionally contain a cysteine (C) residue at its N terminus, to facilitate the attachment of a biotin molecule, which can be useful for binding the peptide to a surface comprising avidin.

One aspect of the invention is a method for diagnosing Lyme disease in a subject (e.g. for diagnosing exposure to and/or infection by a pathogenic *Borrelia*), comprising measuring a bodily fluid (which would be expected to contain antibodies) of the subject for the presence of an antibody against a causative agent of Lyme disease (e.g. an antibody capable of binding to such an agent), wherein an elevated level of antibody in the subject compared to a corresponding level of antibody in a control (such as a known unaffected subject) indicates an infection by the causative agent and/or that the subject has Lyme disease. A "causative agent for Lyme disease," as used herein, includes a pathogenic species of *B. burgdorferi, B. afzelli*, or *B. garinii*. Screening with serum derived from both North America and Europe indicates that screening with peptides derived from *B. burgdorferi* are predictive of reactivity to the same peptide present in the other two strains. If this were not the case, the European Lyme serum would not bind to peptides the inventors used for these studies. Other species of *Borrelia* which have been implicated in Lyme disease, such as, e.g., *B. lusitaniae* and *B. valaisianae*, are also included, provided they induce antibodies which can react specifically with a peptide of the invention. It is to be understood that the term "pathogenic *Borrelia*," as used herein, refers to any such pathogenic genospecies that causes Lyme disease. "Lyme disease," as used herein, refers to an disease which exhibits the characteristics as summarized in Dattwyler, R. J. and Wormser, G. "Lyme borreliosis." in Infectious Diseases Medicine and Surgery (eds.) S. Gorbach and J. Bartlett, 3$^{rd}$ edition, Saunders Pub. New York, N.Y., 2003 and which is caused by a pathogenic *Borrelia*.

One embodiment of this method comprises contacting (incubating, reacting) a peptide of the invention with a sample of a biological fluid (e.g. serum or CSF) from a subject (e.g. human or other animal) to be diagnosed (a subject suspected of having Lyme disease). In the presence of an antibody response to infection with a pathogenic *Borrelia*, an antigen-antibody complex is formed. The antigen-antibody complex is sometimes referred to herein as an antibody-peptide complex, a peptide-antibody complex, or an antibody-epitope complex; these terms are used interchangeably. Subsequently the reaction mixture is analyzed to determine the presence or absence of this antigen-antibody complex. A variety of conventional assay formats can be employed for the detection, such, e.g., as ELISA, microarray analysis, Luminex bead based assays or lateral flow methods. The presence of an elevated amount of the antibody-peptide complex indicates that the subject was exposed to and infected with a pathogenic *Borrelia* capable of causing Lyme disease. In any detection assay of the invention, a positive response is defined as a value 2 or 3 standard deviations greater than the mean value of a group of healthy controls. For the purposes of the initial screening, the inventors defined a positive response to the peptide as a statistically significant difference in the mean binding of serum antibodies from patients with confirmed Lyme disease, compared to serum from patients confirmed to be sero-negative for Lyme disease (normal controls), and serum from patients that are positive for Syphilis (RPR+), where significance is measured as p<0.05 as determined using a Kruskal-Wallis test followed by a Dunn's comparison test. Serum antibody binding was compared at single dilutions (1:50), as well as reciprocal 50% binding titers (several dilutions of each serum sample were prepared and incubated with each peptide; the 50% binding titer was determined as the dilution of antibody at which the absorbance measured in the ELISA assay had reached 50% of the maximum absorbance recorded for any of the dilutions). Ultimately, when a multi-peptide assay has been completed, the cutoff for a positive response will be greater than 3 SD from the mean of a group of healthy controls. In some embodiments, a second tier assay is required to provide an unequivocal sero-diagnosis of Lyme disease.

Peptides, compositions comprising the peptides (such as diagnostic compositions), kits and methods of the invention offer a number of advantages. For example, they allow for simple, inexpensive, rapid, sensitive and accurate detection of Lyme disease, and avoid serologic cross-reactivity with other conditions with "Lyme-like" symptoms, such as myalgias, arthralgias, malaise or fever, including conditions such as syphilis, chronic arthritis, and multiple sclerosis. This allows for an accurate diagnosis. Furthermore, a diagnostic test of the invention (e.g. an ELISA assay or a Luminex bead based assay) is useful in serum samples that contain anti-OspA antibodies or other antibodies produced in response to a vaccine based on the outer surface proteins of *Borrelia*; the peptides of the invention do not cross-react with such antibodies, thereby allowing the differentiation of vaccinated individuals from individuals who were naturally infected with *B. burgdorferi*. In addition, the small size of a peptide of the invention allows it to be readily combined with other diagnostic peptides, described herein or known to those of skill in the art, e.g. from other *Borrelia* proteins, into a linear, multi-antigenic peptide for use in a diagnostic assay. The use of multiple peptides of the invention in a single assay (e.g. in the form of a cocktail) will increase the sensitivity of the assay for positive Lyme samples but not for the cross-reactivity controls and normal serum. By including peptides from a variety of *Borrelia* proteins, the sensitivity of an assay is greatly increased over assays in which only a single peptide, or several peptides from a single protein, are used.

One aspect of the invention is an isolated peptide of the invention which binds specifically to an antibody induced by a causative agent of Lyme disease (a pathogenic *Borrelia*), e.g. in a sample from a subject having Lyme disease. An antibody "induced by" a pathogenic *Borrelia* is sometimes referred to herein as an antibody "against" the pathogenic *Borrelia*. An active variant may have one or more amino acid (e.g., conservative amino acid) replacements in, e.g., amino acid residues as described elsewhere herein. Suitable conservative amino acid substitutions will be evident to a skilled worker. For example, conservative replacements are those that take place within a family of amino acids that are related in their side chains and chemical properties. These include, e.g., (1) acidic: aspartate, glutamate; (2) basic: lysine, arginine, histidine; (3) nonpolar: alanine, valine, leucine, isoleucine, proline, phenylalanine, methionine, tryptophan; (4) uncharged polar: glycine, asparagine, glutamine, cysteine, serine, threonine, tyrosine; (5) aliphatic: glycine, alanine, valine, leucine, isoleucine, serine, threonine, with serine and threonine optionally be grouped separately as aliphatic-hydroxyl; (6) aromatic: phenylalanine, tyrosine, tryptophan; (7) amide: asparagine, glutamine; and (9) sulfur-containing: cysteine and methionine (see, for example, Biochemistry, 2nd ed., Ed. by L. Stryer, W H Freeman and Co.: 1981). Whether a change in the amino acid sequence of a peptide results in an active variant can be readily determined by assessing the ability of the variant peptide to produce a response in e.g. an ELISA in a fashion similar to the wild-type peptide, or to competitively inhibit such a response. Peptides in which more than one replacement has been introduced can be readily tested in the same manner. Generally, between one and about four codon changes can be present in such a variant. In embodiments, one, two, three, or four such changes are present in a variant consisting of one or more of the peptides listed in Table 1. Muteins and analogs are included.

Generally, a peptide of the invention is derived from any one of a number of immunodominant proteins of a pathogenic *Borrelia* species that causes Lyme disease.

Another aspect of the invention is a peptide of the invention that is linked to (e.g. associated with, coupled, or fused to, directly or indirectly) one or more additional moieties. The association may be, for example, via a terminal amino acid linker (such as Lys or Cys) or a chemical coupling agent. A peptide may be linked directly to one or more moieties, such as other peptides. For example, a peptide may be synthesized so as to contain a peptide of the invention flanked by one or more additional peptides (e.g. from *Borrelia*), on its N-terminus, its C-terminus, or both. In one embodiment, linked peptides are separated by a spacer. The spacer may consist, for example, of between about one and five (e.g., three) amino acids, preferably uncharged amino acids, e.g., aliphatic amino acids such as Gly or Ala. In one embodiment, the spacer is a triple Gly spacer. A linker may, e.g., provide distance between epitopes of different antigenic peptides. The additional moiety can be, e.g., a detectable label, a fusion partner (such as a chemical compound, or a peptide having an epitope from the same or a different protein from the same or a different pathogenic *Borrelia*), or a substrate that immobilizes the peptide (e.g. a microwell plate, an Immobilon or nitrocellulose membrane, or latex beads).

Another aspect of the invention is a diagnostic reagent, comprising a peptide of the invention and, optionally, a system for detecting a complex of the peptide and a specific antibody, and/or a substrate for immobilizing the peptide.

Another aspect of the invention is a composition comprising a peptide of the invention and, optionally, one or more additional polypeptides or peptides that specifically recognize antibodies to a causative agent of Lyme disease. Any combination of 2, 3, 4, 5, 5, 7, 8, 9, 10, 11, 12, 13, 14, 15 or more of the peptides of the invention, including active variants of the peptides listed in Table 1, can be present in such a combination; or other suitable peptides can be used. The additional polypeptides or peptide(s) may be used in conjunction with a peptide of the invention as part of a cocktail; or one or more of the additional polypeptides or peptides may be fused at the N-terminus and/or the C-terminus of a peptide of the invention to form a fusion peptide or polypeptide. The terms peptide and polypeptide are used interchangeably herein; for example, an amino acid consisting of three 9-15-mer peptides linked directly to one another can be referred to as either a peptide or a polypeptide.

Another aspect of the invention is a kit for diagnosing Lyme disease in a subject, which comprises one or more peptides of the invention, or one or more compositions of the invention, and optionally comprises one or more additional peptides or polypeptides as noted above. The peptide(s) may comprise a detectable label, or the kit may include a detection system (e.g. a labeled conjugate and a reagent; or beads comprising unique spectral signatures) for detecting a peptide which is specifically bound to an antibody in the sample. In one embodiment, the kit contains a substrate for immobilizing the peptide, such as a microwell plate, an Immobilon or nitrocellulose membrane, latex beads, or polystyrene beads.

Another aspect of the invention is a method for diagnosing Lyme disease in a subject suspected of having antibodies against a causative agent of Lyme disease (e.g. for diagnosing exposure to and/or infection by a pathogenic *Borrelia*), comprising contacting a sample from the subject a with a peptide or composition of the invention, under conditions effective for the formation of a specific peptide/antibody complex, and detecting the presence (e.g. the amount) of a peptide/antibody complex. In one embodiment, the detection method is an enzyme-linked immunosorbent assay (ELISA); and/or is carried out in vitro.

An isolated peptide of the invention can be of any desirable size. For example, it can consist of 1, 2, or 3 or more, or 1, 2, or 3 fewer, amino acids from the N-terminus, the C-terminus, or both termini of a peptide of the invention. In general, because peptides smaller than 8 amino acids are not functional for binding to an antibody, peptides of the invention are generally no smaller than 8 amino acids. In embodiments of the invention, a peptide is no more than 18, 20, 22, 24, 26, 28, 30, 35, 40, 45, 50, 55 or 60 amino acids in length. Peptides which are too long, such a full-length proteins, generally engage in non-specific interactions and thus are not specific enough to be suitable for an assay of the present invention.

Other suitable peptides include any of the other peptides described herein which further comprise, attached at the N-terminal and/or C-terminal end, one or more of the consecutive amino acids from the *B. burgdorferi* strain from which the peptide was isolated, which abut the peptide sequences in the naturally occurring protein from which the peptide is derived, or active variants of those sequences. Optionally, such a peptide can contain an N-terminal Cys or Lys residue, e.g. to facilitate the addition of a Biotin molecule. Furthermore, active variants of the peptides are included. An isolated peptide of the invention can be associated with a second moiety, used as a diagnostic reagent, present in a composition comprising one or more additional polypeptides or peptides that specifically recognize antibodies to a causative agent of Lyme disease, or present in a kit for diagnosing Lyme disease.

A peptide, including a modified form thereof, which "binds specifically" to ("is specific for"; binds "preferentially" to) an antibody against a pathogenic *Borrelia* interacts with the antibody, or forms or undergoes a physical association with it, in an amount and for a sufficient time to allow detection of the antibody. By "specifically" or "preferentially" is meant that the peptide has a higher affinity, e.g. a higher degree of selectivity, for such an antibody than for other antibodies in a sample. That is, the peptide has an affinity for the antibody of at least about 2-fold higher than for other antibodies in the sample. The affinity or degree of specificity can be determined by a variety of routine procedures, including, e.g., competitive binding studies.

An "isolated" peptide of the invention is in a form other than it occurs in nature, e.g. in a buffer, in a dry form awaiting reconstitution, as part of a kit, etc. In some embodiments, the peptide is substantially purified. The term "substantially purified", as used herein refers to a molecule, such as a peptide, that is substantially free of other proteins, lipids, carbohydrates, nucleic acids and other biological materials with which it is naturally associated. For example, a substantially pure molecule, such as a peptide, can be at least about 60%, by dry weight, preferably at least about 70%, 80%, 90%, 95%, or 99% the molecule of interest. An isolated or purified peptide of the invention differs from the protein from which it was derived at least because of broken bonds between the ends of the peptide and the intact protein. Synthetic peptides are, of course, not naturally occurring.

An "active variant" of a peptide, such as the peptides in Table 1, refers to a peptide which retains the ability to specifically recognize (bind to) an antibody against a causative agent of Lyme disease.

The peptides of the invention may be modified by a variety of techniques, such as by denaturation with heat and/or SDS. A peptide of the invention may be modified to provide an additional N- or C-terminal amino acid sequence suitable for biotinylation, e.g., cysteine or lysine; suitable for chemical lipidation, e.g., cysteine; or the like.

Peptides of the invention may be modified by any of a variety of known modifications. These include, but are not limited to, glycosylation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma carboxylation, glycosylation, GPI anchor formatoin, hydroxylation, iodination, methylation, myristoylation, oxidation, proteolytic processing, phosphorylation, prenylation, racemization, selenoylation, sulfation, ubiquitination, modifications with fatty acids, transfer-RNA mediated addition of amino acids to proteins such as arginylation, etc. Analogues of an amino acid (including unnatural amino acids) and peptides with substituted linkages are also included.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in many basic texts, such as Proteins—Structure and Molecular Properties, 2nd ed., T. E. Creighton, W.H. Freeman and Company, New York (1993). Many detailed reviews are available on this subject, such as by Wold, F., Posttranslationail Covalent Modification of Proteins, B. C. Johnson, Ed., Academic Press, New York 1-12 (1983); Seifter et al. (1990) Meth. Enzymol. 182:626-646 and Rattan et al. (1992) Ann. N.Y. Acad. Sci. 663:48-62.

Peptides of the invention that consist of any of the sequences discussed herein may be modified by any of the discussed modifications. Such peptides still "consist of" the amino acids.

Peptides of the invention may be associated with one or more further moieties. The association can be covalent or non-covalent, and can be, for example, via a terminal amino acid linker (such as Lys or Cys) or a chemical coupling agent. An additional moiety can be, e.g., a detectable label, a fusion partner (such as a chemical compound or a peptide having an epitope of another pathogenic *Borrelia*), or a substrate that immobilizes the peptide (e.g. a microwell plate, an Immobilon or nitrocellulose membrane, or latex or polystyrene beads).

A peptide of the invention can be fused to a fusion partner (e.g. a peptide or other moiety) that can be used to improve purification, to enhance expression of the peptide in a host cell, to aid in detection, to stabilize the peptide, etc. Examples of suitable compounds for fusion partners include polyethylene glycol, PEGylation, or other chemicals. Among the many suitable peptide or polypeptide fusion partners are, e.g., β-galactosidase, glutathione-S-transferase, a histidine tag, etc. In some embodiments, a peptide of the invention is provided with a detectable label, such as those described below.

A peptide of the invention can be associated with a substrate that immobilizes the peptide. The substrate can be, e.g., a solid or semi-solid carrier, support or surface, including a bead. The association can be covalent or non-covalent, and can be facilitated by a moiety associated with the peptide that enables covalent or non-covalent binding, such as a moiety that has a high affinity to a component attached to the carrier, support or surface. For example, the peptide can be associated with a biotin moiety, and the component associated with the surface can be avidin. The peptide can be immobilized on the solid or semi-solid surface or carrier either prior to or after the addition of the sample containing antibody.

A peptide of the present invention can be in the form of a pharmaceutically acceptable salt. Suitable acids and bases that are capable of forming salts with the peptides of the present invention are well known to those of skill in the art, and include inorganic and organic acids and bases.

A peptide of the invention can be produced using conventional chemical synthesis techniques, such as those described, e.g., in G. Barony et al., The Peptides: Analysis, Synthesis & Biology, Academic Press, pp. 3-285 (1980). Such chemically synthesized peptides can be obtained from commercial suppliers. Peptides produced by chemical synthesis can be obtained at purities exceeding about 95%. Therefore, there is typically a much reduced likelihood for undesirable cross reactivity with random antibodies than by using peptides obtained by other methods.

Alternatively, a peptide of the invention can be produced recombinantly following conventional genetic engineering techniques. To produce a recombinant peptide of the invention, nucleic acid encoding the peptide is inserted into a suitable expression system. Generally, a recombinant molecule or vector is constructed in which the polynucleotide sequence encoding the selected peptide is operably liked to an expression control sequence permitting expression of the peptide. Numerous types of appropriate expression vectors are known in the art, including, e.g., vectors containing bacterial, viral, yeast, fungal, insect or mammalian expression systems. Methods for obtaining and using such expression vectors are well-known. For guidance in this and other molecular biology techniques used for compositions or methods of the invention, see, e.g., Sambrook et al, Molecular Cloning, A Laboratory Manual, current edition, Cold Spring Harbor Laboratory, New York; Miller et al, Genetic Engineering, 8:277-298 (Plenum Press, current edition), Wu et al, *Methods in Gene Biotechnology* (CRC Press, New York, N.Y., current edition), *Recombinant Gene Expression Protocols*, in *Methods in Molecular Biology*, Vol. 62, (Tuan, ed., Humana Press, Totowa, N.J., current edition), and *Current Protocols in Molecular Biology*, (Ausabel et al, Eds.,), John Wiley & Sons, NY (current edition), and references cited therein.

Suitable host cells or cell lines for the recombinant nucleic acids or vectors of the invention transfection by this method include bacterial cells. For example, various strains of *E. coli* (e.g., HB101, MC1061) are well-known as host cells in the field of biotechnology. Various strains of *B. subtilis, Pseudomonas, Streptomyces,* and other bacilli and the like can also be employed in this method. Alternatively, a peptide of the invention can be expressed in yeast, insect, mammalian, or other cell types, using conventional procedures.

Thus, the present invention provides a method for producing a recombinant peptide or polypeptide, which involves transfecting or transforming, e.g., by conventional means such as electroporation, a host cell with at least one expression vector containing a polynucleotide of the invention under the control of an expression control sequence (e.g. a transcriptional regulatory sequence). The transfected or transformed host cell is then cultured under conditions that allow expression of the peptide or polypeptide. The expressed peptide or polypeptide is recovered, isolated, and optionally purified from the cell (or from the culture medium, if expressed extracellularly) by appropriate means known to one of skill in the art, including liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention. One skilled in the art can determine the purity of the peptide or polypeptide by using standard methods including, e.g., polyacrylamide gel electrophoresis (e.g. SDS-PAGE); column chromatography (e.g. high performance liquid chromatography (HPLC)), or amino-terminal amino acid analysis.

Included in the invention are a polynucleotide encoding and/or expressing a peptide or polypeptide of the invention, a vector comprising the polynucleotide, and a host cell comprising the polynucleotide acid or vector.

A peptide of the invention may be used in combination with one or more additional peptides or polypeptides from the same or a different protein, from the same or a different pathogenic *Borrelia* strain, wherein the additional peptide(s) or polypeptide(s) also bind specifically to an antibody against a pathogenic *Borrelia*. The combination may comprise a cocktail (a simple mixture) of individual peptides or polypeptide, or it may be in the form of a fusion peptide or polypeptide (a multimeric peptide). For example, a peptide of the invention may be fused at its N-terminus or C-terminus to another suitable peptide. Two or more copies of a peptide of the invention may be joined to one another, alone or in combination with one more additional peptides. Combinations of fused and unfused peptides or polypeptides can be used. In one embodiment, the additional peptide(s) contain B-cell and/or T-cell epitopes from a protein of a pathogenic *Borrelia*.

Any combination of two or more peptides of the invention can be combined to form a multi-epitope peptide. Furthermore, the peptides can be combined with suitable additional peptides or polypeptides (sometimes referred to herein as "antigenic peptides or polypeptides" or as "agents") that can be derived from *Borrelia* antigens such as OspA, OspB, DbpA, flagella-associated proteins FlaA(p37) and FlaB (p41), OspC (25 kd), BBK32, BmpA(p39), p21, p39, p66 or p83. See, e.g., Barbour et al (1984) *Infect. Immun.* 45, 94-100; Simpson et al. (1990) *J. Clin. Microbiol.* 28, 1329-1337; Hansen et al. (1988) *Infect. Immun.* 56, 2047-2053; Hansen et al. (1988) *Infect. J. Clin. Microbiol.* 26, 338-346; Wilske et al. (1986) *Zentral, Bakteriol, Parsitenkd, Infektionshkr, Hyg. Abt.* 1 *Orig. Reihe, A.* 263, 92-102; Dorward et al. (1991) *J. Clin. Microbiol.* 29, 1162-1170; published NTIS U.S. patent application No. 485,551; European patent application No. 465,204; International Patent Application No. PCT/US91/01500; International Patent Application No. PCT/EP90/02282; International Patent Application No. PCT/DK89/00248; International patent application No. WO92/00055. The peptides described in U.S. Pat. No. 7,887,815 can also be used, as can the 26 amino acid peptide derived from the IR6 region of the *B. burgdorferi* VlsE, which is currently approved by the FDA for use in a peptide-based immunodiagnostic assay in the United States. Polypeptides or peptides derived from other microorganisms can also be used.

One embodiment of the invention—a composition comprising a peptide of the invention and one or more additional agent(s)—is particularly well-suited for diagnosing *Borrelia* infections early after infection (e.g., within one to two weeks after the onset of infection). Among the pathogenic *Borrelia* proteins whose expression has been recognized in early human infection (e.g. to which IgM antibody appears early after infection) are OspC, BBK32, the flagella-associated protein, FlaB(p41), and, to a lesser extent, BmpA(p39), VlsE and the flagella-associated protein, FlaA(p37). Polypeptides or peptides which derive from those polypeptides are suitable for assays for early infection. It is expected that any of the peptides described herein will be useful for early detection.

Some suitable linear epitopes which can be used for the diagnosis of early infection include peptides identified in OspC: PVVAESPKKP (SEQ ID NO:36), reported by Steere et al. (1987) *Ann. Intern Med.* 107, 725-731; ILMTLFLFIS-CNNS (SEQ ID NO:37), reported by AC Steere (2001) *N Engl J Med* 345, 115-25; and one or more epitopes contained between amino acids 161 and 210, reported by Jobe et al. (2003) *Clin Diagn Lab Immunol* 10, 573-8)]. The OspC peptides described in U.S. Pat. No. 6,716,574 can also be used. Other suitable regions, which have been shown not contain major cross-reactive epitopes, have been identified in FlaB(p41), e.g. residues 120 to 235. See, e.g., Crother et al. ((2003) *Infect. Immun.* 71, 3419-3428 and Wang et al. (1999)) *Clin Microbial Rev* 12, 633-653. Other peptides bearing either linear or conformational epitopes are known in the art.

In one embodiment, a peptide from the IR6 region of *B. garinii*, (e.g. the 26 amino acid peptide CMKKDDQIAAA MVLRGMAKDGQFALK (SEQ ID NO48), which is currently in commercial use, or a shorter, 17 amino acid peptide from this region, MKKDDQIAAAIALRGMA (SEQ ID N050). The 17 amino acid peptide and active variants thereof are described in detail in U.S. patent Ser. No. 12/292,044 (now U.S. Pat. No. 7,887,815), which is incorporated by reference herein.

Variants of previously identified epitopes can be readily selected by one of skill in the art, based in part on known properties of the epitopes. For example, a known epitope may be lengthened or shortened, at one or both ends, by about 1-3 amino acids; one, two or more amino acids may be substituted by conservative amino acids; etc. Furthermore, if a region of a protein has been identified as containing a suitable epitope, an investigator can "shift" the region of interest (select different sub-sequences) up to about 5 amino acids in either direction from the endpoints of the original rough region, e.g. to optimize the activity. Methods for confirming that variant peptides are suitable are conventional and routine. Methods for identifying additional epitopes, particularly from variable regions rather than the conserved regions discussed above (e.g. from OspC, BBK32 or DbpA), are discussed in the Examples.

Polypeptides comprising linked peptides may be of any suitable length (e.g. between about 20-80 amino acids, or more), and they may contain any desirable number of linear epitopes (e.g. between about 2-5, or more). For example, between 3 to 5 peptides of about 9-15 amino acids each may be combined, optionally in the presence of suitable spacers, to generate a polypeptide of about 45-50 amino acids. A length of about 120 amino acids can be readily synthesized chemically by current technologies. Other methods may be used to generate longer peptides. The peptides can be linked in any order.

It is expected that multi-epitope peptides of the invention will exhibit significantly more binding to sera from subjects infected with *Borrelia burgdorferi* sensu lato than does one of the peptides of the invention, alone. Methods for making and testing typical multi-epitope peptides are shown in Example VI.

In one embodiment of the invention, a composition comprising one or more of the peptides of the invention and, optionally, one or more of the above-mentioned additional peptides (e.g. in the form of a cocktail or a fusion peptide or polypeptide) is used in a single tier assay, for detecting early/or and late stage Lyme disease. Such a peptide cocktail or fusion polypeptide can be effective in the diagnosis of Lyme disease as caused by a wide spectrum of pathogenic *Borrelia* isolates.

Fusion peptides or polypeptides (multimeric proteins) of the invention can be produced recombinantly or synthesized chemically. They may also include a peptide of the invention fused or coupled to moieties other than amino acids, including lipids and carbohydrates.

One aspect of the invention is a method for detecting Lyme disease in a subject suspected of having antibody against a causative agent of Lyme disease. The diagnostic method is useful for diagnosing subjects exhibiting the clinical symptoms of, or suspected of having, Lyme disease.

The subject can be any subject (patient) in which antibodies can be made against the causative agent and detected. Typical subjects include vertebrates, such as mammals, including wildlife (e.g. mice and chipmunks), dogs, cats, non-human primates and humans.

In one embodiment, the diagnostic method involves detecting the presence of naturally occurring antibodies against pathogenic *Borrelia* (e.g. *B. burgdorferi*) which are produced by the infected subject's immune system in its biological fluids or tissues, and which are capable of binding specifically to a peptide of the invention or combinations of a peptide of the invention and, optionally, one or more suitable additional antigenic polypeptides or peptides.

One embodiment of the invention is a diagnostic immunoassay method, which includes (1) taking a sample of body fluid or tissue likely to contain antibodies; (2) contacting the sample with a peptide of the invention, under conditions effective for the formation of a specific peptide-antibody complex (for specific binding of the peptide to the antibody), e.g., reacting or incubating the sample and a peptide; and (3) assaying the contacted (reacted) sample for the presence of an antibody-peptide reaction (e.g., determining the amount of an antibody-peptide complex).

As used herein, the singular forms "a," "an," and "the" include plural referents unless the context clearly dictates otherwise. Thus, "a" peptide of the present invention, as used above, can be two or more peptides, which can be the same or different. Similarly, when an isolated peptide of the invention is in association with (e.g., linked to) "an" additional peptide, the isolated peptide can be associated with one or more additional peptides.

Phrases such as "sample containing an antibody" or "detecting an antibody in a sample" are not meant to exclude samples or determinations (detection attempts) where no antibody is contained or detected. In a general sense, this invention involves assays to determine whether an antibody produced in response to infection with a pathogenic *Borrelia* is present in a sample, irrespective of whether or not it is detected.

Conditions for reacting peptides and antibodies so that they react specifically are well-known to those of skill in the art. See, e.g., Current Protocols in Immunology (Coligan et al., editors, John Wiley & Sons, Inc) or the Examples herein.

A diagnostic method of the invention comprises taking a sample of body fluid or tissue likely to contain antibodies. The antibodies can be, e.g., of IgG, IgE, IgD, IgM, or IgA type. Generally, IgM and/or IgA antibodies are detected, e.g. for the detection of early infection. IgG antibodies can be detected when some of the additional peptides discussed above are used in the method (e.g. peptides for the detection of flagellum proteins). The sample is preferably easy to obtain and may be serum or plasma derived from a venous blood sample or even from a finger prick. Tissue from other body parts or other bodily fluids, such as cerebro-spinal fluid (CSF), saliva, gastric secretions, mucus, etc. are known to contain antibodies and may be used as a source of the sample.

Once the peptide antigen and sample antibody are permitted to react in a suitable medium, an assay is performed to determine the presence or absence of an antibody-peptide reaction. Among the many types of suitable assays, which will be evident to a skilled worker, are immunoprecipitation and agglutination assays.

In embodiments of the invention, the assay may comprise (1) immobilizing the antibody(s) in the sample, adding a peptide of the invention, and then detecting the degree of antibody bound to the peptide, e.g. by the peptide being labeled or by adding a labeled substance (conjugate, binding partner), such as a labeled antibody, which specifically recognizes the peptide; (2) immobilizing a peptide of the invention, adding the sample containing an antibody(s), and then detecting the amount of antibody bound to the peptide, e.g. by adding a labeled substance (conjugate, binding partner), such as a labeled antibody, which specifically recognizes the antibody; or (3) reacting the peptide and the sample containing antibody(s) without any of the reactants being immobilized, and then detecting the amount of complexes of antibody and peptide, e.g. by the peptide being labeled or by adding a labeled substance (conjugate, binding partner), such as a labeled antibody, which specifically recognizes the peptide.

Immobilization of a peptide of the invention can be either covalent or non-covalent, and the non-covalent immobilization can be non-specific (e.g. non-specific binding to a polystyrene surface in e.g. a microtiter well). Specific or semi-specific binding to a solid or semi-solid carrier, support or surface, can be achieved by the peptide having, associated with it, a moiety which enables its covalent or non-covalent binding to the solid or semi-solid carrier, support or surface. For example, the moiety can have affinity to a component attached to the carrier, support or surface. In this case, the moiety may be, e.g., a biotin or biotinyl group or an analogue thereof bound to an amino acid group of the peptide, such as 6-aminohexanoic acid, and the component is then avidin, streptavidin or an analogue thereof. An alternative is a situation in which the moiety has the amino acid sequence His-His-His-His-His-His (SEQ ID NO:38) and the carrier comprises a Nitrilotriacetic Acid derivative (NTA) charged with $Ni^{++}$ ions. Among suitable carriers, supports or surface are, e.g., magnetic beads or latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles, red blood cells, mono- or polyclonal antibodies or Fab fragments of such antibodies.

The protocols for immunoassays using antigens for detection of specific antibodies are well known in art. For example, a conventional sandwich assay can be used, or a conventional competitive assay format can be used. For a discussion of some suitable types of assays, see Current Protocols in Immunology (supra). In a preferred assay, a peptide of the invention is immobilized to the solid or semi-solid surface or carrier by means of covalent or non-covalent binding, either prior to or after the addition of the sample containing antibody.

Devices for performing specific binding assays, especially immunoassays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microtiter plates, flow-through assay devices, dipsticks and immunocapillary or immunochromatographic immunoassay devices.

In embodiments of the invention, the solid or semi-solid surface or carrier is the floor or wall in a microtiter well; a filter surface or membrane (e.g. a nitrocellulose membrane or a PVDF (polyvinylidene fluoride) membrane, such as an Immobilon membrane); a hollow fiber; a beaded chromatographic medium (e.g. an agarose or polyacrylamide gel); a magnetic bead; a fibrous cellulose matrix; an HPLC matrix; an FPLC matrix; a substance having molecules of such a size that the molecules with the peptide bound thereto, when dissolved or dispersed in a liquid phase, can be retained by means of a filter; a substance capable of forming micelles or participating in the formation of micelles allowing a liquid phase to be changed or exchanged without entraining the micelles; a water-soluble polymer; or any other suitable carrier, support or surface.

In one embodiment of the invention, peptides of the invention are immobilized onto tiny polystyrene beads (microspheres), wherein each peptide is immobilized onto a bead with a unique spectral signature, and are analyzed by the xMAP® technology developed by Luminex Technology (Austin, Tex.) and described in their world wide web site luminexcorp.com.

In some embodiments of the invention, the peptide is provided with a suitable label which enables detection. Conventional labels may be used which are capable, alone or in concert with other compositions or compounds, of providing a detectable signal. Suitable detection methods include, e.g., detection of an agent which is tagged, directly or indirectly, with a fluorescent label by immunofluorescence microscopy, including confocal microscopy, or by flow cytometry (FACscan); detection of a radioactively labeled agent by autoradiography; electron microscopy; immunostaining; subcellular fractionation, or the like. In one embodiment, a radioactive element (e.g. a radioactive amino acid) is incorporated directly into a peptide chain; in another embodiment, a fluorescent label is associated with a peptide via biotin/avidin interaction, association with a fluorescein conjugated antibody, or the like. In one embodiment, a detectable specific binding partner for the antibody is added to the mixture. For example, the binding partner can be a detectable secondary antibody which binds to the first antibody. This secondary antibody can be labeled, e.g., with a radioactive, enzymatic, fluorescent, luminescent, or other detectable label, such as an avidin/biotin system.

A "detection system" for detecting bound peptide, as used herein, may comprise a detectable binding partner, such as an antibody specific for the peptide. In one embodiment, the binding partner is labeled directly. In another embodiment, the binding partner is attached to a signal generating reagent, such as an enzyme that, in the presence of a suitable substrate, can produce a detectable signal. A surface for immobilizing the peptide may optionally accompany the detection system.

In embodiments of the invention, the detection procedure comprises visibly inspecting the antibody-peptide complex for a color change, or inspecting the antibody-peptide complex for a physical-chemical change. Physical-chemical changes may occur with oxidation reactions or other chemical reactions. They may be detected by eye, using a spectrophotometer, or the like.

In one embodiment of the method, the peptide, or a mixture of peptides, is electro- or dot-blotted onto nitrocellulose paper. Subsequently, the biological fluid (e.g. serum or plasma) is incubated with the blotted antigen, and antibody in the biological fluid is allowed to bind to the antigen(s). The bound antibody can then be detected, e.g. by standard immunoenzymatic methods.

In another embodiment of the method, latex or polystyrene beads are conjugated to the antigen(s) of the invention. Subsequently, the biological fluid is incubated with the bead/peptide conjugate, thereby forming a reaction mixture. The reaction mixture is then analyzed to determine the presence of the antibodies.

One assay for the screening of blood products or other physiological or biological fluids is an enzyme linked immunosorbant assay, i.e., an ELISA. Typically in an ELISA, the isolated antigen(s) of the invention is adsorbed to the surface of a microtiter well directly or through a capture matrix (i.e., antibody). Residual, non-specific protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing specific anti-pathogenic *Borrelia* (e.g. *B. burgdoferi*) antibody. The sample can be applied neat, or more often it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with an optimal concentration of an appropriate anti-immunoglobulin antibody (e.g., for human subjects, an anti-human immunoglobulin ($\alpha$HuIg) from another animal, such as dog, mouse, cow, etc.) that is conjugated to an enzyme or other label by standard procedures and is dissolved in blocking buffer. The label can be chosen from a variety of enzymes, including horseradish peroxidase (HRP), $\beta$-galactosidase, alkaline phosphatase, glucose oxidase, etc. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length). The cutoff OD value may be defined as the mean OD+3 standard deviations (SDs) of at least 50 serum samples collected from individuals from an area where Lyme disease is not endemic, or by other such conventional definitions. In the case of a very specific assay, OD+2 SD can be used as a cutoff value.

In one embodiment of an ELISA, a peptide of the invention is immobilized on a surface, such as a ninety-six-well ELISA plate or equivalent solid phase that is coated with streptavidin or an equivalent biotin-binding compound at an optimal concentration in an alkaline coating buffer and incubated at 4° C. overnight. After a suitable number of washes with standard washing buffers, an optimal concentration of a biotinylated form of a composition/antigen of this invention dissolved in a conventional blocking buffer is applied to each well; a sample is added; and the assay proceeds as above.

Another useful assay format is a lateral flow format. Antibody to human or animal antibody or staph A or G protein antibodies is labeled with a signal generator or reporter (i.e. colloidal gold) that is dried and placed on a glass fiber pad (sample application pad). The diagnostic peptide is immobilized on membrane, such as a PVDF (polyvinylidene fluoride) membrane (e.g. an Immobilon membrane (Millipore)) or a nitrocellulose membrane. When a solution of sample (blood, serum, etc) is applied to the sample application pad, it dissolves the colloidal gold labeled reporter and this binds to all antibodies in the sample. This mixture is transported into the next membrane (PVDF or nitrocellulose containing the diagnostic peptide) by capillary action. If antibodies against the diagnostic peptide are present, they bind to the diagnostic peptide striped on the membrane generating a signal. An additional antibody specific to the colloidal gold labeled antibody (such as goat anti-mouse IgG) is used to produce a control signal.

It should be understood by one of skill in the art that any number of conventional protein assay formats, particularly immunoassay formats, may be designed to utilize the isolated peptides of this invention for the detection of pathogenic *Borelia* (e.g. *B. burgdorferi*) infection a subject. This invention is thus not limited by the selection of the particular assay format, and is believed to encompass assay formats that are known to those of skill in the art.

Reagents for ELISA or other assays according to this invention can be provided in the form of kits. Such kits are useful for diagnosing infection with a pathogenic *Borrelia* (e.g. a *B. burgdorferi*), using a sample from a subject (e.g. a human or other animal). Such a diagnostic kit can contain an peptide of the invention (and, if desired, additional peptides as discussed above) and, optionally, a system for (means enabling) detection of a peptide of the invention bound to an antibody against a protein from a pathogenic *Borrelia*, and/or a surface to which the peptide can be bound. In one embodiment, a kit contains a mixture of suitable peptides or means for preparing such mixtures, and/or reagents for detecting peptide-antibody complexes.

The kit can include microtiter plates to which the peptide(s) of the invention have been pre-adsorbed, another appropriate assay device, various diluents and buffers, labeled conjugates or other agents for the detection of specifically bound antigens or antibodies, and other signal-generating reagents, such as enzyme substrates, cofactors and chromogens. Other components of a kit can easily be determined by one of skill in the art. Such components may include coating reagents, polyclonal or monoclonal capture antibodies specific for a peptide of the invention, or a cocktail of two or more of the antibodies, purified or semi-purified extracts of these antigens as standards, MAb detector antibodies, an anti-mouse or anti-human antibody with indicator molecule conjugated thereto, an ELISA plate prepared for absorption, indicator charts for colorimetric comparisons, disposable gloves, decontamination instructions, applicator sticks or containers, a sample preparatory cup, etc. In one embodiment, a kit comprises buffers or other reagents appropriate for constituting a reaction medium allowing the formation of a peptide-antibody complex. Such kits provide a convenient, efficient way for a clinical laboratory to diagnose infection by a pathogenic *Borrelia*, such as a *B. burgdorferi*.

Another aspect of the invention is an isolated antibody, antigen-specific antibody fragment, or other specific binding partner, which is specific for a peptide of the invention, e.g., wherein said antibody, antigen-specific antibody fragment, or specific binding partner is specific for one or the peptides of the invention. Antibodies, e.g. polyclonal, monoclonal, recombinant, chimeric, humanized, single-chain, Fab, and fragments thereof, can be prepared according to any desired method. See also screening recombinant immunoglobulin libraries (e.g., Orlandi et al. (1989) *Proc. Natl. Acad. Sci. USA* 86, 3833-3837; Huse et al. (1989) *Science* 256, 1275-1281); and in vitro stimulation of lymphocyte populations (Winter et al. (1991) *Nature* 349, 293-299). The antibodies can be IgM, IgG, subtypes, IgG2a, IgG1, etc. Antibodies can be used from any source, including, goat, rabbit, mouse, chicken, etc. An antibody specific for a peptide means that the antibody recognizes a defined sequence of amino acids within or including the peptide. Other specific binding partners include, e.g., aptamers and PNA. The preparation of polyclonal antibodies is well-known to those skilled in the art. See, for example, Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992). The preparation of monoclonal antibodies likewise is conventional. See, for example, Kohler & Milstein (1975) *Nature* 256, 495; Coligan et al., sections 2.5.1-2.6.7; and Harlow et al., Antibodies: A Laboratory Manual, page 726 (Cold Spring Harbor Pub. 1988).

An isolated antibody, antigen-specific antibody fragment, or other specific binding partner of the invention can be used for a variety of applications, including therapeutic and diagnostic applications. By an "isolated" antibody is meant herein an antibody molecule that is removed from its original environment (e.g., the natural environment if it is naturally occurring), and is isolated or separated from at least one other component with which it is naturally associated. For example, a naturally-occurring antibody present in its natural living host is not isolated, but the same antibody, separated from some or all of the coexisting materials in the natural system, is isolated. Such antibodies could be part of a composition, and still be isolated in that such composition is not part of its natural environment One aspect of the invention is a method for detecting in a subject the presence of a naturally occurring antigen, itself, in its association with a pathogenic *Borrelia*, using an isolated antibody of the invention. The method can be used to determine that a subject has been exposed to, or infected by, a pathogenic *Borrelia*. In one embodiment, the method comprises contacting a sample (e.g. a bodily fluid or tissue suspected of containing a pathogenic *Borrelia*) from a subject with an antibody of the invention, under conditions effective for the formation of a specific antigen-antibody reaction. Preferably, the antibody is conventionally labeled, either directly or indirectly, for detection, e.g., with an enzyme such as HRP, avidin or biotin, chemiluminescent reagents, etc. Following the binding of the antibody to the antigen, excess labeled antibody is optionally removed, and the reaction mixture is analyzed to determine the presence or absence of the antigen-antibody complex and the amount of label associated therewith.

In one embodiment, a monoclonal or polyclonal antibody of the invention (which is capable of binding to the antigen) is bound to an ELISA plate. A sample, such as a biological fluid, is incubated on the antibody-bound plate and washed. Detection of an antigen-antibody complex and qualitative measurement of the labeled antibody are performed conventionally.

Other useful assay formats include the filter cup and dipstick. In the former assay, an antibody of the invention is fixed to a sintered glass filter to the opening of a small cap. The biological fluid or sample (e.g., about 5 mL) is worked through the filter. If the antigen is present (e.g. following infection with a pathogenic *Borrelia*), it will bind to the filter which can then be visualized through a second antibody/detector. The dipstick assay involves fixing an antigen or antibody to a filter, which is then dipped in the biological fluid, dried and screened with a detector molecule.

Kits for conducting this or other assay methods, using an antibody, antigen-specific antibody fragment, or other specific binding partner of the invention, are also included in the invention.

Much of the preceding discussion is directed to the detection of antibodies against pathogenic *Borrelia*. However, it is to be understood that the discussion also applies to the detection of primed T-cells, either in vitro or in vivo.

It is expected that a cell-mediated immune response (e.g. a T-helper response) is generated, since IgG is produced. It is therefore expected that it will be possible to determine the immunological reactivity between primed T-cells and a peptide of the invention. In vitro this can be done by incubating T-cells isolated from the subject with a peptide of the invention and measuring the immunoreactivity, e.g. by measuring subsequent T-cell proliferation or by measuring release of cytokines from the T-cells, such as IFN-.gamma; these methods are well-known in the art.

When a method of the invention is carried out in vivo, any of a variety of conventional assays can be used. For example, one can perform an assay in the form of a skin test, i.e. by intradermally injecting, in the subject, a peptide of the invention A positive skin reaction at the location of injection indicates that the subject has been exposed to and infected with a pathogenic *Borrelia* capable of causing Lyme disease, and a negative skin response at the location of injection indicates that the subject has not been so exposed/infected. This or other in vivo tests rely on the detection of a T-cell response in the subject.

In the foregoing and in the following examples, all temperatures are set forth in uncorrected degrees Celsius; and, unless otherwise indicated, all parts and percentages are by weight.

EXAMPLES

Example I—Identification and Characterization of Diagnostic Peptides

A. Material and Methods

The following methods are used for the experiments in the following Examples.

1. Peptide Synthesis:

For the epitope mapping studies, synthetic peptides were custom synthesized by the commercial facility, ProImmune (Oxford, England), under the direction of the inventors, using conventional procedures. For each of 10 *B. burgdorferi* proteins, a complete library was generated, consisting of peptides of 15 amino acids, offset by 5 amino acids, i.e. overlapping by 10 amino acids. We provided the sequences of each protein for which a peptide library was generated, specifically: *Borrelia* membrane protein A (BmpA), Decorin-binding protein B (DbpB), flagellar basal body-associated protein (FlilB), oligopeptide ABC transporter II (OppA), BBG33 (putative uncharacterized protein) (Bbg33), outer-surface-protein C type K (OspC typeK), integral outer membrane protein p66 (p66), recombinase A (RecA), outer-surface-protein C type A (OspC type A), and lipoprotein LA7 (LA-7).

Significant binding was demonstrated for multiple peptides within each of the ten proteins that were submitted for analysis. We chose the individual peptides in Table 1 based upon their ability to bind more than 75% of the serum samples, bind to the serum samples at multiple dilutions (indicating high affinity binding), and a low sequence identity with other bacterial species as determined by sequence alignment using the NCBI protein BLAST algorithm on the NCBI website (we chose peptides unique to *Borrelia* species).

2. Test Panels of Sera

For the initial evaluation of the peptides including identified diagnostic epitopes, we had Lifetein (South Plainfield, N.J., 07080) generate peptides containing the epitope. In our initial characterization, we utilized sera from nine patients who had microbiologically (by culture) confirmed Lyme disease. These patients had a positive serologic response demonstrated by western blot, using the current prescribed methods for the laboratory diagnosis of Lyme disease The patients had early Lyme disease.

For further characterization of the peptides, e.g., to determine specificity and sensitivity, we use panels of sera, including sera from a defined number of patients with PCR-confirmed early Lyme disease. The Lyme serum panels are representative of the population of suburban New York and include samples from adults males, females, whites and minorities, reporting to the Lyme disease clinic at Westcheseter Medical Center (Westchester, N.Y.). Lyme disease was confirmed in these patients by PCR (PCR+) or by culture. Sera from normal healthy individuals with neither a known history of Lyme disease nor immunoblot patterns characteristic of the infection obtained from areas endemic and non-endemic for LD are used as negative healthy controls. Serum from patients with Syphilis, rheumatoid arthritis, systemic lupus erythematosus, and *Helicobacter pylori* infection are used as negative controls for cross-reactivity with antibodies raised in response to other diseases (cross-reactivity controls). These serum samples, as well as the negative controls, have been purchased from Bioreclamation, LLC (Westbury, N.Y.).

B. Linear Epitope Mapping of B-Cell Epitopes:

Linear mapping of B-cell epitopes of candidate *B. burgdorferi* proteins was carried out by ProImmune, under the direction of the inventors. A more detailed discussion of the epitope mapping procedure is described on the ProImmune world wide website, at promiimue.com. Briefly, the peptides described above were distributed in a high density microarray format. Each peptide was screened for binding with the eight sets of sera described above, and with appropriate control sera for specificity and sensitivity, as described above. The peptides were ranked with regard to the strength of their binding to the sera.

We chose the individual peptides in table 1 based upon three criteria:

1) their ability to bind at least 75% (%) of the serum samples, 2) their ability to bind to multiple (~50%) of the serum samples at multiple dilutions (indicating high affinity binding), 3) low sequence identity with other bacterial species as determined by sequence alignment using the NCBI protein BLAST algorithm on the NCBI website (we chose peptides unique to *Borrelia* species, and had less than a 50% sequence identity with peptides from other bacteria).

C. Further Characterization of Candidate Peptides, to Determine Specificity and Sensitivity.

ELISA Procedure

Solutions of purified peptides (and control proteins) in 100 mM BIS-TRIS propane buffer (pH9.7) are used to coat commercial microwell plates (MaxiSorp®, Nunc) at 10 m/ml. The coating procedure is as follows: 50 μl of a solution containing the appropriate concentration of antigen is added to each well and the microwell plate incubated either for 1 h at room temperature or overnight at 4° C. The antigen solution is removed from the wells; the plate washed three times with phosphate buffered saline containing 0.05% Tween-20, pH 9 (PBST); and 300 μl of a conventional blocking solution (e.g., 100 mM PBS pH7.4, 5% fetal bovine serum) added. The standard blocking protocol successfully saturates this high antigen binding capacity, leaving low background readings in the control channels. A protein concentration of about 10 μg/ml in the coating buffer is optimal. Following a 60-minute incubation at room temperature, the plates are washed three times with PBST buffer. Although the amount of each peptide bound to the surface and the amount of any one epitope exposed to the solution varies somewhat, the amount of bound epitope is not limiting within the useful range of the ELISA.

A standard procedure for the ELISA tests is employed. For example, human sera is serially diluted (1:2), starting at a 1:50 dilution in 50 μl of blocking buffer. The samples are added in each well and the plate is incubated for 2 h at room temperature. Plates are washed three times with PBST buffer. The horseradish peroxidase conjugated anti-human IgG (H+L) (Jackson ImmunoResearch, West Grove, Pa.) antibody is diluted at 1:15,000 in blocking buffer; 100 ul of this solution is dispensed onto the plate and incubated for 30 minutes at room temperature. Plates are washed three times with TBST buffer and 100 ul of substrate is added (pNPP Microwell Substrate System, KPL, Gaithersburg, Md.) and incubated for 1 h at room temperature. Plates are read at 405 nm on a microplate reader (Molecular Devices, Spectramax 320).

Immobilization of Biotinylpeptide-Streptavidin Conjugates in an ELISA Format.

Biotinylpeptide-Strepavidin conjugates in sodium phosphate buffer are used to coat microwell plates (MaxiSorp®, Nunc). The coating procedure is as follows: antigen is added to each well and the microwell plate incubated either for 1 h at room temperature or overnight at 4 C. The antigen solution is removed from the wells, the plate washed three times with PBS, and 200 ul of blocking solution (2% bovine serum albumin fraction V (Sigma) in PBS added. Following a 30 min incubation at 37 C, the plates are washed three times with PBS, wrapped in plastic and stored at 4° C. until used. The binding of the peptides is monitored by ELISA using monoclonal antibodies specific for a control chimeric protein that are coated as Biotinylprotein-Strepavidin. A protein concentration of about 5 ug/ml in the coating buffer is optimal.

Sensitivity and Specificity

Peptide libraries were generated for each of the protein antigens described above consisting of 15-mer peptides overlapping by 10 amino acids. 8 serum samples from patients with culture confirmed Lyme disease that demonstrated seropositivity by western blot were used to screen the different peptide libraries. Four dilutions of antibody were incubated with the libraries using ProImmune's proprietary REVEAL epitope mapping system. Positive binding was reported for several peptides in each protein. Individual peptides were chosen for further analysis using three criteria:

1) their ability to bind at least 75% (⅝) of the serum samples,
2) their ability to bind to multiple (~50%) of the serum samples at multiple dilutions (indicating high affinity binding),
3) low sequence identity with other bacterial species as determined by sequence alignment using the NCBI protein BLAST algorithm on the NCBI website (we chose peptides unique to *Borrelia* species, and had less than a 50% sequence identity with peptides from other bacteria).

The peptides selected are listed in Table 1.

Figure 2:
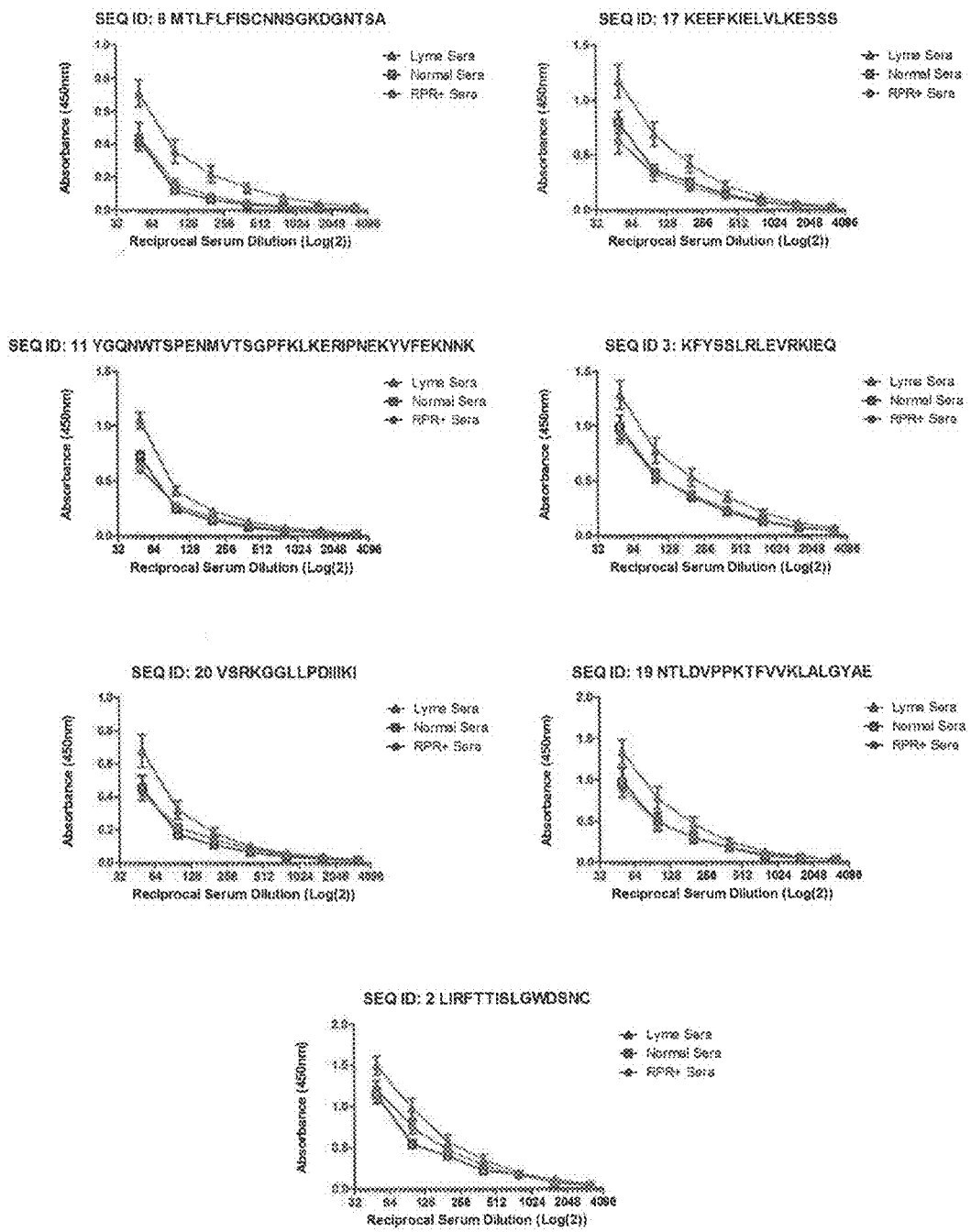
FIG. 2 shows representative data comparing the mean peptide binding ability of serum antibody from Lyme disease patients, healthy individuals (normal sera), or patients with Syphilis (RPR+ sera) at several different serum dilutions (n=10 patients/group). Data were generated using standard ELISA techniques and a goat anti-human IgG and IgM secondary antibody to detect serum antibody binding. Similar data have been generated for all peptides discussed in this application.
Figure 3:
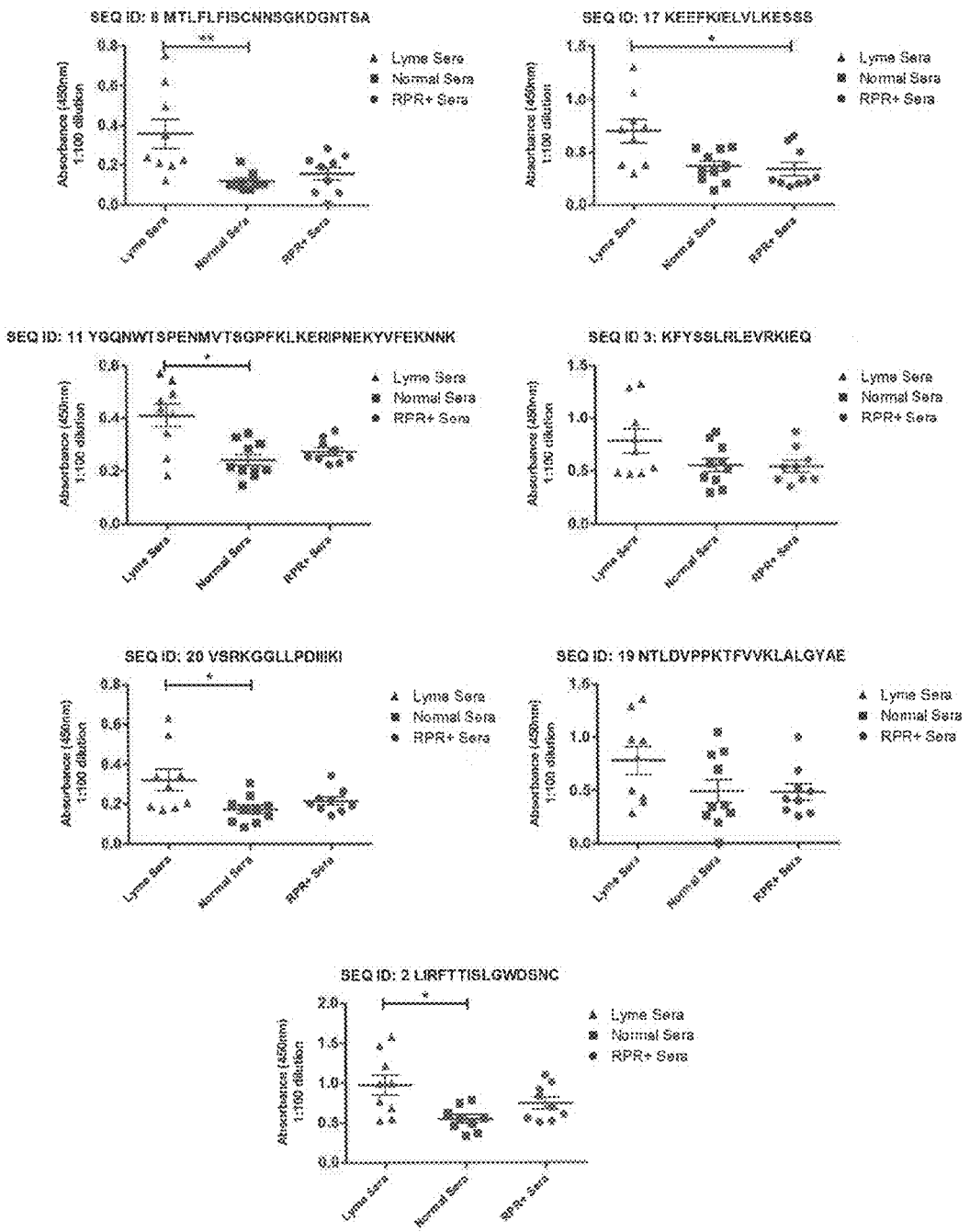
FIG. 3 shows representative data comparing the absorbance values generated by binding of antibody from individual patient sera at a single dilution (1:100). Data were generated using standard ELISA techniques and a goat anti-human IgG and IgM secondary antibody to detect serum antibody binding. Similar data have been generated for all peptides discussed in this application.
Figure 4:
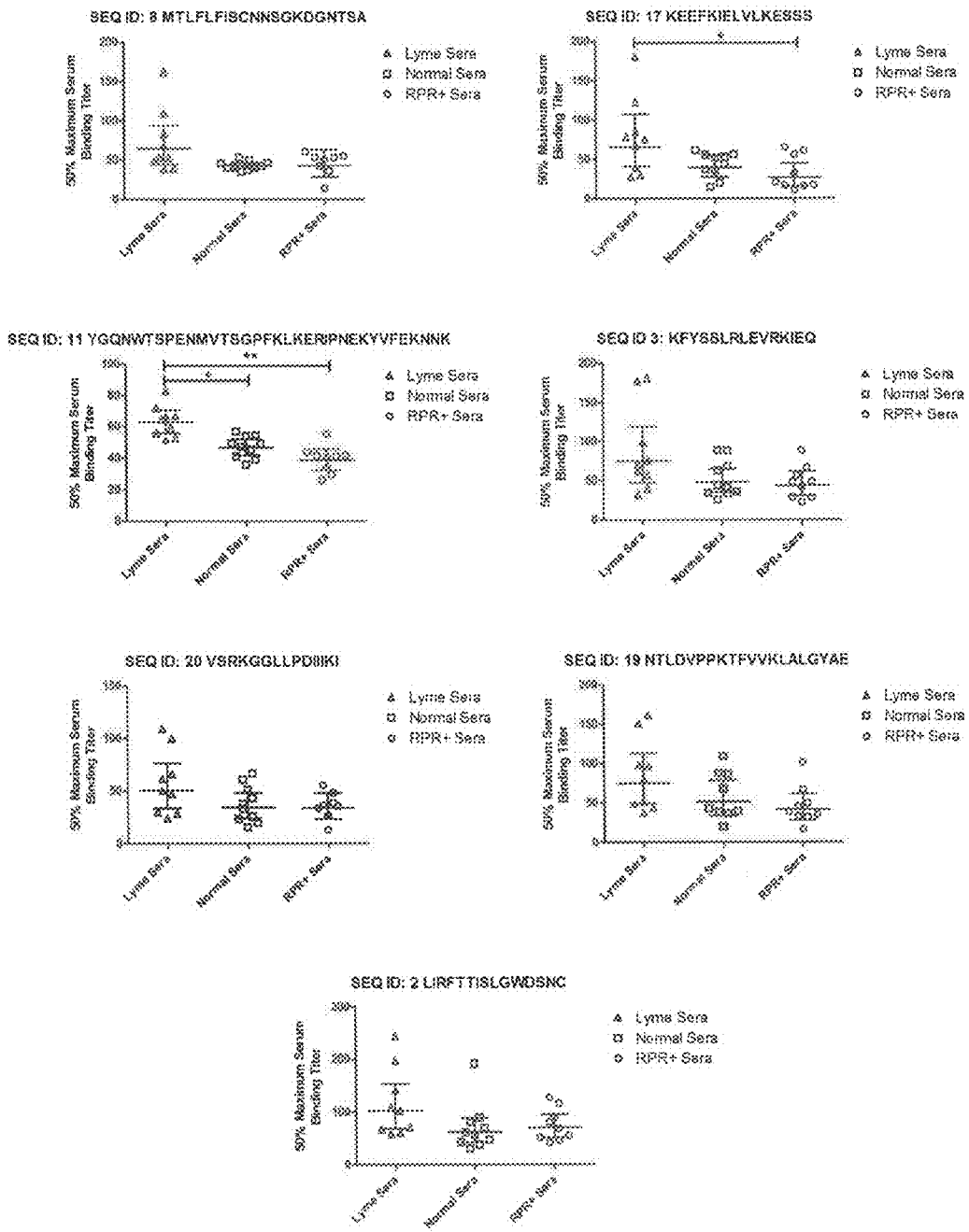
FIG. 4 shows representative data comparing the binding of antibody from individual patient sera at the 50% maximal serum binding titer, which is the serum dilution at which the absorbance of a particular binding curve (as depicted in the upper panel) reaches 50% of the maximal absorbance recorded for that curve. Data were generated using standard ELISA techniques and a goat anti-human IgG and IgM secondary antibody to detect serum antibody binding. Similar data have been generated for all peptides discussed in this application.

Each of these peptides was then further screened in an ELISA assay, using serum samples from nine patients with confirmed seropositivity for Lyme disease by western blot, ten healthy individuals with no history of Lyme disease (negative control), and nine patients with confirmed syphilis (RPR+, control for cross-reactivity), as described above. A sample was considered positive if a statistically significant difference in the mean binding of serum antibodies from patients with serologically confirmed Lyme disease was present compared to serum from patients confirmed to be sero-negative for Lyme disease (normal controls), and serum from patients that are positive for Syphilis (RPR+), where significance is measured as $p<0.05$ as determined using a Kruskal-Wallis test followed by a Dunn's comparison test. RPR+ serum is used as a negative control because it is a disease caused by a different Spirochete pathogen (*Treponema pallidum*) which may contain antigens that are cross-reactive with *Borrelia* infected patients. Serum antibody binding was compared at single dilutions (1:100), multiple dilutions (analysis of antibody binding curves), as well as reciprocal 50% binding titers (several dilutions of each serum sample were prepared and incubated with each peptide; the 50% binding titer was determined as the dilution of antibody at which the absorbance measured in the ELISA assay had reached 50% of the maximum absorbance recorded for any of the dilutions). Representative data for antibody binding is shown in FIGS. 1-4. FIG. 2 shows the serum antibody-binding curves for 7 potential peptide antigens, demonstrating increased binding of serum from Lyme disease patients at several dilutions of the serum samples compared to serum from patients with Syphillis (RPR+) or normal control sera. FIG. 3 shows the analysis of peptide binding at a single dilution, which is more representative of the data that would obtained in a clinical laboratory setting (statistically significant differences between groups are shown by the lines and asterisks, $*p<0.05$ and $p<0.01$). FIG. 4** is a different kind of analysis which assesses the binding of serum to peptides using 50% binding titers (the dilution at which the absorbance reaches 50% of the maximal absorbance recorded for any of the dilutions). The clearly demonstrate an enhanced binding of peptides in sera from patients with Lyme disease compared to syphilis patients and/or sera from normal individuals.

Similar data have been generated for all of the peptides shown in Table I.

Multipeptide Assays

The next step is to create a multi-peptide assay using different combinations of the peptides in Table 1. Various combinations of peptides, based upon their results in single ELISAs will be combined and screened using sera from early Lyme disease patients in whom disease has been confirmed by PCR, and comparing the binding efficacy to serum from normal healthy individuals with neither a known history of Lyme disease nor immunoblot patterns characteristic of the infection obtained from areas endemic and non-endemic for LD are used as negative healthy controls. Serum from patients with Syphilis, rheumatoid arthritis, systemic lupus erythematosus, and *Helicobacter pylori* infection will be used as negative controls for cross-reactivity with antibodies raised in response to other diseases (cross-reactivity controls). The use of multiple peptides in a single assay will increase the sensitivity of the assay for positive Lyme samples but not for the cross-reactivity controls and normal serum. A cutoff of 3SD above the mean of the control groups will be used as a marker of positively.

D. Evaluating the Ability of Peptides Containing Epitopes as Identified in Section C to Bind Anti-*B. burgdorferi* IgM and IgG Antibodies We will use serum and isolated IgG and IgM from patients with culture confirmed early LD to assess the diagnostic potential of the 21 peptides shown in Table 1. The peptide synthesis and ELISA methods that we will use are described in Example I. We expect that it is unlikely that only a single one of the peptides will provide sufficient sensitivity to identify individuals with antibodies to *B. burgdorferi* proteins. We plan to assess a variety of combinations of the epitope-containing peptides. We will use 50 serum samples from patients with culture confirmed early LD, 50 serum samples from patients with culture confirmed acute disseminated LD, 50 serum sample from patients with late LD, 50 serum from a bank of normal health patients from endemic and non endemic areas, and panels of serum from other tick borne and diseases that are in the differential diagnosis of LD. These latter panels will include serum from 20 patients with rheumatoid arthritis, 20 patients with SLE, 20 patients with syphilis, 20 patients with MS, 20 patients with *H. pylori*, 20 patients with culture confirmed HGE and 20 patients with microbiologically confirmed babesiosi.

E. Developing an Immunodiagnostic Peptide Assay

1. Selection of the Peptides:

The selection will be based on 1) additional tests of the sensitivity and specificity of each peptide (e.g. using sera from patients who have been infected with other organisms known to have cross-reactivity with *B. burgdorferi*); 2) the relative coating efficiency of each peptide combination (see below).

2. Preparation and Testing of Microwells Coated with Peptides.

We have found, unexpectedly, that the peptides of the invention are adsorbed to microwell surfaces quite well without the need for biotinylation and linking to streptavidin, and that the directly adsorbed peptides were as efficient as the streptavidin-conjugated antigens for ELISA detection of *B. burgdorferi* antibodies. The free peptides were not, however, well adsorbed on nitrocellulose surfaces for use in Fast Format (lateral flow) immunoassays. We found that direct biotinylation of synthetic peptides at the N-terminus during solid-phase synthesis was much more convenient than linking biotinyl groups to free peptides after deprotection and cleavage from the solid supports. Also, streptavidin conjugates of N-biotinylated peptides worked as well in the Rapid Format assays as did the peptides linked to streptavidin according to the published protocol (Liang et al. (1999a) (supra).

Since we will synthesize some small peptides encompassing single linear epitopes, in general all peptides will be synthesized with N-terminal biotinyl residues and streptavidin conjugates will be used for both ELISA and Rapid Format (membrane) assays. With the biotinyl groups attached during the solid phase synthesis, conjugation with streptavidin is hardly more complicated than coating plates with free peptides, and there will be no worry about poor adhesion of short peptides to the immobilizing surfaces. The peptides do not need to be immobilized in a specific ratio to one another, but enough of each peptide must be bound to ensure that none of the epitopes becomes limiting in ELISA assays of patient sera.

3. Comparison of Prototype Peptide Assay to Whole *B. burgdorferi* ELISA and Western Blot.

Once we have identified the best peptide combination(s), we will compare the prototype peptide assay to the standard CDC recommended protocol. The clinical samples will be run on a standard ELISA using whole low passage *B. burgdorferi* and on IgM and IgG western blots to compare the results of the peptide assay.

Positive Controls: Recombinant proteins OspC, FlaB, DbpA and peptides of IR6 will be used as controls. The reactivity of each of the peptides will be compared to the corresponding recombinant protein.

Negative Controls: To assess non-specific binding of antibodies in our peptide assay we will use a specifically designed random peptide. To assess non-specific binding of antibodies in our recombinant protein positive control assay we will use BSA.

Positive serum samples to be used to assess peptide preparations and comparative proteins:

a. 100 serum samples obtained at presentation from patients with culture confirmed early local LD.
b. 100 serum samples obtained at presentation from patients with culture confirmed acute disseminated LD.
c. 100 serum sample from patients with late LD.

Negative control serum samples to be used to assess peptide preparations and comparative proteins:

a. 50 sera from a bank of normal health patients from endemic areas.
b. 50 sera from a bank of normal health patients from non-endemic areas.
c. 30 sera samples from individual patients with culture confirmed HGE.
d. 20 sera samples from individual patients with microbiologically confirmed babesiosis.
e. 30 sera samples from individual patients with rheumatoid arthritis
f. 30 sera samples from individual patients with SLE.
g. 20 sera samples from individual patients with syphilis.
h. 20 sera samples from individual patients with MS.
i. 20 sera samples from individual patients with *H. pylori.*

It is expected that the peptides tested will provide a sensitive, specific assay which is at least as effective as the presently approved C6 assay.

F. Preparation and Characterization of Multi-Epitope Polypeptides

In order to significantly increase the sensitivity of peptide assays based on the individual peptides described herein, we will construct multimeric peptides (dimers, trimmers and more) containing various combinations of the 21 peptides shown in Table 1 or active variants thereof. Spacers of, for example, 3 glycines will be inserted between the epitopes in the multimer. Other diagnostic peptides described herein, or known to those of skill in the art, can also be combined with peptides of the invention in multimers.

We will use the panel of 8 well defined clinically characterized and culture positive Lyme disease sera that were previously tested by ELISA: two low, two medium and two high titer from six different Lyme patients, in addition to one negative control obtained from an healthy individual.

It is expected that some combinations of the peptides of the present invention will exhibit increased sensitivity compared to the individual peptides.

Example II—a Diagnostic OspC Peptide for Lyme Disease

OspC is a *Borrelia* surface protein required for transmission of the bacteria from the midgut of tick into the human host (Tilly et al. (2006) *Infection and Immunity* 74, 3554-3564). It is a protein of significant diagnostic value because it is required for entry into the mammalian host, and therefore, will always present during infection and is expressed during the initiation of infection. However, the OspC protein is not highly conserved, containing numerous subtypes that have significant sequence variability. Furthermore, some previous studies using whole recombinant OspC as a serodiagnostic for Lyme disease demonstrated a high level of cross-reactivity within negative disease control samples.

In the present study we mapped linear epitopes within the OspC protein to identify highly-conserved regions lacking cross-reactivity with antigens from other bacteria, and have generated an antigenic peptide (OspC1) that binds to antibody from early Lyme disease patients with high specificity. OspC1 outperformed a previously identified peptide antigen from OspC (PepC10) in an ELISA-based immunoassay, and is a useful target for inclusion into a sensitive multi-peptide serological assay for the diagnosis of early Lyme disease.

Using an overlapping peptide library, we mapped linear epitopes in OspC, an important virulence factor of *B. burgdorferi* required for mammalian infection, and confirmed the results by ELISA. We identified a highly conserved 20-amino acid peptide epitope, OspC1. Via ELISA, OspC1 detected specific IgM and/or IgG in 60 out of 98 serum samples (62.1%) obtained from patients with erythema migrans (early Lyme disease) at the time of their initial presentation. By comparison, the commercially available OspC peptide, PepC10, detected antibody in only 48 of 98 serum samples (49.0%). In addition, OspC1 generated fewer false positive results among negative healthy and disease (rheumatoid arthritis and syphilis) control populations compared to PepC10. Both highly specific and more sensitive than currently available OspC peptides, OspC1 will have value as a component of a multi-peptide Lyme disease serological assay with significantly improved capabilities for the diagnosis of early infection.

Advantages of the OspC peptides discussed in this Example, as well as other peptides discussed throughout this application, include that they bind well to both IgG and IgM, and are derived from antigens that are expressed early after infection.

A. Material and Methods

Serum:

98 serum samples (Table 3) were obtained with consent, under IRB institutional approval, from patients with erythema migrans at their initial presentation to the Lyme disease clinic at Westchester Medical Center in Westchester, N.Y. (n=48) or Gundersen-Lutheran Medical Center in La Crosse, Wis. (n=50). Both areas are highly endemic for Lyme disease. 48 sera from healthy individuals residing in a non-endemic region for Lyme disease (New Mexico) were purchased from Creative Testing Solutions (Tempe, Ariz.). 88 negative disease control sera obtained from patients with either Rheumatoid arthritis (RA) (n=48) or syphilis (n=40) were purchased from Bioreclamation, LLC (Westbury, N.Y.); these sera were obtained from a region highly-endemic for Lyme disease (southern New York State).

Peptides:

Epitope mapping was performed by ProImmune, Inc. (Oxford, UK) using their proprietary ProArray Ultra™ peptide microarray technology. In brief, overlapping peptide libraries generated from the sequence for OspC type K (accession # AAB86554), and consisting of 15-mer peptides overlapping by 10 AA, were exposed to multiple dilutions of eight individual sera containing antibodies against *B. burgdorferi* sensu stricto, as determined by western blot (Gold Standard Diagnostics, Davis, Calif.). Positive binding of serum was detected using a fluorochrome-labeled anti-human secondary antibody and the data were reported as dimensionless units of the average fluorescence signal intensity (FSI) for replicate spots of each peptide. A positive signal was required to be at least 4× the FSI of the negative assay control. Peptides chosen for further analysis were produced by Lifetein, Inc. (South Plainfield, N.J.), and were a minimum of 90% purity. Sequence alignment of different OspC types was performed using CLC Workbench (FIG. 6). Sequences for the OspC types had been identified previously. When a complete sequence was not available for an OspC type multiple sequences for that type were presented showing the presence or absence of the peptide of interest.

ELISA:

96-well Maxisorp (Nunc, Rochester, N.Y.) plates were coated with 10 μg/ml of each peptide in 0.1 M sodium carbonate buffer, pH 9.4 for 1 h at room temperature. After 1 h, 1% BSA in PBS was added to each well and incubated overnight at 4° C. The next morning plates were washed 3× with 0.05% Tween-20 in PBS using an automated plate washer (Molecular Devices, Sunnyvale, Calif.). Serum samples diluted 1:100 in 1% BSA were added in triplicate and incubated at room temperature for 2 h. The plates were washed again and HRP-labeled goat anti-human IgM (μ-chain specific) or HRP-labeled goat anti-human IgG (γ-chain specific) (Southern Biotech, Birmingham, Ala.) diluted 1:5000 in blocking buffer was added to each well for 1 h at room temperature. The plates were washed and developed with TMB substrate (KPL, Gaithersburg, Md.) for 30 min at room temperature. The reaction was stopped by addition of 2N sulfuric acid, and absorbance was read at 450 nm and 570 nm (Molecular Devices).

Data Analysis:

The sensitivity and specificity of each peptide was determined for both IgM and IgG by comparing results from Lyme patients with results from negative controls via ROC analysis using Prism 6.0 (Graphpad, La Jolla, Calif.). Cut-off values used for comparing sensitivity and specificity between the two peptides were 3 SD from the mean of healthy controls as the cut-off (limit of detection). Statistical analysis of categorical data presented in tables and the text was performed using a Fisher's exact test with a two-tailed p value using Prism 6.0 (Graphpad).

Figure 5:
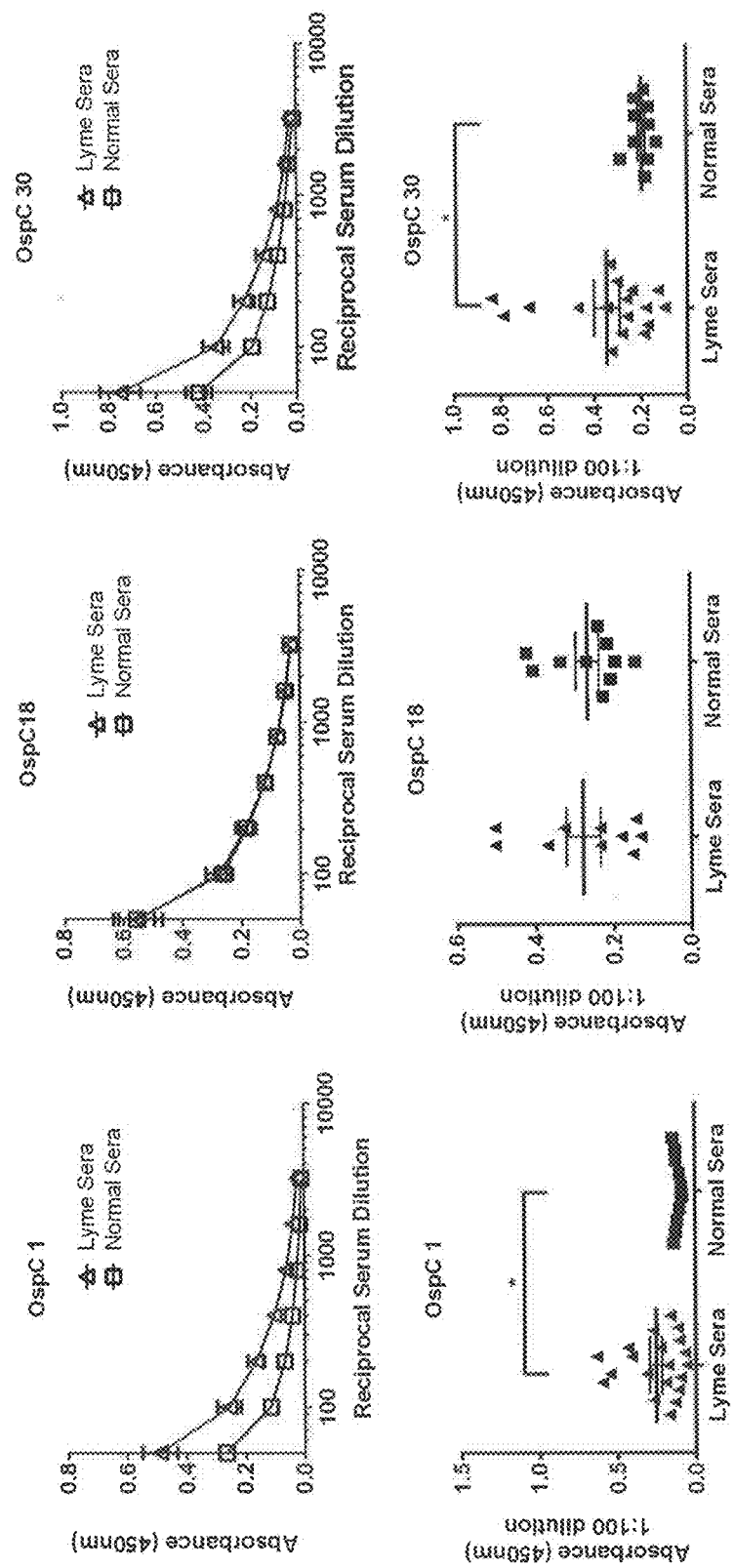
FIG. 5 shows IgG and IgM antibodies specific for OspC peptides in serum from patients with Lyme disease. Serum from patients with Lyme disease was confirmed to be positive for anti-*Borrelia* antibodies using commercially available western blot strips prior to incubation with OspC peptides (10 μg/ml) in an ELISA. Antibody binding was detected using a polyclonal HRP-labeled goat anti-human IgG and IgM (ɣ and μ chain specific) antibody. Upper panels show a dose titration of Lyme disease patient sera (n=10) and healthy control serum (normal sera, n=10) on OspC-peptide coated 96-well plates. Data are reported as mean absorbance ±SD. Lower panels depict binding of serum from Lyme disease patients and healthy controls (normal sera) at a single dilution of 1:100. Data are reported as absorbance at 450 nm-570 nm, the line represents mean±SD. OspC 1 (Lyme n=20, normal n=10), OspC 18 (Lyme n=20 and normal n=10), OspC 30 (Lyme n=17, normal n=10). Upper and lower panels are different experiments, performed on different days, with different patient samples. *p<0.05 by Mann-Whitney test.

B. Results Eight serum samples from Lyme disease patients were chosen for the initial epitope mapping based upon a high titer of anti-*Borrelia* antibodies as determined by the detection of 9-10 out of 10 bands on a commercially available Lyme disease diagnostic western blot strip test (5 of 10 bands is the minimum requirement for a sample to be considered positive). Epitope mapping was performed by ProImmune, Inc. using their proprietary ProArray Ultra™ peptide microarray technology. A partial sequence for OspC type K (*B. burgdorferi* OC12, accession # AAB86554) was expressed as an overlapping peptide library consisting of a total of 37 peptides (Table II), each 15 amino acids (AA) in length overlapping by 10AA (offset by 5AA). OspC type K was used for the epitope mapping because it has been associated with disseminated disease (29). In addition to lacking the first 10AA, the partial sequence does not contain the final 10 AA, which correspond to the commercially available OspC peptide, PepC10. Of the 37 peptides assessed, only 3 were observed to bind more than 50% of the eight serum samples used in the epitope mapping. These were peptide 1, peptide 18, and peptide 30; in addition, 3 of 5 samples that bound peptide 1 also bound peptide 2 indicating that the epitope found in peptide 1 might extended into peptide 2. Herein these peptides will be referred to as OspC1 (peptide 1+2, MTLFLFISCNNSGKDGNTSA (SEQ ID NO:8, sometimes referred to herein as OspC-typeK (11-30)), OspC18 (peptide 18, TLLAGAYTISKLITQ (SEQ ID NO 51)), and OspC30 (peptide 30, AKKAILIT-DAAKDKG (SEQ ID NO:9, sometimes referred to herein as the OspC-typeK (146-160)). Serum binding was confirmed in a subsequent ELISA where the 3 peptides were incubated with an additional 18 sera from high titer Lyme disease patients (8-10 of 10 bands on western blot strip assay), and 10 negative sera from healthy individuals. Sera were titrated on peptide coated plates to determine an optimal dilution for further study. OspC18 bound serum antibodies from Lyme patients and normal individuals equivalently (FIG. 5), indicating that the epitope contained in the peptide was cross-reactive and not specific for *Borrelia*. OspC 18 was not used in further analyses. The mean absorbance of serum antibody binding to both OspC1 and OspC30 was significantly higher in Lyme disease patients compared to normal individuals; however, OspC1 appeared to detect more individual Lyme samples than did OspC30 (FIG. 5).

TABLE 3

Borrelia burgdorferi OC12 OspC (type K)[a]

| Peptide # | Pos. in Protein Sequence | Peptide Sequence |
|---|---|---|
| 1 | 11-25 | MTLFLFISCNNSGKD |
| 2 | 16-30 | FISCNNSGKDGNTSA |
| 3 | 21-35 | NSGKDGNTSANSADE |
| 4 | 26-40 | GNTSANSADESVKGP |
| 5 | 31-45 | NSADESVKGPNLTEI |
| 6 | 26-50 | SCKGPNLTEISKKIT |
| 7 | 41-55 | NLTEISKKITESNAV |
| 8 | 46-60 | SKKITESNAVVLAVK |
| 9 | 51-65 | ESNAVVLAVKEIETL |
| 10 | 56-70 | VLAVKEIETLLASID |
| 11 | 61-75 | EIETLLASIDELATK |
| 12 | 66-80 | LASIDELATKAIGKK |
| 13 | 71-85 | ELATKAIGKKIQQNG |
| 14 | 76-90 | AIGKKIQQNGGLAVE |
| 15 | 81-95 | IQQNGGLAVEAGHNG |
| 16 | 86-100 | GLAVEAGHNGTLLAG |
| 17 | 91-105 | AGHNGTLLAGAYTIS |
| 18 | 96-110 | TLLAGAYTISKLITQ |
| 19 | 101-115 | AYTISKLITQKLDGL |
| 20 | 106-120 | KLITQKLDGLKNSEK |
| 21 | 111-125 | KLDGLKNSEKLKEKI |
| 22 | 116-130 | KNSEKLKEKIENAKK |
| 23 | 121-135 | LKEKIENAKKCSEDF |
| 24 | 126-140 | ENAKKCSEDFTKKLE |
| 25 | 131-145 | CSEDFTKKLEGEHAQ |
| 26 | 136-150 | TKKLEGEHAQLGIEN |
| 27 | 141-155 | GEHAQLGIENVTDEN |
| 28 | 146-160 | LGIENVTDENAKKAI |
| 29 | 151-165 | VTDENAKKAILITDA |
| 30 | 156-170 | AKKAILITDAAKDKG |
| 31 | 161-175 | LITDAAKDKGAAELE |
| 32 | 166-180 | AKDKGAAELEKLFKA |
| 33 | 171-185 | AAELEKLFKAVENLA |
| 34 | 176-190 | KLFKAVENLAKAAKE |
| 35 | 181-195 | VENLAKAAKEMLANS |
| 36 | 186-200 | KAAKEMLANSVKELT |
| 37 | 190-204 | EMLANSVKELTSPIV |

[a]Partial Sequence; Accession #AAB86554

The sequences in this Table, in the order of peptide 1-peptide 37, are represented by, respectively SEQ ID NOS: 80, 78, 263-277, 51, 278-288, 9 and 289-295.

A limitation in the use of OspC in a diagnostic assay is the inherent variability found within the protein. Many OspC 'types' (allelic variants) have been described in the literature (14, 27, 28), some having been associated with a greater propensity for dissemination of the bacteria from the site of initial infection following the tick bite. While the association of OspC type and disseminated disease is beyond the scope of this study, to be effective within the constraints of a diagnostic assay, an epitope must be highly conserved. Thus, we aligned the sequences of 15 different OspC types, assessing the AA variability in the epitopes OspC1 and OspC30 and comparing it to the degree of sequence variability found within the commercially available PepC10 sequence (PVVAESPKKP (SEQ ID NO36)). Complete single sequences were not available for OspC types C, G, H, J, K, M, and U; when possible, multiple different sequences from the same OspC type were aligned to demonstrate the presence or absence of each epitope. As demonstrated in FIG. 6, the sequence for OspC1 is both present and highly conserved in all of OspC types analyzed, being identical to the consensus sequence generated by alignment of the different OspC proteins. This is similar to PepC10 which is also highly conserved and identical to the aligned consensus sequence, though this peptide does appear to be absent in OspC type U and type J. Complete sequences containing the c-terminal portion (where PepC10 is located) of OspC type C, and type G were not available, so it is unclear if PepC10 is fully present in those types. On the other hand, OspC30 is poorly conserved among the different OspC types; the sequence identified in the epitope mapping was highly divergent from the consensus sequence generated by alignment of that position within the different OspC types. Indeed, a subsequent epitope mapping of OspC type A did not identify the analogous region for OspC 30 as an epitope (data not shown). The high degree of conservation in both OspC1 and PepC10 may be due to their placement, respectively, in the N-terminal and C-terminal portions of the protein, as the highest degree of variation among the different OspC types falls in the middle of the protein. OspC 30 was not used in further analyses.

Figure 7:
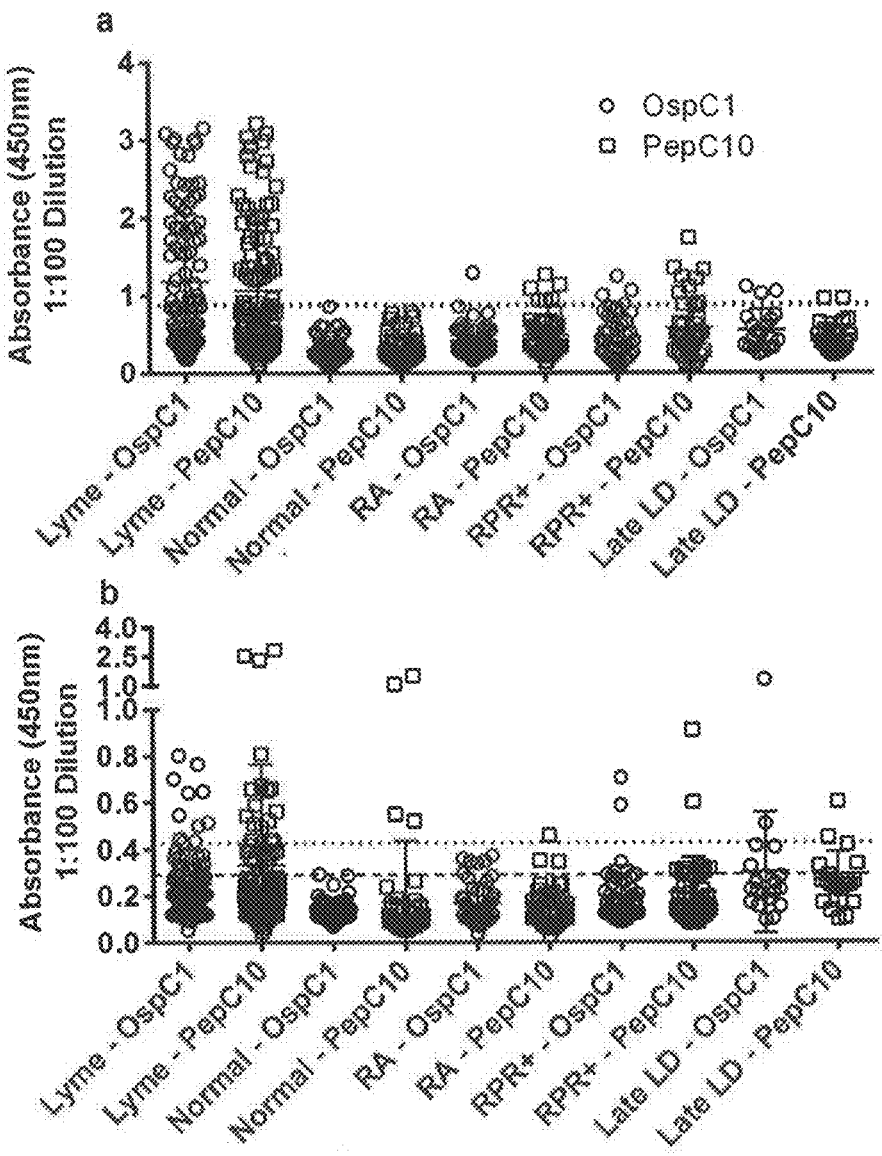
FIG. 7 shows a comparison of OspC1 and PepC10 in the detection of IgM and IgG antibodies in serum from patients with early Lyme disease. Serum from patients with early Lyme disease (erythema migrans+), healthy controls, patients with rheumatoid arthritis (RA), or patients with syphilis (RPR+) were incubated on OspC1 or PepC10 coated (10 μg/ml) plates in an ELISA. Serum IgM (a) and IgG (b) was detected using HRP-labeled goat anti-μ or anti-ɣ chain antibodies, respectively. The dashed line represents 3SD from the mean of healthy controls incubated with OspC1; the dotted line represents 3SD from the mean of healthy controls incubated with PepC10. The lines overlap in a. Data are reported as absorbance at 450 nm-570 nm. Lyme (n=98), Normal (n=48), RA (n=48), Syphilis (n=39).

To assess the potential of OspC1 in a diagnostic assay for early Lyme disease, we screened the peptide against a large panel of serum obtained from patients with EM at the time of their initial diagnosis, and compared the results to those obtained with PepC10. As EM develops anywhere from 3 to 30 days after tick bite (with the average being 7 days), the level of anti-Borrelia antibody within this patient population can vary greatly. Early disease is marked by elevated IgM antibodies against Borellia. As the disease progresses, and the immune response evolves, the IgM response diminishes and is replaced with IgG. Dependent upon when a patient seeks medical attention they may present with IgM, IgG or a mixture of both. As a result we independently assayed for IgM and IgG against OspC1 and PepC10 (FIG. 7). Sera from healthy individuals collected in a non-endemic region for Lyme disease (the American southwest) were used as a negative control and to set the limits of detection. In addition, sera from patients with RA or syphilis were used as negative disease controls in this assay. RA is an autoimmune inflammatory disease marked by elevated serum antibody levels and joint destruction, which can also occur in Lyme disease. Syphilis is an infectious disease caused by the related spirochete Treponema pallidum, and was used as a negative control for cross-reactive antibody generated by infection with a related spirochete. Serum from 48 healthy donors was used to establish the limits of detection for the ELISA. The mean absorbance for OspC1 binding of IgM (0.316±0.187) and IgG (0.139±0.051) and PepC10 binding of IgM (0.335±0.187) and IgG (0.125±0.101) was determined. Samples were considered positive if the mean absorbance of three replicate wells was greater than 3SD from the mean of the healthy controls, equivocal if it was between 2SD and 3SD from the mean of healthy controls, or negative if it was less than 2SD from the mean of the healthy controls. Two of 48 samples in the PepC10 healthy control population bound to IgG with absorbance values more than 3SD from the mean of the population. These samples were treated as outliers, and while not removed from the analysis, they were not included in the calculation of cutoff values. These samples were not positive for IgM binding to PepC10 or binding of either isotype to OspC1, and were subsequently treated as bonafide false positives. All false positive control samples were evaluated with commercially available Lyme disease diagnostic western blot strip tests to determine if the serum was obtained from an individual with previously undiagnosed Lyme disease. All negative controls included in this evaluation were negative for Lyme via western blot strips.

Positive binding of serum IgM to OspC1 was detected in nearly half (47 of 97) of early Lyme disease patient sera (FIG. 6a, Table 4), while significantly fewer sera positive for IgG (24 of 98) were found (FIG. 6b, Table 4, p=0.006). This was expected, as IgM is the predominant antibody isotype found during early infection. However, some of the samples were only positive for either IgM or IgG; the total number of patient sera considered unequivocally positive (detecting either serum IgM or IgG) for Lyme disease via binding of OspC1 was greater than 60% (60 of 98, 62.9%) (Table 5). If samples found to be equivocal were included in that rate, OspC1 positively detected Lyme disease more than 75% of the time (75 of 98, 76.5%, Table 5, positive+equivocal). By comparison, PepC10 positively detected serum IgM antibodies in fewer early Lyme patient serum samples compared to OspC1 (40 of 97 vs. 47 of 97, respectively, no significant difference (NS)) (Table 4), and also had a higher rate of false positives for IgM binding within negative disease control populations (Table 4). As with OspC1, PepC10 detected significantly fewer IgG positive sera compared to IgM (16 of 98 vs. 40 of 97, respectively, p<0.001), but detected a lower number of IgG positive early Lyme patient sera compared to OspC1 (16 of 98 vs. 24 of 98, respectively, NS). Fewer total positive sera (either IgM or IgG) were detected by PepC10 (48 of 98, 49.0%) compared to OspC1 (60 of 98, 62.9%, Table 5, NS). This difference was maintained when the number of equivocal samples was included in the rate (OspC1-75 of 98, 76.5% vs. PepC10-64 of 98, 65.3%, NS). OspC1 detected an apparently higher number of IgG false positives within the negative disease control patient population (Table 4). However, PepC10 demonstrated more variability in serum IgG binding within the negative healthy control population compared to OspC1, (PepC10=0.125±0.100, CV=0.80 vs. OspC1=0.139±0.049, CV=0.35, mean±SD, coefficient of variation), with the detection of 4 false positives within the normal control sera incubated with PepC10 compared to no false positives in the normal control sera incubated with OspC1 (FIG. 7b). This resulted in incrementally higher cut-off values for the detection of IgG antibodies compared to OspC1 as a result of larger SD values (FIG. 7b), which in turn resulted in lower rates of both true and false positive. Thus, counterintuitively, the higher degree of nonspecificity demonstrated by PepC10 following incubation with normal control serum resulted in the detection of fewer false positives in other negative control populations.

TABLE 5

Composite recognition of OspC1 and PepC10 by serum antibody[a]

|  | Lyme | | Normal |
|---|---|---|---|
|  | OspC1 | PepC10 | OspC1 |
| Positive[b] | 62.1% | 49.0% | 2.0% |
|  | (60/98) | (48/98) | (1/48) |
| Equivocal[c] | 15.3% | 16.3% | 6.3% |
|  | (15/98) | (16/98) | (3/48) |
| Negative[d] | 23.5% | 34.7% | 92.7% |
|  | (23/98) | (34/98) | (44/48) |

[a]Total number of serum samples containing either IgM or IgG antibody binding to OspC1 or PepC10
[b]More than 3 SD from mean of healthy controls
[c]Between 2 SD and 3 SD from mean of healthy controls
[d]Less than 2 SD from the mean of the health controls

TABLE 4

OspC1 and PepC10 serum IgM and IgG binding

|  |  | Lyme | | Healthy | | RA | | Syphillis | |
|---|---|---|---|---|---|---|---|---|---|
|  |  | OspC1 | PepC10 | OspC1 | PepC10 | OspC1 | PepC10 | OspC1 | PepC10 |
| IgM | Positive[a] | 48.5% | 41.2% | 0% | 0% | 2.0% | 12.5% | 10.3% | 20.5% |
|  |  | (47/97) | (40/97) | (0/48) | (0/48) | (1/48) | (6/48) | (4/39) | (8/39) |
|  | Equivocal[b] | 8.2% | 13.4% | 2% | 6.2% | 6.2% | 2.0% | 12.8% | 7.7% |
|  |  | (8/97) | (13/97) | (1/48) | (3/48) | (3/48) | (1/48) | (5/39) | (3/39) |
|  | Negative[c] | 43.3% | 45.4% | 98% | 93.8% | 91.8% | 85.5% | 76.9% | 71.8% |
|  |  | (42/97) | (44/97) | (47/48) | (45/48) | (44/48) | (41/48) | (30/39) | (28/39) |
| IgG | Positive[a] | 24.5% | 16.3% | 2.0% | 8.3% | 12.5% | 2.0% | 7.7% | 5.1% |
|  |  | (24/98) | (16/98) | (1/48) | (4/48) | (6/48) | (1/48) | (3/39) | (2/39) |
|  | Equivocal[b] | 16.3% | 11.2% | 4.2% | 0% | 6.2% | 4.2% | 17.9% | 0% |
|  |  | (16/98) | (11/98) | (2/48) | (0/48) | (3/48) | (2/48) | (7/39) | (0/39) |
|  | Negative[c] | 59.2% | 72.5% | 93.8% | 91.7% | 81.3% | 93.8% | 74.4% | 94.9% |
|  |  | (58/98) | (71/98) | (45/48) | (44/48) | (39/48) | (45/48) | (29/39) | (37/39) |

[a]More than 3 SD from mean of healthy controls
[b]Between 2 SD and 3 SD from mean of healthy controls
[c]Less than 2 SD from the mean of the health controls The sensitivity and specificity of both peptides for identifying positive samples was determined by ROC analysis using 3SD from the mean of healthy controls as a cut-off. When comparing detection of Lyme disease in patient sera to healthy controls, OspC1 demonstrated a specificity of 100.00% and sensitivity of 41.24% for IgM detection and a specificity of 97.92% and sensitivity of 24.92% for IgG detection. This is compared to PepC10 which demonstrated a specificity/sensitivity of 100.00% and 29.90% for IgM, and 91.67% and 17.35% for IgG, respectively. Thus, both peptides were highly specific for the detection of Lyme disease, indicating that when a positive value is returned it is highly likely that it is a true positive. When these values were recalculated comparing Lyme patient sera with all negative controls, OspC1 demonstrated a specificity/sensitivity of 98.52% and 41.24% for IgM and 92.59% and 24.49% for IgG, respectively. In comparison PepC10 demonstrated a sensitivity/specificity of 99.26% and 29.90% for IgM and 94.81% and 17.35% for IgG, respectively. Thus, with respect to both healthy and disease controls, both peptides are highly specific. However, OspC1 had a marginally higher sensitivity than PepC10 (41.24% vs. 29.90% for IgM and 24.49% vs. 17.35% for IgG). Overall, the area under the curve (AUC) for both peptides was similar (OspC1 vs. PepC10 IgM, 0.8047 vs. 0.7406 and OspC 1 vs. PepC10 IgG, 0.7296 vs. 0.7573).

As a target for a serological diagnostic assay, OspC1 has a number of desirable attributes: it is derived from a principal virulence factor that is required for mammalian infection, it is expressed very early in infection increasing the likelihood of an immune response being mounted against it, it is highly conserved among different OspC genotypes, and it identified a significant majority of patients with early disease. We submit that OspC1 is a viable candidate for testing in a multi-peptide diagnostic assay. An assay containing 5 or more specific peptide antigens, derived from multiple B. burgdorferi proteins, would markedly improve upon currently available technologies in both specificity and sensitivity (25), and represent a viable standalone laboratory test for all phases of Lyme disease diagnosis, especially early disease.

Example III—a Diagnostic OppA Peptide for Lyme Disease

OppA-2, a member of the oligopeptide permease (Opp) family of peptide transporters, is highly conserved among B. burgdorferi subspecies and is expressed early in the course of infection in the mammalian host, suggesting it can have utility as a diagnostic target. Using an overlapping peptide library, we mapped linear epitopes in OppA2 and identified 9 sequences for subsequent analysis. Two of peptides generated using these sequences, OppA2 (191-225) and OppA2 (381-400), bound antibody in Lyme disease patient sera with sufficient sensitivity and specificity to indicate that they can be useful components of a multi-peptide Lyme disease serological assay. Importantly, these peptides also demonstrated potential to function as diagnostic markers that distinguish between disseminating and localized B. burgdorferi infections.

Ideally, Lyme disease should be diagnosed early, when treatment is most effective at preventing disease progression. In the 1980 and early 1990's there was some question that there was a delay in the antibody response but it is now recognized that the development of the immune response to B. burgdorferi follows similar kinetics to the response to other bacterial infections: within one to two weeks after the onset of infection, IgM antibodies to B. burgdorferi can be detected in most infected individuals [5,18]. Yet, despite the development of a timely antibody response, current diagnostics are insensitive in early infection. The early immune response to B. burgdorferi is limited to a few antigens but they offer attractive targets for the development of improved serodiagnostic tests. Studies have identified very early antibody responses to FlaB, p66, RecA and to OppA-1, -2 and -4 [19,24 Brissette 2010]. Antibodies to OspC (25 kd), VlsE, BBK32, FlaA (37 kd), BmpA (39 kd), FliL, BBG33, LA7 and DbpA proteins appear slightly later [8], [13,14,18-24].

In this study, we mapped the linear B-cell epitopes of OppA2, an attractive target antigen and identified nine immunodominant epitopes. Assessing the serodiagnostic potential of peptides comprising each of the identified epitopes, we found 2 that are specific and sensitive markers for Lyme disease. The 2 peptides containing these epitopes can be components of a multipeptide based assay.

A. Materials and Methods

Materials and methods were similar to those described for Examples I and II. More particularly, Human Subjects.

Blood was collected from adult volunteers according to protocols approved by the Institutional Review Boards of the respective institutions. A total of 103 sera or plasma samples were obtained from patients presenting with EM at the time of their initial visit. Samples were from 3 different sites: the Gunderson Lutheran Medical Center in LaCross, Wis. (n=48, generously provided by Dr. Steve Callister); the Lyme Disease Diagnostic Center of New York Medical College, Valhala, N.Y. (n=31); and the State University of New York-Stony Brook (n=24). All of the 31 patients from New York Medical College had B. burgdorferi isolated by culture from skin biopsy of the skin lesion (n=16) or from blood (n=15). Sera from healthy volunteers residing in areas of the United States not endemic for Lyme disease (n=45) purchased from Creative Testing Solutions (Tempe, Ariz.) were used as negative controls. Sera from patients with a positive rapid plasma regain test (n=30) or diagnosed with rheumatoid arthritis (n=30) were purchased from (Bioreclamation, LLC). Samples were aliquoted and stored at −80° C.

Epitope Mapping of OppA2.

Epitope mapping was performed using overlapping peptide libraries encompassing the full-length B. burgdorferi B31, OppA2. One library consisted of peptides 15 amino acids in length overlapping by 10 AA (offset by 5 AA), 104 peptides in total, was synthesized by ProImmune, Inc (Oxford, UK), The epitope mapping was performed using ProImmune, Inc's proprietary ProArray Ultra™ peptide microarray technology. Sera from eight LD patients known to contain anti-Borrelia antibodies, 4? with early disseminated and 4? with late Lyme disease, were used to probe the peptide library. Another peptide library consisted of 20 AA peptides overlapping by 15 AA (offset by 5 AA) was produced by generated by ArrayIt (California). This library was screened using a similar panel of Lyme disease patient sera to that use to screen the ProImmune, Inc library. The 2 serum panels contained different sets of serum.

Peptide Synthesis.

Peptides encompassing sequences were identified for further analysis. Peptides OppA2 (11-25), OppA2 (191-225), OppA2 (276-290), OppA2 (276-300), OppA2 (286-300), OppA2 (286-310), OppA2 (381-400), OppA2 (356-375) and OppA2 (491-505) were synthesized by Lifetein, Inc. (South Plainfield, N.J.).

Peptide ELISA.

96-well plates (Nunc Maxisorp) were coated with 10 μg/mL peptide, diluted in 0.1M carbonate-bicarbonate buffer, pH 9.4 (50 μL per well), for 1 hour at room temperature. Blocking buffer 1% bovine serum albumin (BSA) in PBS was added to the wells (250 μL/well) and incubated overnight at 4° C. Wells were washed three times with PBS containing 0.05% Tween 20 (PBS-T) and incubated for 2 hours at room temperature with human samples diluted 1:100 in PBS-1% BSA. Each plate included samples from patients and healthy donors, and all samples were assayed in triplicate. After washing, wells were incubated for 1 hour at RT with a 1:15,000 dilution of HRP-conjugated secondary antibody against human IgG+IgM. Reactions were developed for 30 minutes with 3,3',5,5'-tetramethylbenzidine (TMB) in the dark at room temperature and the reaction was stopped by the addition of 2N H2SO4. Optical densities were determined at 450 nm and 570 nm wavelengths using a SpectraMax Plus plate reader (Molecular Devices). The cutoff for seropositivity was defined as the mean optical density (OD) of the healthy control samples plus two standard deviations (SD).

BLAST sequence comparisons were performed as described elsewhere herein.

Statistical Analysis.

The statistical significance of the quantitative differences between sample groups was determined by One-way ANOVA followed by a Tukey's Multiple Comparison Test, performed with GraphPad Prism software (San Diego, Calif.). A p value of less than 0.05 was considered statistically significant.

B. Results

Figure 8:
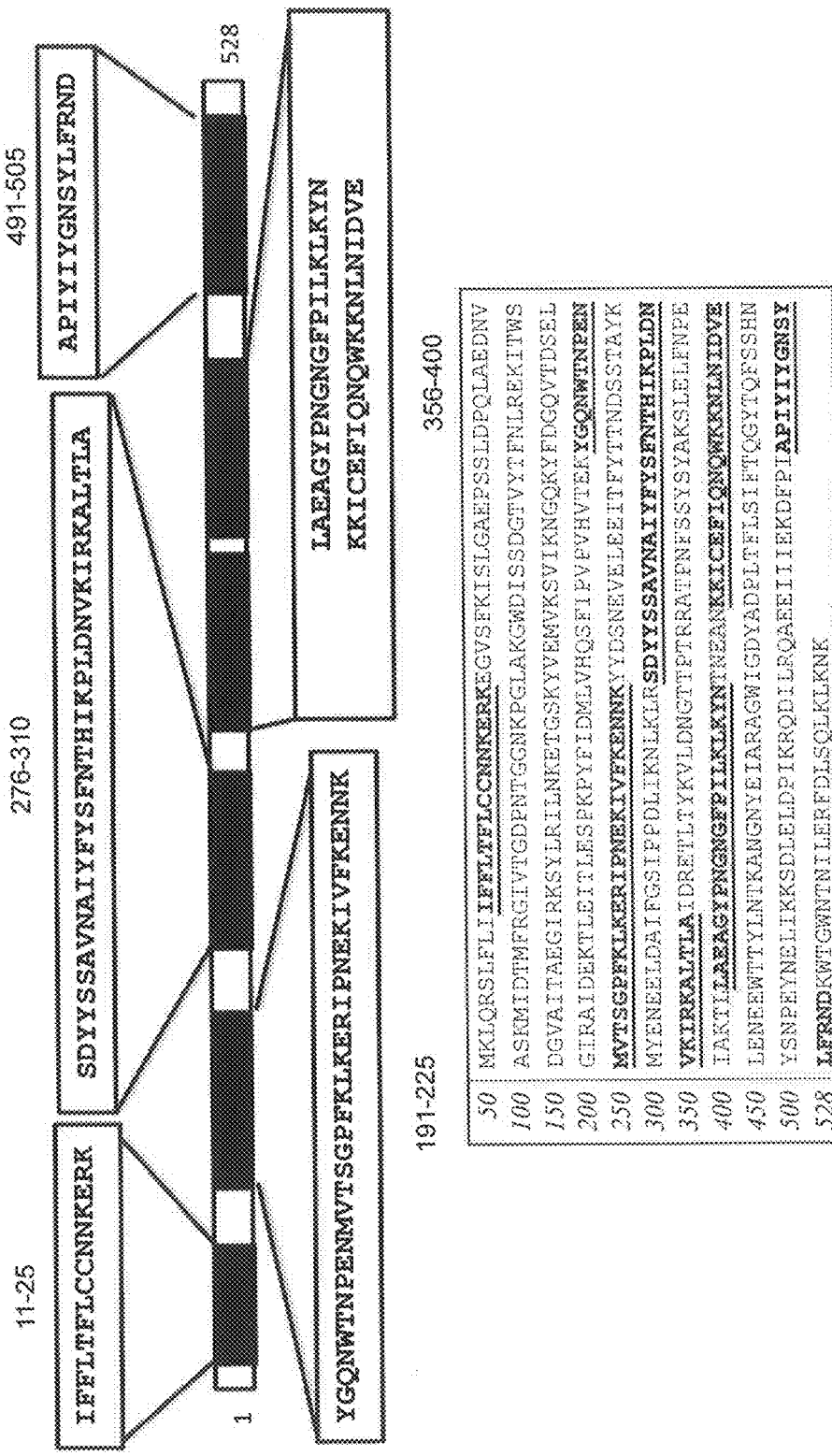
FIG. 8 shows antigenic regions and peptide sequences on the full-length sequence of OppA-2. The individual peptides, in the order of appearance from left to right, are represented, respectively, as SEQ ID NOS:10, 215, 53, 260, 47, 45 and 216.

Identification of immunogenic epitopes of OppA2. The results of the 2 different epitope mapping studies were reviewed independently. OppA2 is a large protein, and multiple epitopes were detected by each serum sample in both studies. We limited our analysis to those epitopes that were detected by a minimum of six of eight patient samples (75%) in each epitope mapping. As expected the results of the 2 studies were similar, though there were some differences, probably due to epitope length. In both studies, analysis demonstrated that the epitopes were not uniform in length and for some areas antibody binding spanned adjacent peptides. We have not determined if the epitopes overlapped or were adjacent. After analysis and comparison of the 2 studies, we selected nine peptides, encompassing epitopes from 5 different regions of the peptide for synthesis and further study: OppA2 (11-25), OppA2 (191-225), OppA2 (276-290), OppA2 (276-300), OppA2 (286-300), OppA2 (286-310), OppA2 (381-400), OppA2 (356-375) and OppA2 (491-505) (Table 6, FIG. 8). As shown in FIG. 8, epitopes were not clustered within one specific region of OppA2 but are present along the entire length of the protein. The region of OppA2 (276-310) had the highest rate of recognition. Between the 2 studies, 15 of 16 serum samples demonstrated antibody binding in that area of the protein. However, not all samples bound to the same peptide sequence. This suggested that this region has a high level of exposure to the immune system and contains more than one epitope. Because of this we generated multiple peptides encompassing this region.

TABLE 6

Sequences of 9 peptides chosen for ELISAs

| Peptide name/<br>position in<br>the protein | Peptide Sequence |
|---|---|
| OppA (11-25) | IFFLTFLCCNNKERK (SEQ ID NO: 10) |
| OppA (191-225) | YGQNWTSPENMVTSGPFKLKERIPNEKYV<br>FEKNNK (SEQ ID NO: 11) |
| OppA (276-290) | SDYYSSAVNAIYFYA (SEQ ID NO: 12) |
| OppA (276-300) | SDYYSSAVNAIYFYAFNTHIKPLD<br>(SEQ ID NO: 14) |

TABLE 6-continued

Sequences of 9 peptides chosen for ELISAs

| Peptide name/<br>position in<br>the protein | Peptide Sequence |
|---|---|
| OppA (286-300) | IYFYAFNTHIKPLDN (SEQ ID NO: 13) |
| OppA (286-310) | IYFYSFNTHIKPLDNVKIRKALTLA<br>(SEQ ID NO: 52) |
| OppA (356-375) | LAEAGYPNGNGFPILKLKYN<br>(SEQ ID NO: 47) |
| OppA (381-400) | KKICEFIQNQWKKNLNIDVE<br>(SEQ ID NO: 45) |
| OppA (491-505) | APIYIYGNSYLFRND (SEQ ID NO: 53) |

OppA2 peptides react specifically with antibodies from Lyme disease patients. The nine peptides were further screened by ELISA using serum or plasma obtained from 104 patients with physician-diagnosed Lyme disease. All patients presented with one or more EM. Control sera was obtained from 45 healthy donors residing in a region of the United States non-endemic for LD, New Mexico. All peptides were incubated with serum in triplicate, and results were validated in two independent experiments. For each peptide, the threshold value for immunoreactivity was defined as the mean optical density (OD) value plus two standard deviations (SD) of results obtained using healthy donor sera. Peptides OppA2 (11-25) and OppA2 (495-505) were excluded from further evaluation because the reactivity of Lyme disease patient sera was comparable to that of sera from healthy donors (data not shown). Five of the seven remaining peptides were significantly more immunoreactive with Lyme disease serum than healthy control serum: OppA2 (276-290), 37.6%; OppA2 (276-300), 36.6%; OppA2 (286-300), 44.5%; OppA2 (286-310), 43.6%; and OppA2 (356-375), 45.5% (Table 7). Peptides OppA2 (191-225) and OppA2 (381-400) reacted with a notably higher percentage (63.4% and 61.4%, respectively) of the LD patient samples than did the other five peptides (Table 2, not statistically significant (NS)). OppA2 (191-225) and OppA2 (381-400) were detected by only 2.2% and 6.7%, respectively, of the healthy donor samples.

The specificity of the antibody response to these seven peptides was further assessed using sera from 30 patients diagnosed with rheumatoid arthritis and from 26 patients with a positive RPR. The RPR test is used as a screening test for Syphilis, an infection caused by the related spirochete *Treponema pallidum*. None of the peptides were immunoreactive for rheumatoid arthritis patient sera (Table 7). In addition, antibodies present in RPR+ serum did not bind OppA2 (276-300), OppA2 286-300), OppA2 (286-310) and OppA2 (356-375), while a small number of samples bound to OppA2 (191-225)(3/26, 11.5%), OppA2 (276-290)(1/26, 3.8%) and OppA2 (381-400)(3/26, 11.5%).

TABLE 7

Antibody positivity of sample sera with ELISA

| Serum panel | N° positive/Total (% positive) | | | | | | |
|---|---|---|---|---|---|---|---|
| | OppA (191-225) | OppA (381-400) | OppA (276-290) | OppA (276-300) | OppA (286-300) | OppA (286-310) | OppA (356-375) |
| Lyme Disease sera | | | | | | | |
| EM positive (1st visit) | 64/104 (63.4) | 62/104 (61.4) | 38/104 (37.6) | 34/104 (36.6) | 45/104 (44.5) | 44/104 (43.6) | 46/104 (45.5) |
| Wisconsin | 41/46 (89.1) | 38/46 (82.6) | 30/46 (65.2) | 26/46 (56.5) | 36/46 (78.3) | 36/46 (78.3) | 37/46 (80.4) |
| Elisa Positive | 18/35 (51.4) | 17/35 (48.5) | 6/35 (17.1) | 8/35 (22.9) | 7/35 (20) | 8/35 (22.9) | 9/35 (25.7) |
| Blood culture negative | 0/13 (0) | 0/13 (0) | 0/13 (0) | 0/13 (0) | 0/13 (0) | 0/13 (0) | 0/13 (0) |
| Blood culture positive | 5/10 (50) | 4/10 (40) | 2/10 (20) | 0/10 (0) | 2/10 (20) | 0/10 (0) | 0/10 (0) |
| Control sera | | | | | | | |
| Healthy blood donors | 2/45 (4.4) | 3/45 (6.7) | 2/45 (4.4) | 2/45 (4.4) | 2/45 (4.4) | 2/45 (4.4) | 1/45 (2.2) |
| RA | 0/30 (0) | 0/30 (0) | 0/30 (0) | 0/30 (0) | 0/30 (0) | 0/30 (0) | 0/30 (0) |
| Syphilis | 3/26 (11.5) | 3/26 (11.5) | 1/26 (3.8) | 0/26 (0) | 0/26 (0) | 0/26 (0) | 0/26 (0) |

We further analyzed the differences between each group by comparing the mean optical density values obtained for the sample groups (FIG. 9). For each of the seven peptides, a statistically significant difference (p≤0.001) was detected when comparing the mean reactivity of Lyme disease patient samples with that of healthy donor sera. In contrast, there was no significant difference for any of the peptides when comparing sera from healthy patients with either RA or syphilis sera. Moreover, each of the peptide displayed significantly higher immunoreactivity with Lyme disease patient samples than with either rheumatoid arthritis or syphilis sera.

OppA2 peptides distinguish between localized and disseminated *B. burgdorferi* infection. A subset of serum samples were obtained from patients in which microbiologic evidence of *Borellia* infection had been obtained. That is, the presence of the bacteria was confirmed through PCR or culture of skin and/or blood samples. Plasma or sera from LD patients were obtained at the time of the initial visit (day 0) or at a second visit (day 30) following completion of antibiotic treatment. Patients were categorized as having localized (n=13, day 0 and day 30) or disseminated (n=10, day 0; n=16, day 30) infection based on the detection of *B. burgdorferi* DNA or spirochetes by PCR amplification or by culture and microscopic examination, respectively, of blood or skin biopsies. We evaluated peptide immunoreactivity using only these patients to determine if a particular epitope could be quantitatively associated with disseminated infection. In this serum set, none of the patients with localized Lyme disease reacted with any of the OppA2 peptides, while OppA2 (191-225) and OppA2 (381-400) were detected by 50% (5/10) and 40% (4/10), respectively, of samples from patients who had disseminated Lyme disease infection (Table 8). A statistically significant differences in the mean optical density values between samples from localized and disseminated *B. burgdorferi* infection, both at day 0 and day 30 (p≤0.05 and p≤0.001, respectively) (FIG. 3). In addition, mean reactivity of OppA2 (191-225) and OppA2 (381-400) with disseminating sera was significantly higher than with normal control samples (p≤0.001) (FIG. 10). In contrast, no difference between the patient groups could be detected for any of the other peptides. Though few patients with directly observed *Borrelia* infection were available for evaluation, these data suggest that epitopes, such as those located on OppA2 (191-225) and OppA2 (381-400), are useful for differentiating between localized and early disseminating infection. Larger patient groups will be studied to confirm that the serological diagnostic markers can differentiate between disseminating and localized *B. burgdorferi* infections.

Figure 11:
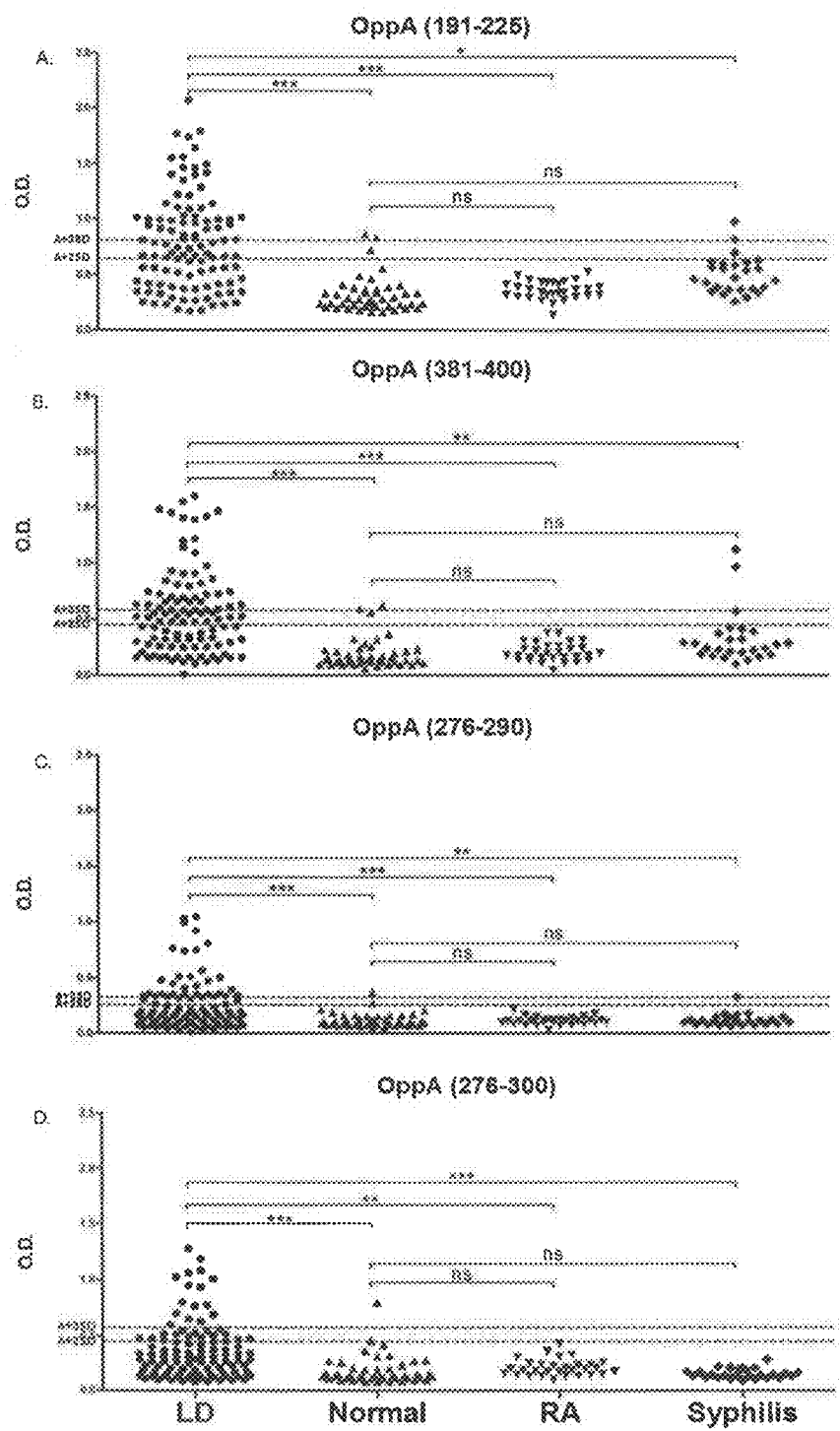
FIG. 11 shows ELISAs with individual synthetic peptides for detection of IgG- and IgM antibodies in humans. Detection of antibodies with synthetic peptides by ELISA assay using sera from normal controls (n=45), EM at first presentation (n=104), rheumatoid arthritis (n=30) and syphilis (n=26). It was used 500 nanograms/well of each peptide (panel A to G). *=p≤0.05; =p≤0.01; *=p≤0.001; ns=not significant.
Figure 11:
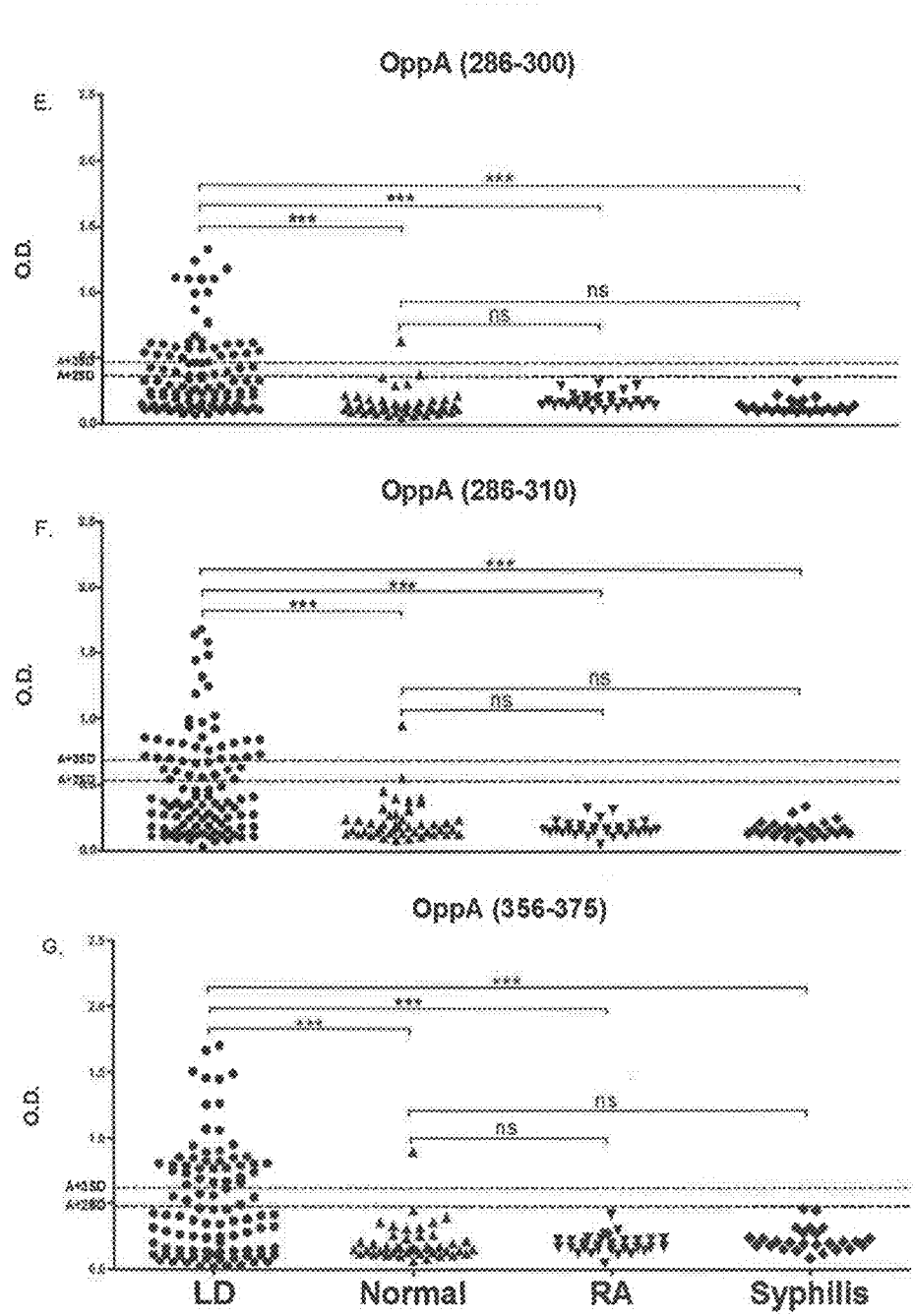
Figure 12:
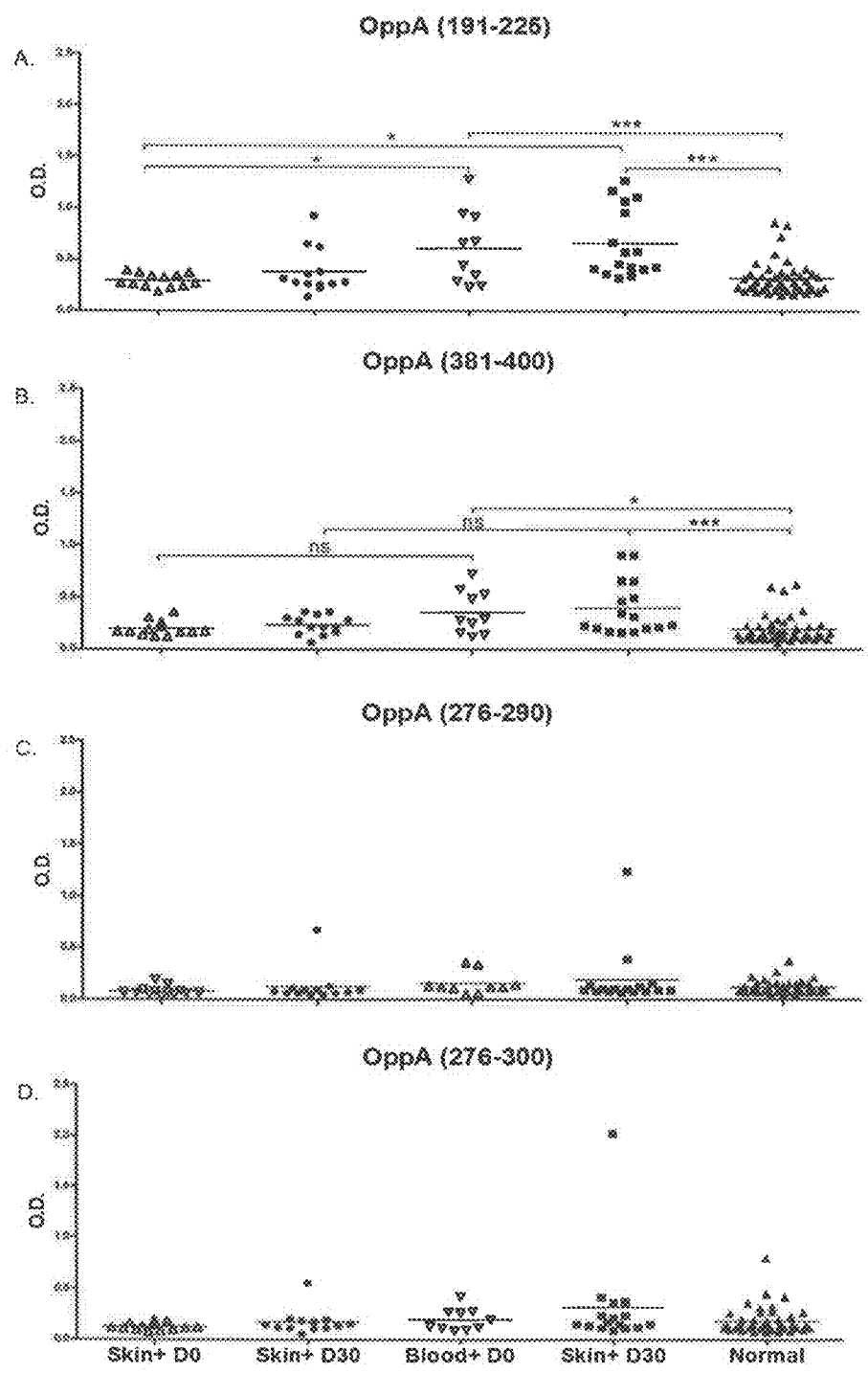
FIG. 12 shows ELISAs with individual synthetic peptides for detection of IgG- and IgM antibodies in humans. Detection of antibodies with synthetic peptides by ELISA assay using sera from Skin PCR positive and Blood culture negative Lyme Disease sera, day 0 and day 30 (n=13 each), sera from Skin PCR positive and Blood culture positive Lyme Disease sera (n=10 and n=16, respectively) and healthy controls (n=45). It was used 500 nanograms/well of each peptide (panel A to G). *=p≤0.05; =p≤0.01; *=p≤0.001; ns=not significant.
Figure 12:
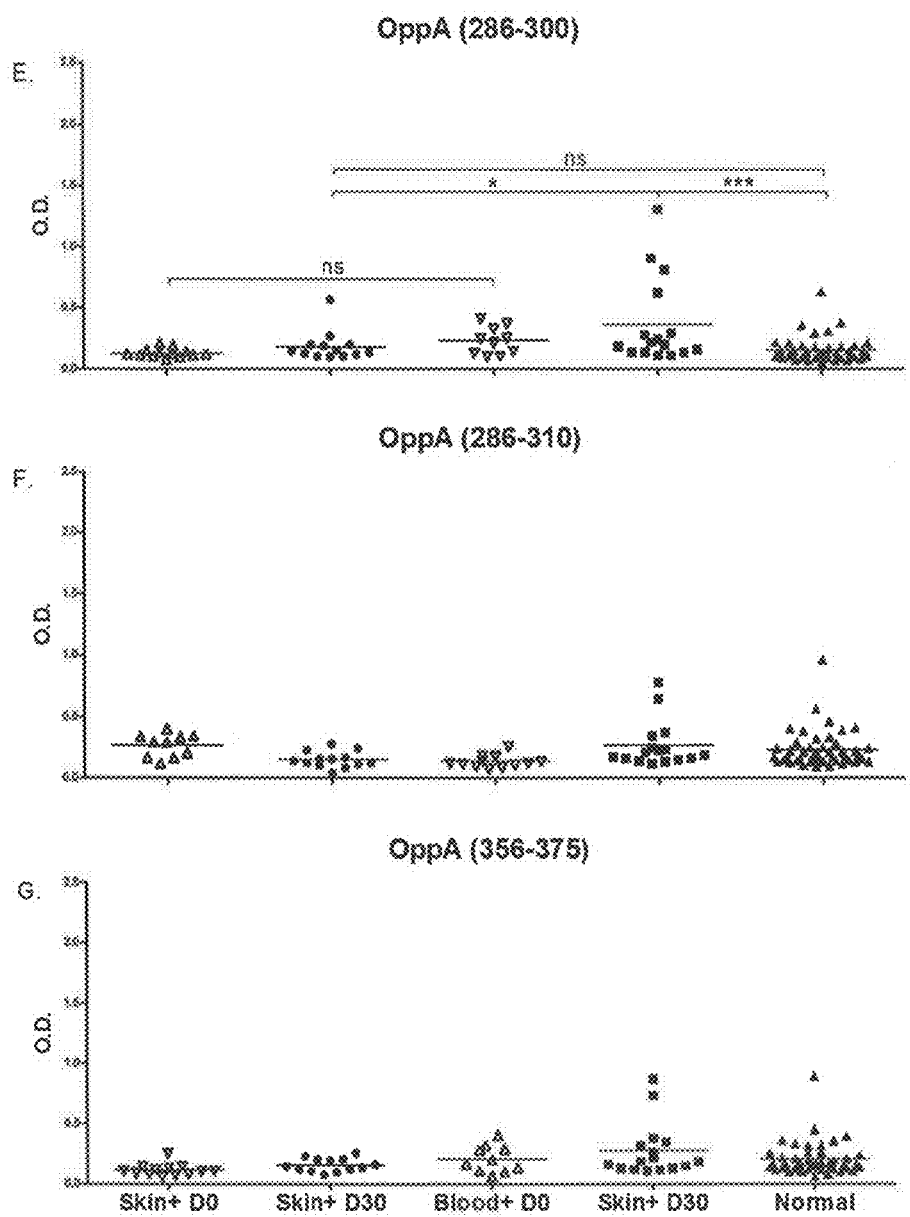

OppA2 (191-225) and OppA2 (381-400) linear epitopes are conserved among different pathogenic *Borrelia* species. LD in North America is caused by diverse genotypes of *B. burgdorferi*, while *B. garinii* and *B. afzelli* are the primary agents of LD in Europe. A highly sensitive diagnostic test for LD would have the capacity to detect an antibody response to all of these *Borrelia* species. To determine whether the immunodominant linear epitopes of OppA2 are conserved among pathogenic *Borrelia* a BLAST comparison was performed using the sequences of OppA2 (191-225) and OppA2 (381-400). Though differences in single AA were present among the different *Borrelia* species, both epitopes were present in each of the different species evaluated (FIG. 11).

*B. burgdorferi* OppA peptide-binding proteins are recognized early in the course of human infection and thus can add to the ability to diagnosis Lyme disease at an early stage. Oligopeptide permease A (OppA) is the peptide-binding component of the only known peptide-transport system in *B. burgdorferi*. It is encoded by five homologs that are differentially expressed in various environmental conditions; in fed and unfed ticks, oppA-2 and oppA-4 mRNA was below the limit of reliable detection. However, OppA2 is upregulated in mouse tissue by day (Xing-Guo Wang, Bo Lin, J. Michael Kidder, Samuel Telford, and Linden T. Hu, JOURNAL OF BACTERIOLOGY, November 2002, p. 6198-6206 Vol. 184, No. 22). In a rabbit model of skin infection, OppA2 was expressed by day 7 of infection (Crother et al, INFECTION AND IMMUNITY, September 2004, p. 5063-5072 Vol. 72, No. 9). A recent study using non-human primates highlighted the importance of OppA2 not only as a significant antigen in early infection but as a potential indicator of spirochete clearance. Because of its ability to induce an early immune response during mammalian infection, and the fact that the amino acid sequence of OppA2 is highly conserved among all 3 major pathogenic genospecies of *B. burgdorferi* (Kornacki and Oliver, 1998, Infection and Immunity), and as antibodies against *B. burgdorferi* OppA2 do not cross react with Opp proteins from other species, such as *E. coli* (Lin, 2001, Biochimica et Biophysica Acta), OppA2 presents an attractive target for serodiagnosis.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. provisional applications No. 61/593,605, filed Feb. 1, 2012; No. 61/680,583, filed Aug. 7, 2012; and No. 61/705,344, filed Sep. 25, 2012, and in the figures, are hereby incorporated in their entirety by reference, particularly with regard to the disclosure for which they are referenced.

SEQUENCE LISTING

```
<160> NUMBER OF SEQ ID NOS: 295

<210> SEQ ID NO 1
<211> LENGTH: 15
<212> TYPE: PRT
<213> ORGANISM: Borrelia sp.

<400> SEQUENCE: 1

Phe Glu Asp Ala Met Lys Leu Gly Leu Ala Leu Tyr Leu Asp Tyr
1               5                   10                  15

<210> SEQ ID NO 2
<211> LENGTH: 15
<212> TYPE: PRT
<213> ORGANISM: Borrelia sp.

<400> SEQUENCE: 2

Leu Ile Arg Phe Thr Thr Ile Ser Leu Gly Trp Asp Ser Asn Asn
1               5                   10                  15

<210> SEQ ID NO 3
<211> LENGTH: 15
<212> TYPE: PRT
<213> ORGANISM: Borrelia sp.

<400> SEQUENCE: 3

Lys Phe Tyr Ser Ser Leu Arg Leu Glu Val Arg Lys Ile Glu Gln
1               5                   10                  15

<210> SEQ ID NO 4
<211> LENGTH: 20
<212> TYPE: PRT
<213> ORGANISM: Borrelia sp.

<400> SEQUENCE: 4

Ile Pro Ser Lys Glu Asn Ala Lys Leu Ile Val Tyr Phe Tyr Asp Asn
1               5                   10                  15

Val Tyr Ala Gly
            20

<210> SEQ ID NO 5
<211> LENGTH: 15
<212> TYPE: PRT
<213> ORGANISM: Borrelia sp.

<400> SEQUENCE: 5

Ile Pro Ser Lys Glu Asn Ala Lys Leu Ile Val Tyr Phe Tyr Asp
1               5                   10                  15

<210> SEQ ID NO 6
<211> LENGTH: 15
<212> TYPE: PRT
<213> ORGANISM: Borrelia sp.

<400> SEQUENCE: 6
```

```
Asn Ala Lys Leu Ile Val Tyr Phe Tyr Asp Asn Val Tyr Ala Gly
1               5                   10                  15

<210> SEQ ID NO 7
<211> LENGTH: 20
<212> TYPE: PRT
<213> ORGANISM: Borrelia sp.

<400> SEQUENCE: 7

Lys Asn Glu Gly Leu Lys Glu Lys Ile Asp Ala Ala Lys Lys Cys Ser
1               5                   10                  15

Glu Thr Phe Thr
            20

<210> SEQ ID NO 8
<211> LENGTH: 20
<212> TYPE: PRT
<213> ORGANISM: Borrelia sp.

<400> SEQUENCE: 8

Met Thr Leu Phe Leu Phe Ile Ser Cys Asn Asn Ser Gly Lys Asp Gly
1               5                   10                  15

Asn Thr Ser Ala
            20

<210> SEQ ID NO 9
<211> LENGTH: 15
<212> TYPE: PRT
<213> ORGANISM: Borrelia burgdorferi

<400> SEQUENCE: 9

Ala Lys Lys Ala Ile Leu Ile Thr Asp Ala Ala Lys Asp Lys Gly
1               5                   10                  15

<210> SEQ ID NO 10
<211> LENGTH: 15
<212> TYPE: PRT
<213> ORGANISM: Borrelia sp.

<400> SEQUENCE: 10

Ile Phe Phe Leu Thr Phe Leu Cys Cys Asn Asn Lys Glu Arg Lys
1               5                   10                  15

<210> SEQ ID NO 11
<211> LENGTH: 35
<212> TYPE: PRT
<213> ORGANISM: Borrelia sp.

<400> SEQUENCE: 11

Tyr Gly Gln Asn Trp Thr Ser Pro Glu Asn Met Val Thr Ser Gly Pro
1               5                   10                  15

Phe Lys Leu Lys Glu Arg Ile Pro Asn Glu Lys Tyr Val Phe Glu Lys
                20                  25                  30

Asn Asn Lys
        35

<210> SEQ ID NO 12
<211> LENGTH: 15
<212> TYPE: PRT
<213> ORGANISM: Borrelia sp.

<400> SEQUENCE: 12
```

```
Ser Asp Tyr Tyr Ser Ser Ala Val Asn Ala Ile Tyr Phe Tyr Ala
1               5                   10                  15
```

<210> SEQ ID NO 13
<211> LENGTH: 15
<212> TYPE: PRT
<213> ORGANISM: Borrelia sp.

<400> SEQUENCE: 13

```
Ile Tyr Phe Tyr Ala Phe Asn Thr His Ile Lys Pro Leu Asp Asn
1               5                   10                  15
```

<210> SEQ ID NO 14
<211> LENGTH: 25
<212> TYPE: PRT
<213> ORGANISM: Borrelia sp.

<400> SEQUENCE: 14

```
Ser Asp Tyr Tyr Ser Ser Ala Val Asn Ala Ile Tyr Phe Tyr Ala Phe
1               5                   10                  15

Asn Thr His Ile Lys Pro Leu Asp Asn
                20                  25
```

<210> SEQ ID NO 15
<211> LENGTH: 15
<212> TYPE: PRT
<213> ORGANISM: Borrelia sp.

<400> SEQUENCE: 15

```
Asp Met Phe Ser Leu Glu Gln Arg Leu Glu Ile Lys Leu Glu Ala
1               5                   10                  15
```

<210> SEQ ID NO 16
<211> LENGTH: 15
<212> TYPE: PRT
<213> ORGANISM: Borrelia sp.

<400> SEQUENCE: 16

```
Leu Val Ala Cys Ser Ile Gly Leu Val Glu Arg Thr Asn Ala Ala
1               5                   10                  15
```

<210> SEQ ID NO 17
<211> LENGTH: 15
<212> TYPE: PRT
<213> ORGANISM: Borrelia sp.

<400> SEQUENCE: 17

```
Lys Glu Glu Phe Lys Ile Glu Leu Val Leu Lys Glu Ser Ser Ser
1               5                   10                  15
```

<210> SEQ ID NO 18
<211> LENGTH: 15
<212> TYPE: PRT
<213> ORGANISM: Borrelia sp.

<400> SEQUENCE: 18

```
Ile Val Ser Tyr Phe Val Ser Lys Met Val Val Ser Gln Ser Gly
1               5                   10                  15
```

<210> SEQ ID NO 19
<211> LENGTH: 20
<212> TYPE: PRT
<213> ORGANISM: Borrelia sp.

<400> SEQUENCE: 19

Asn Thr Leu Asp Val Pro Pro Lys Thr Phe Val Val Lys Leu Ala Leu
1               5                   10                  15

Gly Tyr Ala Glu
            20

<210> SEQ ID NO 20
<211> LENGTH: 15
<212> TYPE: PRT
<213> ORGANISM: Borrelia sp.

<400> SEQUENCE: 20

Val Ser Arg Lys Gly Gly Leu Leu Pro Asp Ile Ile Lys Ile
1               5                   10                  15

<210> SEQ ID NO 21
<211> LENGTH: 15
<212> TYPE: PRT
<213> ORGANISM: Borrelia sp.

<400> SEQUENCE: 21

Leu Lys Asp Ile Ile Arg Glu Tyr Phe Ser Gln Arg Thr Gly Gln
1               5                   10                  15

<210> SEQ ID NO 22
<211> LENGTH: 15
<212> TYPE: PRT
<213> ORGANISM: Borrelia sp.

<400> SEQUENCE: 22

Gly Phe Ile Ser Cys Asp Leu Phe Ile Arg Tyr Glu Met Lys Glu
1               5                   10                  15

<210> SEQ ID NO 23
<211> LENGTH: 30
<212> TYPE: PRT
<213> ORGANISM: Borrelia sp.

<400> SEQUENCE: 23

Lys Lys Pro Met Asn Lys Lys Gly Lys Gly Lys Ile Ala Arg Lys Lys
1               5                   10                  15

Gly Lys Ser Lys Val Ser Arg Lys Glu Pro Tyr Ile His Ser
            20                  25                  30

<210> SEQ ID NO 24
<211> LENGTH: 15
<212> TYPE: PRT
<213> ORGANISM: Borrelia sp.

<400> SEQUENCE: 24

Asp Thr Gly Ser Glu Arg Ser Ile Arg Tyr Arg Arg Val Tyr
1               5                   10                  15

<210> SEQ ID NO 25
<211> LENGTH: 15
<212> TYPE: PRT
<213> ORGANISM: Borrelia sp.

<400> SEQUENCE: 25

Lys Ile Glu Phe Ser Lys Phe Thr Val Lys Ile Lys Asn Lys Asp
1               5                   10                  15

<210> SEQ ID NO 26
<211> LENGTH: 20

<212> TYPE: PRT
<213> ORGANISM: Borrelia sp.

<400> SEQUENCE: 26

Asn Ser Arg Ser Arg Tyr Asn Asn Phe Tyr Lys Lys Glu Ala Asp Phe
1               5                   10                  15

Leu Gly Ala Ala
            20

<210> SEQ ID NO 27
<211> LENGTH: 20
<212> TYPE: PRT
<213> ORGANISM: Borrelia sp.

<400> SEQUENCE: 27

Ile Asn Lys Leu Glu Ala Lys Lys Thr Ser Leu Lys Thr Tyr Ser Glu
1               5                   10                  15

Tyr Glu Glu Gln
            20

<210> SEQ ID NO 28
<211> LENGTH: 15
<212> TYPE: PRT
<213> ORGANISM: Borrelia sp.

<400> SEQUENCE: 28

Ile Asp Asp Ser Ile Lys Lys Ile Asp Glu Glu Leu Lys Asn Thr
1               5                   10                  15

<210> SEQ ID NO 29
<211> LENGTH: 35
<212> TYPE: PRT
<213> ORGANISM: Borrelia garinii

<400> SEQUENCE: 29

Tyr Gly Glu Asn Trp Thr Asn Pro Glu Asn Ile Val Val Ser Gly Ala
1               5                   10                  15

Tyr Lys Leu Lys Glu Arg Leu Ile Asn Asp Lys Ile Val Ile Glu Lys
            20                  25                  30

Asn Glu Lys
        35

<210> SEQ ID NO 30
<211> LENGTH: 33
<212> TYPE: PRT
<213> ORGANISM: Borrelia afzelli

<400> SEQUENCE: 30

Tyr Lys Gly Asn Trp Thr Asn Pro Glu Asn Met Val Thr Ser Gly Pro
1               5                   10                  15

Phe Lys Leu Lys Lys Arg Leu Pro Asn Glu Lys Ile Ile Phe Glu Lys
            20                  25                  30

Asn

<210> SEQ ID NO 31
<211> LENGTH: 20
<212> TYPE: PRT
<213> ORGANISM: Borrelia garinii

<400> SEQUENCE: 31

Met Thr Leu Phe Leu Phe Ile Ser Cys Asn Asn Ser Gly Lys Gly Gly
1               5                   10                  15

Asp Ser Ala Ser
        20

<210> SEQ ID NO 32
<211> LENGTH: 15
<212> TYPE: PRT
<213> ORGANISM: Borrelia sp.

<400> SEQUENCE: 32

Val Gly Arg Lys Gly Gly Leu Leu Pro Asp Ile Ile Ile Lys Ile
1               5                   10                  15

<210> SEQ ID NO 33
<211> LENGTH: 15
<212> TYPE: PRT
<213> ORGANISM: Borrelia garinii

<400> SEQUENCE: 33

Phe Glu Asp Ala Met Lys Ile Gly Ile Ala Leu Tyr Leu Asp Tyr
1               5                   10                  15

<210> SEQ ID NO 34
<211> LENGTH: 15
<212> TYPE: PRT
<213> ORGANISM: Borrelia afzelli

<400> SEQUENCE: 34

Phe Glu Asp Ala Met Lys Leu Gly Ile Ala Leu Tyr Leu Asp Tyr
1               5                   10                  15

<210> SEQ ID NO 35
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Lys or Gly
<220> FEATURE:
<221> NAME/KEY: MOD_RES
<222> LOCATION: (3)..(3)
<223> OTHER INFORMATION: Gln, Glu or Gly
<220> FEATURE:
<221> NAME/KEY: MOD_RES
<222> LOCATION: (7)..(7)
<223> OTHER INFORMATION: Ser or Asn
<220> FEATURE:
<221> NAME/KEY: MOD_RES
<222> LOCATION: (11)..(11)
<223> OTHER INFORMATION: Met or Ile
<220> FEATURE:
<221> NAME/KEY: MOD_RES
<222> LOCATION: (13)..(13)
<223> OTHER INFORMATION: Thr or Val
<220> FEATURE:
<221> NAME/KEY: MOD_RES
<222> LOCATION: (16)..(16)
<223> OTHER INFORMATION: Pro or Ala
<220> FEATURE:
<221> NAME/KEY: MOD_RES
<222> LOCATION: (17)..(17)
<223> OTHER INFORMATION: Phe or Tyr
<220> FEATURE:
<221> NAME/KEY: MOD_RES
<222> LOCATION: (21)..(21)
<223> OTHER INFORMATION: Glu or Lys
<220> FEATURE:
<221> NAME/KEY: MOD_RES

```
<222> LOCATION: (23)..(23)
<223> OTHER INFORMATION: Ile or Leu
<220> FEATURE:
<221> NAME/KEY: MOD_RES
<222> LOCATION: (24)..(24)
<223> OTHER INFORMATION: Pro or Ile
<220> FEATURE:
<221> NAME/KEY: MOD_RES
<222> LOCATION: (26)..(26)
<223> OTHER INFORMATION: Glu or Asp
<220> FEATURE:
<221> NAME/KEY: MOD_RES
<222> LOCATION: (28)..(28)
<223> OTHER INFORMATION: Tyr or Ile
<220> FEATURE:
<221> NAME/KEY: MOD_RES
<222> LOCATION: (29)..(29)
<223> OTHER INFORMATION: Val or Ile
<220> FEATURE:
<221> NAME/KEY: MOD_RES
<222> LOCATION: (30)..(30)
<223> OTHER INFORMATION: Phe or Ile
<220> FEATURE:
<221> NAME/KEY: MOD_RES
<222> LOCATION: (34)..(34)
<223> OTHER INFORMATION: Asn, Glu or absent
<220> FEATURE:
<221> NAME/KEY: MOD_RES
<222> LOCATION: (35)..(35)
<223> OTHER INFORMATION: Lys or absent

<400> SEQUENCE: 35

Tyr Xaa Xaa Asn Trp Thr Xaa Pro Glu Asn Xaa Val Xaa Ser Gly Xaa
1               5                   10                  15

Xaa Lys Leu Lys Xaa Arg Xaa Xaa Asn Xaa Lys Xaa Xaa Xaa Glu Lys
            20                  25                  30

Asn Xaa Xaa
        35

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Pro Val Val Ala Glu Ser Pro Lys Lys Pro
1               5                   10

<210> SEQ ID NO 37
<211> LENGTH: 14
<212> TYPE: PRT
<213> ORGANISM: Borrelia sp.

<400> SEQUENCE: 37

Ile Leu Met Thr Leu Phe Leu Phe Ile Ser Cys Asn Asn Ser
1               5                   10

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 38

His His His His His His
```

<210> SEQ ID NO 39
<211> LENGTH: 13
<212> TYPE: PRT
<213> ORGANISM: Borrelia sp.

<400> SEQUENCE: 39

Val Gln Glu Gly Val Gln Gln Glu Gly Ala Gln Gln Pro
1               5                   10

<210> SEQ ID NO 40
<211> LENGTH: 10
<212> TYPE: PRT
<213> ORGANISM: Borrelia sp.

<400> SEQUENCE: 40

Pro Val Val Ala Glu Ser Pro Lys Lys Pro
1               5                   10

<210> SEQ ID NO 41
<211> LENGTH: 15
<212> TYPE: PRT
<213> ORGANISM: Borrelia sp.

<400> SEQUENCE: 41

Asn Lys Thr Phe Asn Asn Leu Leu Lys Leu Thr Ile Leu Val Asn
1               5                   10                  15

<210> SEQ ID NO 42
<211> LENGTH: 25
<212> TYPE: PRT
<213> ORGANISM: Borrelia sp.

<400> SEQUENCE: 42

Asn Lys Thr Phe Asn Asn Leu Leu Lys Leu Thr Ile Leu Val Asn Leu
1               5                   10                  15

Leu Ile Ser Cys Gly Leu Thr Gly Ala
            20                  25

<210> SEQ ID NO 43
<211> LENGTH: 15
<212> TYPE: PRT
<213> ORGANISM: Borrelia sp.

<400> SEQUENCE: 43

Thr Ile Leu Val Asn Leu Leu Ile Ser Cys Gly Leu Thr Gly Ala
1               5                   10                  15

<210> SEQ ID NO 44
<211> LENGTH: 15
<212> TYPE: PRT
<213> ORGANISM: Borrelia sp.

<400> SEQUENCE: 44

Pro Phe Ile Leu Glu Ala Lys Val Arg Ala Thr Thr Val Ala Glu
1               5                   10                  15

<210> SEQ ID NO 45
<211> LENGTH: 20
<212> TYPE: PRT
<213> ORGANISM: Borrelia burgdorferi

<400> SEQUENCE: 45

```
Lys Lys Ile Cys Glu Phe Ile Gln Asn Gln Trp Lys Lys Asn Leu Asn
1               5                   10                  15

Ile Asp Val Glu
            20

<210> SEQ ID NO 46
<211> LENGTH: 25
<212> TYPE: PRT
<213> ORGANISM: Borrelia sp.

<400> SEQUENCE: 46

Ile Tyr Phe Tyr Ala Phe Asn Thr His Ile Lys Pro Leu Asp Asn Val
1               5                   10                  15

Lys Ile Arg Lys Ala Leu Thr Leu Ala
            20                  25

<210> SEQ ID NO 47
<211> LENGTH: 20
<212> TYPE: PRT
<213> ORGANISM: Borrelia burgdorferi

<400> SEQUENCE: 47

Leu Ala Glu Ala Gly Tyr Pro Asn Gly Asn Gly Phe Pro Ile Leu Lys
1               5                   10                  15

Leu Lys Tyr Asn
            20

<210> SEQ ID NO 48
<211> LENGTH: 26
<212> TYPE: PRT
<213> ORGANISM: Borrelia garinii

<400> SEQUENCE: 48

Cys Met Lys Lys Asp Asp Gln Ile Ala Ala Ala Met Val Leu Arg Gly
1               5                   10                  15

Met Ala Lys Asp Gly Gln Phe Ala Leu Lys
            20                  25

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Val or Gly

<400> SEQUENCE: 49

Met Lys Lys Asn Asp Gln Ile Xaa Ala Ala Ile Ala Leu Arg Gly Val
1               5                   10                  15

Ala

<210> SEQ ID NO 50
<211> LENGTH: 17
<212> TYPE: PRT
<213> ORGANISM: Borrelia garinii

<400> SEQUENCE: 50

Met Lys Lys Asp Asp Gln Ile Ala Ala Ala Ile Ala Leu Arg Gly Met
1               5                   10                  15
```

-continued

Ala

<210> SEQ ID NO 51
<211> LENGTH: 15
<212> TYPE: PRT
<213> ORGANISM: Borrelia sp.

<400> SEQUENCE: 51

Thr Leu Leu Ala Gly Ala Tyr Thr Ile Ser Lys Leu Ile Thr Gln
1               5                   10                  15

<210> SEQ ID NO 52
<211> LENGTH: 25
<212> TYPE: PRT
<213> ORGANISM: Borrelia sp.

<400> SEQUENCE: 52

Ile Tyr Phe Tyr Ser Phe Asn Thr His Ile Lys Pro Leu Asp Asn Val
1               5                   10                  15

Lys Ile Arg Lys Ala Leu Thr Leu Ala
            20                  25

<210> SEQ ID NO 53
<211> LENGTH: 15
<212> TYPE: PRT
<213> ORGANISM: Borrelia burgdorferi

<400> SEQUENCE: 53

Ala Pro Ile Tyr Ile Tyr Gly Asn Ser Tyr Leu Phe Arg Asn Asp
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glu or Ala
<220> FEATURE:
<221> NAME/KEY: MOD_RES
<222> LOCATION: (4)..(4)
<223> OTHER INFORMATION: Phe or Arg
<220> FEATURE:
<221> NAME/KEY: MOD_RES
<222> LOCATION: (5)..(5)
<223> OTHER INFORMATION: Lys or Glu
<220> FEATURE:
<221> NAME/KEY: MOD_RES
<222> LOCATION: (6)..(6)
<223> OTHER INFORMATION: Ile or Phe
<220> FEATURE:
<221> NAME/KEY: MOD_RES
<222> LOCATION: (15)..(15)
<223> OTHER INFORMATION: Ser or Thr

<400> SEQUENCE: 54

Lys Xaa Glu Xaa Xaa Xaa Glu Leu Val Leu Lys Glu Ser Ser Xaa
1               5                   10                  15

<210> SEQ ID NO 55
<211> LENGTH: 15
<212> TYPE: PRT
<213> ORGANISM: Borrelia sp.

<400> SEQUENCE: 55

Lys Glu Glu Phe Lys Ile Glu Leu Val Leu Lys Glu Ser Ser Thr
1               5                   10                  15

<210> SEQ ID NO 56
<211> LENGTH: 12
<212> TYPE: PRT
<213> ORGANISM: Borrelia sp.

<400> SEQUENCE: 56

Lys Ala Glu Arg Lys Ile Glu Leu Val Leu Lys Glu
1               5                   10

<210> SEQ ID NO 57
<211> LENGTH: 15
<212> TYPE: PRT
<213> ORGANISM: Borrelia sp.

<400> SEQUENCE: 57

Lys Glu Glu Phe Lys Phe Glu Leu Val Leu Lys Glu Ser Ser Thr
1               5                   10                  15

<210> SEQ ID NO 58
<211> LENGTH: 15
<212> TYPE: PRT
<213> ORGANISM: Borrelia sp.

<400> SEQUENCE: 58

Lys Glu Glu Phe Glu Ile Glu Leu Val Leu Lys Glu Ser Ser Thr
1               5                   10                  15

<210> SEQ ID NO 59
<211> LENGTH: 14
<212> TYPE: PRT
<213> ORGANISM: Borrelia sp.

<400> SEQUENCE: 59

Lys Ala Glu Arg Lys Ile Glu Leu Val Asn Leu Leu Lys Glu
1               5                   10

<210> SEQ ID NO 60
<211> LENGTH: 9
<212> TYPE: PRT
<213> ORGANISM: Borrelia sp.

<400> SEQUENCE: 60

Glu Ile Phe Lys Ile Glu Lys Val Leu
1               5

<210> SEQ ID NO 61
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Tyr, His or Phe
<220> FEATURE:
<221> NAME/KEY: MOD_RES
<222> LOCATION: (2)..(2)
<223> OTHER INFORMATION: Gly or Lys
<220> FEATURE:
<221> NAME/KEY: MOD_RES
<222> LOCATION: (3)..(3)
<223> OTHER INFORMATION: Gln, Gly, Glu or Asn

```
<220> FEATURE:
<221> NAME/KEY: MOD_RES
<222> LOCATION: (4)..(4)
<223> OTHER INFORMATION: Asn, Lys, Ser, Arg or Glu
<220> FEATURE:
<221> NAME/KEY: MOD_RES
<222> LOCATION: (7)..(7)
<223> OTHER INFORMATION: Ser, Asn or Asp
<220> FEATURE:
<221> NAME/KEY: MOD_RES
<222> LOCATION: (11)..(11)
<223> OTHER INFORMATION: Met or Ile
<220> FEATURE:
<221> NAME/KEY: MOD_RES
<222> LOCATION: (13)..(13)
<223> OTHER INFORMATION: Thr or Val
<220> FEATURE:
<221> NAME/KEY: MOD_RES
<222> LOCATION: (16)..(16)
<223> OTHER INFORMATION: Pro or Ala
<220> FEATURE:
<221> NAME/KEY: MOD_RES
<222> LOCATION: (17)..(17)
<223> OTHER INFORMATION: Phe or Tyr
<220> FEATURE:
<221> NAME/KEY: MOD_RES
<222> LOCATION: (21)..(21)
<223> OTHER INFORMATION: Glu, Lys, Ser or Arg
<220> FEATURE:
<221> NAME/KEY: MOD_RES
<222> LOCATION: (23)..(23)
<223> OTHER INFORMATION: Ile, Ser, Leu or Val
<220> FEATURE:
<221> NAME/KEY: MOD_RES
<222> LOCATION: (24)..(24)
<223> OTHER INFORMATION: Pro, Leu or Ile
<220> FEATURE:
<221> NAME/KEY: MOD_RES
<222> LOCATION: (26)..(26)
<223> OTHER INFORMATION: Glu or Asp
<220> FEATURE:
<221> NAME/KEY: MOD_RES
<222> LOCATION: (28)..(28)
<223> OTHER INFORMATION: Tyr, Val or Ile
<220> FEATURE:
<221> NAME/KEY: MOD_RES
<222> LOCATION: (29)..(29)
<223> OTHER INFORMATION: Val or Ile
<220> FEATURE:
<221> NAME/KEY: MOD_RES
<222> LOCATION: (30)..(30)
<223> OTHER INFORMATION: Phe, Val, Leu or Ile
<220> FEATURE:
<221> NAME/KEY: MOD_RES
<222> LOCATION: (34)..(34)
<223> OTHER INFORMATION: Asn, Asp or Glu

<400> SEQUENCE: 61

Xaa Xaa Xaa Xaa Trp Thr Xaa Pro Glu Asn Xaa Val Xaa Ser Gly Xaa
1               5                   10                  15

Xaa Lys Leu Lys Xaa Arg Xaa Xaa Asn Xaa Lys Xaa Xaa Xaa Glu Lys
            20                  25                  30

Asn Xaa Lys
        35

<210> SEQ ID NO 62
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62
```

```
Tyr Gly Gln Asn Trp Thr Ser Pro Glu Asn Met Val Thr Ser Gly Pro
1               5                   10                  15

Phe Lys Leu Lys Glu Arg Ile Pro Asn Glu Lys Tyr Val Phe Glu Lys
                20                  25                  30

Asn Asn Lys
        35

<210> SEQ ID NO 63
<211> LENGTH: 35
<212> TYPE: PRT
<213> ORGANISM: Borrelia sp.

<400> SEQUENCE: 63

Tyr Gly Glu Asn Trp Thr Asn Pro Glu Asn Ile Val Val Ser Gly Ala
1               5                   10                  15

Tyr Lys Leu Lys Glu Arg Leu Ile Asn Asp Lys Ile Val Ile Glu Asn
                20                  25                  30

Asn Glu Lys
        35

<210> SEQ ID NO 64
<211> LENGTH: 35
<212> TYPE: PRT
<213> ORGANISM: Borrelia sp.

<400> SEQUENCE: 64

Tyr Gly Gln Glu Trp Thr Asn Pro Glu Asn Met Val Val Ser Gly Pro
1               5                   10                  15

Phe Lys Leu Lys Ser Arg Val Leu Asn Glu L

```
<212> TYPE: PRT
<213> ORGANISM: Borrelia sp.

<400> SEQUENCE: 67

Tyr Gly Gln Ser Trp Thr Asn Pro Glu Asn Ile Val Thr Ser Gly Pro
1               5                   10                  15

Phe Lys Leu Lys Glu Arg Ile Pro Asn Glu Lys Tyr Val Val Glu Lys
            20                  25                  30

Asn Asp Lys
        35

<210> SEQ ID NO 68
<211> LENGTH: 35
<212> TYPE: PRT
<213> ORGANISM: Borrelia sp.

<400> SEQUENCE: 68

Tyr Lys Gly Asn Trp Thr Ser Pro Glu Asn Met Val Thr Ser Gly Pro
1               5                   10                  15

Phe Lys Leu Lys Lys Arg Leu Pro Asn Glu Lys Ile Ile Phe Glu Lys
            20                  25                  30

Asn Glu Arg
        35

<210> SEQ ID NO 69
<211> LENGTH: 35
<212> TYPE: PRT
<213> ORGANISM: Borrelia sp.

<400> SEQUENCE: 69

Tyr Gly Gln Arg Trp Thr Asp Pro Glu Asn Met Val Val Ser Gly Pro
1               5                   10                  15

Phe Lys Leu Lys Ser Arg Val Leu Asn Glu Lys Val Val Leu Glu Lys
            20                  25                  30

Asn Asn Lys
        35

<210> SEQ ID NO 70
<211> LENGTH: 35
<212> TYPE: PRT
<213> ORGANISM: Borrelia sp.

<400> SEQUENCE: 70

His Gly Gln Glu Trp Thr Asn Pro Glu Asn Met Val Val Ser Gly Pro
1               5                   10                  15

Phe Lys Leu Lys Ser Arg Val Leu Asn Glu Lys Ile Ile Leu Glu Lys
            20                  25                  30

Asn Asn Lys
        35

<210> SEQ ID NO 71
<211> LENGTH: 35
<212> TYPE: PRT
<213> ORGANISM: Borrelia sp.

<400> SEQUENCE: 71

Phe Gly Asn Lys Trp Thr Asn Pro Glu Asn Met Val Thr Ser Gly Pro
1               5                   10                  15

Phe Lys Leu Lys Arg Arg Ile Leu Asn Glu Glu Ile Ser Leu Glu Lys
            20                  25                  30
```

Asn Lys Lys
        35

<210> SEQ ID NO 72
<211> LENGTH: 35
<212> TYPE: PRT
<213> ORGANISM: Borrelia sp.

<400> SEQUENCE: 72

Phe Gly Asn Lys Trp Thr Ser Ser Glu Asn Met Val Thr Ser Gly Pro
1               5                   10                  15

Phe Lys Leu Lys Arg Arg Ile Leu Asn Glu Glu Ile Ser Leu Glu Lys
            20                  25                  30

Asn Glu Lys
        35

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Lys or Gly
<220> FEATURE:
<221> NAME/KEY: MOD_RES
<222> LOCATION: (15)..(15)
<223> OTHER INFORMATION: Asp or Gly
<220> FEATURE:
<221> NAME/KEY: MOD_RES
<222> LOCATION: (17)..(17)
<223> OTHER INFORMATION: Asn or Asp
<220> FEATURE:
<221> NAME/KEY: MOD_RES
<222> LOCATION: (18)..(18)
<223> OTHER INFORMATION: Thr, Ala or Ser
<220> FEATURE:
<221> NAME/KEY: MOD_RES
<222> LOCATION: (19)..(19)
<223> OTHER INFORMATION: Ser, Ala or Thr
<220> FEATURE:
<221> NAME/KEY: MOD_RES
<222> LOCATION: (20)..(20)
<223> OTHER INFORMATION: Ala or Ser

<400> SEQUENCE: 73

Met Thr Leu Phe Leu Phe Ile Ser Cys Asn Asn Ser Gly Xaa Xaa Gly
1               5                   10                  15

Xaa Xaa Xaa Xaa
        20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phe, Leu or Tyr
<220> FEATURE:
<221> NAME/KEY: MOD_RES
<222> LOCATION: (9)..(9)
<223> OTHER INFORMATION: Cys or Ser
<220> FEATURE:
<221> NAME/KEY: MOD_RES

```
<222> LOCATION: (11)..(11)
<223> OTHER INFORMATION: Asn or Thr
<220> FEATURE:
<221> NAME/KEY: MOD_RES
<222> LOCATION: (15)..(15)
<223> OTHER INFORMATION: Asp or Gly
<220> FEATURE:
<221> NAME/KEY: MOD_RES
<222> LOCATION: (16)..(16)
<223> OTHER INFORMATION: Gly, Val or Ala
<220> FEATURE:
<221> NAME/KEY: MOD_RES
<222> LOCATION: (17)..(17)
<223> OTHER INFORMATION: Asn, Asp, Thr or Ser
<220> FEATURE:
<221> NAME/KEY: MOD_RES
<222> LOCATION: (18)..(18)
<223> OTHER INFORMATION: Thr, Ala or Ser
<220> FEATURE:
<221> NAME/KEY: MOD_RES
<222> LOCATION: (19)..(19)
<223> OTHER INFORMATION: Ser, Ala or Thr
<220> FEATURE:
<221> NAME/KEY: MOD_RES
<222> LOCATION: (20)..(20)
<223> OTHER INFORMATION: Ala or Thr

<400> SEQUENCE: 74

Met Thr Leu Xaa Leu Phe Ile Ser Xaa Asn Xaa Ser Gly Lys Xaa Xaa
1               5                   10                  15

Xaa Xaa Xaa Xaa
            20

<210> SEQ ID NO 75
<211> LENGTH: 17
<212> TYPE: PRT
<213> ORGANISM: Borrelia sp.

<400> SEQUENCE: 75

Phe Leu Phe Ile Ser Cys Asn Asn Ser Gly Lys Asp Gly Asn Thr Ser
1               5                   10                  15

Ala

<210> SEQ ID NO 76
<211> LENGTH: 15
<212> TYPE: PRT
<213> ORGANISM: Borrelia sp.

<400> SEQUENCE: 76

Thr Leu Phe Leu Phe Ile Ser Cys Asn Asn Ser Gly Gly Asp Thr
1               5                   10                  15

<210> SEQ ID NO 77
<211> LENGTH: 20
<212> TYPE: PRT
<213> ORGANISM: Borrelia sp.

<400> SEQUENCE: 77

Met Thr Leu Phe Leu Phe Ile Ser Cys Asn Asn Ser Gly Lys Asp Gly
1               5                   10                  15

Asn Ser Ala Ser
            20

<210> SEQ ID NO 78
<211> LENGTH: 15
<212> TYPE: PRT
<213> ORGANISM: Borrelia burgdorferi
```

```
<400> SEQUENCE: 78

Phe Ile Ser Cys Asn Asn Ser Gly Lys Asp Gly Asn Thr Ser Ala
1               5                   10                  15

<210> SEQ ID NO 79
<211> LENGTH: 14
<212> TYPE: PRT
<213> ORGANISM: Borrelia sp.

<400> SEQUENCE: 79

Phe Leu Phe Ile Ser Cys Asn Asn Ser Gly Lys Asp Gly Asn
1               5                   10

<210> SEQ ID NO 80
<211> LENGTH: 15
<212> TYPE: PRT
<213> ORGANISM: Borrelia burgdorferi

<400> SEQUENCE: 80

Met Thr Leu Phe Leu Phe Ile Ser Cys Asn Asn Ser Gly Lys Asp
1               5                   10                  15

<210> SEQ ID NO 81
<211> LENGTH: 19
<212> TYPE: PRT
<213> ORGANISM: Borrelia sp.

<400> SEQUENCE: 81

Met Thr Leu Phe Leu Phe Ile Ser Cys Asn Asn Ser Gly Lys Gly Gly
1               5                   10                  15

Asp Ser Ala

<210> SEQ ID NO 82
<211> LENGTH: 19
<212> TYPE: PRT
<213> ORGANISM: Borrelia sp.

<400> SEQUENCE: 82

Met Thr Leu Phe Leu Phe Ile Ser Cys Asn Asn Ser Gly Lys Asp Gly
1               5                   10                  15

Asn Ser Ala

<210> SEQ ID NO 83
<211> LENGTH: 20
<212> TYPE: PRT
<213> ORGANISM: Borrelia sp.

<400> SEQUENCE: 83

Met Thr Leu Leu Leu Phe Ile Ser Ser Asn Thr Ser Gly Lys Asp Gly
1               5                   10                  15

Asn Ser Ser Ala
            20

<210> SEQ ID NO 84
<211> LENGTH: 20
<212> TYPE: PRT
<213> ORGANISM: Borrelia sp.

<400> SEQUENCE: 84

Met Thr Leu Phe Leu Phe Ile Ser Cys Asn Asn Ser Gly Lys Asp Gly
1               5                   10                  15

Asn Ala Ser Ala
```

20

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Ala
<220> FEATURE:
<221> NAME/KEY: MOD_RES
<222> LOCATION: (13)..(13)
<223> OTHER INFORMATION: Ile or Val

<400> SEQUENCE: 85

Lys Phe Tyr Xaa Ser Leu Arg Leu Glu Val Arg Lys Xaa Glu Gln
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Ile
<220> FEATURE:
<221> NAME/KEY: MOD_RES
<222> LOCATION: (2)..(2)
<223> OTHER INFORMATION: Phe, Ile or Leu
<220> FEATURE:
<221> NAME/KEY: MOD_RES
<222> LOCATION: (3)..(3)
<223> OTHER INFORMATION: Tyr, Phe or Asp
<220> FEATURE:
<221> NAME/KEY: MOD_RES
<222> LOCATION: (4)..(4)
<223> OTHER INFORMATION: Ser or Ala
<220> FEATURE:
<221> NAME/KEY: MOD_RES
<222> LOCATION: (5)..(5)
<223> OTHER INFORMATION: Ser or Asn
<220> FEATURE:
<221> NAME/KEY: MOD_RES
<222> LOCATION: (6)..(6)
<223> OTHER INFORMATION: Leu or Arg
<220> FEATURE:
<221> NAME/KEY: MOD_RES
<222> LOCATION: (7)..(7)
<223> OTHER INFORMATION: Arg, Phe, Asn or Gln
<220> FEATURE:
<221> NAME/KEY: MOD_RES
<222> LOCATION: (8)..(8)
<223> OTHER INFORMATION: Leu, Asn or Tyr
<220> FEATURE:
<221> NAME/KEY: MOD_RES
<222> LOCATION: (9)..(9)
<223> OTHER INFORMATION: Glu or Asp
<220> FEATURE:
<221> NAME/KEY: MOD_RES
<222> LOCATION: (10)..(10)
<223> OTHER INFORMATION: Val, Ala, Ile or Glu
<220> FEATURE:
<221> NAME/KEY: MOD_RES
<222> LOCATION: (11)..(11)
<223> OTHER INFORMATION: Arg, Val, Ile, Lys or Asn
<220> FEATURE:
<221> NAME/KEY: MOD_RES
<222> LOCATION: (13)..(13)

-continued

<223> OTHER INFORMATION: Ile, Ser or Val

<400> SEQUENCE: 86

Xaa Xaa Xaa Xaa Xaa Xaa Xaa Xaa Xaa Xaa Lys Xaa Glu Gln
1               5                   10

<210> SEQ ID NO 87
<211> LENGTH: 15
<212> TYPE: PRT
<213> ORGANISM: Borrelia sp.

<400> SEQUENCE: 87

Lys Phe Tyr Ala Ser Leu Arg Leu Glu Val Arg Lys Ile Glu Gln
1               5                   10                  15

<210> SEQ ID NO 88
<211> LENGTH: 15
<212> TYPE: PRT
<213> ORGANISM: Borrelia sp.

<400> SEQUENCE: 88

Lys Phe Tyr Ala Ser Leu Arg Leu Glu Val Arg Lys Val Glu Gln
1               5                   10                  15

<210> SEQ ID NO 89
<211> LENGTH: 14
<212> TYPE: PRT
<213> ORGANISM: Borrelia sp.

<400> SEQUENCE: 89

Lys Phe Tyr Ser Asn Arg Phe Leu Glu Ile Val Lys Ser Glu
1               5                   10

<210> SEQ ID NO 90
<211> LENGTH: 14
<212> TYPE: PRT
<213> ORGANISM: Borrelia sp.

<400> SEQUENCE: 90

Ile Phe Ser Asn Leu Gln Asn Glu Ala Lys Lys Ile Glu Gln
1               5                   10

<210> SEQ ID NO 91
<211> LENGTH: 15
<212> TYPE: PRT
<213> ORGANISM: Borrelia sp.

<400> SEQUENCE: 91

Lys Phe Tyr Ser Ser Leu Arg Leu Glu Val Arg Lys Val Glu Gln
1               5                   10                  15

<210> SEQ ID NO 92
<211> LENGTH: 12
<212> TYPE: PRT
<213> ORGANISM: Borrelia sp.

<400> SEQUENCE: 92

Phe Tyr Ser Ser Leu Asn Tyr Asp Glu Asn Lys Ile
1               5                   10

<210> SEQ ID NO 93
<211> LENGTH: 11
<212> TYPE: PRT
<213> ORGANISM: Borrelia sp.

<400> SEQUENCE: 93

Lys Phe Tyr Ile Ser Val Lys Leu Glu Tyr Lys
1               5                   10

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Ser
<220> FEATURE:
<221> NAME/KEY: MOD_RES
<222> LOCATION: (6)..(6)
<223> OTHER INFORMATION: Asp or Asn
<220> FEATURE:
<221> NAME/KEY: MOD_RES
<222> LOCATION: (9)..(9)
<223> OTHER INFORMATION: Ile or Thr
<220> FEATURE:
<221> NAME/KEY: MOD_RES
<222> LOCATION: (11)..(11)
<223> OTHER INFORMATION: Tyr or Asp
<220> FEATURE:
<221> NAME/KEY: MOD_RES
<222> LOCATION: (13)..(13)
<223> OTHER INFORMATION: Met or Ile

<400> SEQUENCE: 94

Xaa Phe Ile Ser Cys Xaa Leu Phe Xaa Arg Xaa Glu Xaa Lys Glu
1               5                   10                  15

<210> SEQ ID NO 95
<211> LENGTH: 15
<212> TYPE: PRT
<213> ORGANISM: Borrelia sp.

<400> SEQUENCE: 95

Gly Phe Ile Ser Cys Asp Leu Phe Ile Arg Asp Glu Ile Lys Glu
1               5                   10                  15

<210> SEQ ID NO 96
<211> LENGTH: 15
<212> TYPE: PRT
<213> ORGANISM: Borrelia sp.

<400> SEQUENCE: 96

Ser Phe Ile Ser Cys Asn Leu Phe Thr Arg Asp Glu Ile Lys Glu
1               5                   10                  15

<210> SEQ ID NO 97
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Pro or Ser
<220> FEATURE:
<221> NAME/KEY: MOD_RES
<222> LOCATION: (4)..(4)
<223> OTHER INFORMATION: Met, Ile or Leu
<220> FEATURE:
<221> NAME/KEY: MOD_RES

```
<222> LOCATION: (8)..(8)
<223> OTHER INFORMATION: Gly or Asp
<220> FEATURE:
<221> NAME/KEY: MOD_RES
<222> LOCATION: (10)..(10)
<223> OTHER INFORMATION: Gly or Asp
<220> FEATURE:
<221> NAME/KEY: MOD_RES
<222> LOCATION: (12)..(12)
<223> OTHER INFORMATION: Ile or Val
<220> FEATURE:
<221> NAME/KEY: MOD_RES
<222> LOCATION: (16)..(16)
<223> OTHER INFORMATION: Lys or Asn
<220> FEATURE:
<221> NAME/KEY: MOD_RES
<222> LOCATION: (17)..(17)
<223> OTHER INFORMATION: Gly or Val
<220> FEATURE:
<221> NAME/KEY: MOD_RES
<222> LOCATION: (18)..(18)
<223> OTHER INFORMATION: Lys or Glu
<220> FEATURE:
<221> NAME/KEY: MOD_RES
<222> LOCATION: (19)..(19)
<223> OTHER INFORMATION: Ser or Gly
<220> FEATURE:
<221> NAME/KEY: MOD_RES
<222> LOCATION: (20)..(20)
<223> OTHER INFORMATION: Lys or Asn
<220> FEATURE:
<221> NAME/KEY: MOD_RES
<222> LOCATION: (21)..(21)
<223> OTHER INFORMATION: Val or Ala
<220> FEATURE:
<221> NAME/KEY: MOD_RES
<222> LOCATION: (22)..(22)
<223> OTHER INFORMATION: Ser or Val
<220> FEATURE:
<221> NAME/KEY: MOD_RES
<222> LOCATION: (23)..(23)
<223> OTHER INFORMATION: Arg, Gly or Lys
<220> FEATURE:
<221> NAME/KEY: MOD_RES
<222> LOCATION: (25)..(25)
<223> OTHER INFORMATION: Glu or Asp
<220> FEATURE:
<221> NAME/KEY: MOD_RES
<222> LOCATION: (27)..(27)
<223> OTHER INFORMATION: Tyr, Ser or Phe
<220> FEATURE:
<221> NAME/KEY: MOD_RES
<222> LOCATION: (28)..(28)
<223> OTHER INFORMATION: Ile or Asn

<400> SEQUENCE: 97

Lys Lys Xaa Xaa Asn Lys Lys Xaa Lys Xaa Lys Xaa Ala Arg Lys Xaa
1               5                   10                  15

Xaa Xaa Xaa Xaa Xaa Xaa Xaa Lys Xaa Pro Xaa Xaa His Ser
            20                  25                  30

<210> SEQ ID NO 98
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Lys or Asn
<220> FEATURE:
<221> NAME/KEY: MOD_RES
<222> LOCATION: (3)..(3)
<223> OTHER INFORMATION: Pro, Ser or Asp
```

-continued

```
<220> FEATURE:
<221> NAME/KEY: MOD_RES
<222> LOCATION: (4)..(4)
<223> OTHER INFORMATION: Met, Ile or Leu
<220> FEATURE:
<221> NAME/KEY: MOD_RES
<222> LOCATION: (5)..(5)
<223> OTHER INFORMATION: Asn, Ser, Asp or Thr
<220> FEATURE:
<221> NAME/KEY: MOD_RES
<222> LOCATION: (6)..(6)
<223> OTHER INFORMATION: Lys or Asn
<220> FEATURE:
<221> NAME/KEY: MOD_RES
<222> LOCATION: (7)..(7)
<223> OTHER INFORMATION: Lys, Gln or Glu
<220> FEATURE:
<221> NAME/KEY: MOD_RES
<222> LOCATION: (8)..(8)
<223> OTHER INFORMATION: Gly, Ser or Asp
<220> FEATURE:
<221> NAME/KEY: MOD_RES
<222> LOCATION: (10)..(10)
<223> OTHER INFORMATION: Gly, Ser or Asp
<220> FEATURE:
<221> NAME/KEY: MOD_RES
<222> LOCATION: (11)..(11)
<223> OTHER INFORMATION: Lys, Glu or Ser
<220> FEATURE:
<221> NAME/KEY: MOD_RES
<222> LOCATION: (12)..(12)
<223> OTHER INFORMATION: Ile or Val
<220> FEATURE:
<221> NAME/KEY: MOD_RES
<222> LOCATION: (13)..(13)
<223> OTHER INFORMATION: Ala, Ser or Val
<220> FEATURE:
<221> NAME/KEY: MOD_RES
<222> LOCATION: (14)..(14)
<223> OTHER INFORMATION: Arg or Lys
<220> FEATURE:
<221> NAME/KEY: MOD_RES
<222> LOCATION: (16)..(16)
<223> OTHER INFORMATION: Lys, Gln, Asn or Leu
<220> FEATURE:
<221> NAME/KEY: MOD_RES
<222> LOCATION: (17)..(17)
<223> OTHER INFORMATION: Gly, Arg or Val
<220> FEATURE:
<221> NAME/KEY: MOD_RES
<222> LOCATION: (18)..(18)
<223> OTHER INFORMATION: Lys, Asp, Glu or Asn
<220> FEATURE:
<221> NAME/KEY: MOD_RES
<222> LOCATION: (19)..(19)
<223> OTHER INFORMATION: Ser, Asn, Gly, Ala, Asp or Trp
<220> FEATURE:
<221> NAME/KEY: MOD_RES
<222> LOCATION: (20)..(20)
<223> OTHER INFORMATION: Lys, Asn, Ile, Asp or Arg
<220> FEATURE:
<221> NAME/KEY: MOD_RES
<222> LOCATION: (21)..(21)
<223> OTHER INFORMATION: Val, Ala or Glu
<220> FEATURE:
<221> NAME/KEY: MOD_RES
<222> LOCATION: (22)..(22)
<223> OTHER INFORMATION: Ser, Val, Thr or Phe
<220> FEATURE:
<221> NAME/KEY: MOD_RES
<222> LOCATION: (23)..(23)
<223> OTHER INFORMATION: Arg, Gly or Lys
<220> FEATURE:
<221> NAME/KEY: MOD_RES
<222> LOCATION: (24)..(24)
<223> OTHER INFORMATION: Lys or Gln
<220> FEATURE:
<221> NAME/KEY: MOD_RES
<222> LOCATION: (25)..(25)
```

```
<223> OTHER INFORMATION: Glu or Asp
<220> FEATURE:
<221> NAME/KEY: MOD_RES
<222> LOCATION: (27)..(27)
<223> OTHER INFORMATION: Tyr, Ser or Phe
<220> FEATURE:
<221> NAME/KEY: MOD_RES
<222> LOCATION: (28)..(28)
<223> OTHER INFORMATION: Ile, Asn, Thr or Val
<220> FEATURE:
<221> NAME/KEY: MOD_RES
<222> LOCATION: (29)..(29)
<223> OTHER INFORMATION: His, Asn or Thr

<400> SEQUENCE: 98

Lys Xaa Xaa Xaa Xaa Xaa Xaa Lys Xaa Xaa Xaa Xaa Lys Xaa
1               5                   10                  15

Xaa Xaa Xaa Xaa Xaa Xaa Xaa Xaa Xaa Pro Xaa Xaa Xaa Ser
            20                  25                  30

<210> SEQ ID NO 99
<211> LENGTH: 30
<212> TYPE: PRT
<213> ORGANISM: Borrelia sp.

<400> SEQUENCE: 99

Lys Asn Ser Met Asn Lys Lys Gly Lys Gly Lys Ile Ala Arg Lys Lys
1               5                   10                  15

Gly Lys Ser Lys Val Ser Arg Lys Glu Pro Ser Ile His Ser
            20                  25                  30

<210> SEQ ID NO 100
<211> LENGTH: 29
<212> TYPE: PRT
<213> ORGANISM: Borrelia sp.

<400> SEQUENCE: 100

Lys Lys Ser Leu Asn Lys Lys Gly Lys Asp Lys Val Ala Arg Lys Lys
1               5                   10                  15

Val Glu Gly Asn Ala Val Lys Lys Asp Pro Phe Asn His
            20                  25

<210> SEQ ID NO 101
<211> LENGTH: 30
<212> TYPE: PRT
<213> ORGANISM: Borrelia sp.

<400> SEQUENCE: 101

Lys Lys Pro Met Asn Lys Lys Gly Lys Gly Lys Ile Ala Arg Lys Asn
1               5                   10                  15

Gly Lys Ser Lys Val Ser Gly Lys Glu Pro Phe Ile His Ser
            20                  25                  30

<210> SEQ ID NO 102
<211> LENGTH: 30
<212> TYPE: PRT
<213> ORGANISM: Borrelia sp.

<400> SEQUENCE: 102

Lys Lys Pro Met Asn Lys Lys Gly Lys Gly Lys Ile Ala Arg Lys Lys
1               5                   10                  15

Val Lys Ser Lys Val Ser Arg Lys Glu Pro Tyr Ile His Ser
            20                  25                  30
```

-continued

```
<210> SEQ ID NO 103
<211> LENGTH: 30
<212> TYPE: PRT
<213> ORGANISM: Borrelia sp.

<400> SEQUENCE: 103

Lys Lys Pro Ile Asn Lys Gln Gly Lys Ser Lys Val Ser Arg Lys Gln
1               5                   10                  15

Gly Lys Ser Asn Val Ser Arg Lys Glu Pro Ser Ile His Ser
            20                  25                  30

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asn or Ser
<220> FEATURE:
<221> NAME/KEY: MOD_RES
<222> LOCATION: (8)..(8)
<223> OTHER INFORMATION: Ile or Val
<220> FEATURE:
<221> NAME/KEY: MOD_RES
<222> LOCATION: (9)..(9)
<223> OTHER INFORMATION: Ser or Ala

<400> SEQUENCE: 104

Thr Ile Leu Val Xaa Leu Leu Xaa Xaa Cys Gly Leu Thr Gly Ala
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile, Leu or Val
<220> FEATURE:
<221> NAME/KEY: MOD_RES
<222> LOCATION: (4)..(4)
<223> OTHER INFORMATION: Val, Ile or Leu
<220> FEATURE:
<221> NAME/KEY: MOD_RES
<222> LOCATION: (5)..(5)
<223> OTHER INFORMATION: Asn or Ser
<220> FEATURE:
<221> NAME/KEY: MOD_RES
<222> LOCATION: (6)..(7)
<223> OTHER INFORMATION: Leu or Phe
<220> FEATURE:
<221> NAME/KEY: MOD_RES
<222> LOCATION: (8)..(8)
<223> OTHER INFORMATION: Ile or Val
<220> FEATURE:
<221> NAME/KEY: MOD_RES
<222> LOCATION: (9)..(9)
<223> OTHER INFORMATION: Ser or Ala
<220> FEATURE:
<221> NAME/KEY: MOD_RES
<222> LOCATION: (11)..(11)
<223> OTHER INFORMATION: Gly or Ser
<220> FEATURE:
<221> NAME/KEY: MOD_RES
<222> LOCATION: (13)..(13)
<223> OTHER INFORMATION: Thr or Lys
```

<400> SEQUENCE: 105

Thr Xaa Leu Xaa Xaa Xaa Xaa Xaa Cys Xaa Leu Xaa Gly Ala
1               5                   10                  15

<210> SEQ ID NO 106
<211> LENGTH: 15
<212> TYPE: PRT
<213> ORGANISM: Borrelia sp.

<400> SEQUENCE: 106

Thr Ile Leu Val Ser Leu Leu Ile Ser Cys Gly Leu Thr Gly Ala
1               5                   10                  15

<210> SEQ ID NO 107
<211> LENGTH: 15
<212> TYPE: PRT
<213> ORGANISM: Borrelia sp.

<400> SEQUENCE: 107

Thr Ile Leu Val Asn Leu Leu Val Ala Cys Gly Leu Thr Gly Ala
1               5                   10                  15

<210> SEQ ID NO 108
<211> LENGTH: 15
<212> TYPE: PRT
<213> ORGANISM: Borrelia sp.

<400> SEQUENCE: 108

Thr Ile Leu Val Ser Leu Leu Val Ala Cys Gly Leu Thr Gly Ala
1               5                   10                  15

<210> SEQ ID NO 109
<211> LENGTH: 11
<212> TYPE: PRT
<213> ORGANISM: Borrelia sp.

<400> SEQUENCE: 109

Val Ser Leu Leu Val Ala Cys Gly Leu Thr Gly
1               5                   10

<210> SEQ ID NO 110
<211> LENGTH: 10
<212> TYPE: PRT
<213> ORGANISM: Borrelia sp.

<400> SEQUENCE: 110

Ile Leu Val Asn Leu Phe Leu Ser Cys Gly
1               5                   10

<210> SEQ ID NO 111
<211> LENGTH: 10
<212> TYPE: PRT
<213> ORGANISM: Borrelia sp.

<400> SEQUENCE: 111

Thr Ile Leu Val Asn Leu Phe Leu Val Ser
1               5                   10

<210> SEQ ID NO 112
<211> LENGTH: 14
<212> TYPE: PRT
<213> ORGANISM: Borrelia sp.

<400> SEQUENCE: 112

Thr Leu Ile Val Gly Leu Leu Val Ala Cys Ser Leu Thr Gly
1               5                   10

<210> SEQ ID NO 113
<211> LENGTH: 9
<212> TYPE: PRT
<213> ORGANISM: Borrelia sp.

<400> SEQUENCE: 113

Ile Leu Val Phe Phe Leu Ile Ser Cys
1               5

<210> SEQ ID NO 114
<211> LENGTH: 10
<212> TYPE: PRT
<213> ORGANISM: Borrelia sp.

<400> SEQUENCE: 114

Thr Val Leu Ile Leu Ile Ser Cys Ser Leu
1               5                   10

<210> SEQ ID NO 115
<211> LENGTH: 14
<212> TYPE: PRT
<213> ORGANISM: Borrelia sp.

<400> SEQUENCE: 115

Thr Leu Leu Val Ser Leu Phe Ile Ala Cys Ser Leu Thr Gly
1               5                   10

<210> SEQ ID NO 116
<211> LENGTH: 15
<212> TYPE: PRT
<213> ORGANISM: Borrelia sp.
<220> FEATURE:
<221> NAME/KEY: MOD_RES
<222> LOCATION: (3)..(3)
<223> OTHER INFORMATION: Glu or Lys
<220> FEATURE:
<221> NAME/KEY: MOD_RES
<222> LOCATION: (6)..(6)
<223> OTHER INFORMATION: Lys or Glu
<220> FEATURE:
<221> NAME/KEY: MOD_RES
<222> LOCATION: (10)..(10)
<223> OTHER INFORMATION: Lys or Asn
<220> FEATURE:
<221> NAME/KEY: MOD_RES
<222> LOCATION: (13)..(13)
<223> OTHER INFORMATION: Asn or Tyr

<400> SEQUENCE: 116

Lys Ile Xaa Phe Ser Xaa Phe Thr Val Xaa Ile Lys Xaa Lys Asp
1               5                   10                  15

<210> SEQ ID NO 117
<211> LENGTH: 15
<212> TYPE: PRT
<213> ORGANISM: Borrelia sp.

<400> SEQUENCE: 117

Lys Ile Lys Phe Ser Lys Phe Thr Val Lys Ile Lys Asn Lys Asp
1               5                   10                  15

<210> SEQ ID NO 118
<211> LENGTH: 14
<212> TYPE: PRT

```
<213> ORGANISM: Borrelia sp.

<400> SEQUENCE: 118

Lys Ile Glu Phe Ser Glu Phe Thr Val Lys Ile Lys Tyr Lys
1               5                   10

<210> SEQ ID NO 119
<211> LENGTH: 13
<212> TYPE: PRT
<213> ORGANISM: Borrelia sp.

<400> SEQUENCE: 119

Ile Lys Phe Ser Glu Phe Thr Val Asn Ile Lys Asn Lys
1               5                   10

<210> SEQ ID NO 120
<211> LENGTH: 13
<212> TYPE: PRT
<213> ORGANISM: Borrelia sp.

<400> SEQUENCE: 120

Ile Lys Phe Ser Glu Phe Thr Val Lys Ile Lys Tyr Lys
1               5                   10

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val or Ile
<220> FEATURE:
<221> NAME/KEY: MOD_RES
<222> LOCATION: (2)..(2)
<223> OTHER INFORMATION: Ser or Gly

<400> SEQUENCE: 121

Xaa Xaa Arg Lys Gly Gly Leu Leu Pro Asp Ile Ile Ile Lys Ile
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val or Ile
<220> FEATURE:
<221> NAME/KEY: MOD_RES
<222> LOCATION: (2)..(2)
<223> OTHER INFORMATION: Ser, Gly or Phe
<220> FEATURE:
<221> NAME/KEY: MOD_RES
<222> LOCATION: (3)..(3)
<223> OTHER INFORMATION: Arg or Ser
<220> FEATURE:
<221> NAME/KEY: MOD_RES
<222> LOCATION: (4)..(4)
<223> OTHER INFORMATION: Lys, Asp or Asn
<220> FEATURE:
<221> NAME/KEY: MOD_RES
<222> LOCATION: (5)..(5)
<223> OTHER INFORMATION: Gly, Ala or Asp
```

```
<220> FEATURE:
<221> NAME/KEY: MOD_RES
<222> LOCATION: (6)..(6)
<223> OTHER INFORMATION: Gly, Asn or Glu
<220> FEATURE:
<221> NAME/KEY: MOD_RES
<222> LOCATION: (7)..(7)
<223> OTHER INFORMATION: Leu, Ile or Phe
<220> FEATURE:
<221> NAME/KEY: MOD_RES
<222> LOCATION: (8)..(8)
<223> OTHER INFORMATION: Leu or Phe
<220> FEATURE:
<221> NAME/KEY: MOD_RES
<222> LOCATION: (9)..(9)
<223> OTHER INFORMATION: Pro, Ser or Ala
<220> FEATURE:
<221> NAME/KEY: MOD_RES
<222> LOCATION: (10)..(10)
<223> OTHER INFORMATION: Asp or Glu
<220> FEATURE:
<221> NAME/KEY: MOD_RES
<222> LOCATION: (11)..(11)
<223> OTHER INFORMATION: Ile or Leu

<400> SEQUENCE: 122

Xaa Xaa Xaa Xaa Xaa Xaa Xaa Xaa Xaa Xaa Xaa Ile Ile Lys Ile
1               5                   10                  15

<210> SEQ ID NO 123
<211> LENGTH: 15
<212> TYPE: PRT
<213> ORGANISM: Borrelia sp.

<400> SEQUENCE: 123

Ile Gly Arg Lys Gly Gly Leu Leu Pro Asp Ile Ile Ile Lys Ile
1               5                   10                  15

<210> SEQ ID NO 124
<211> LENGTH: 15
<212> TYPE: PRT
<213> ORGANISM: Borrelia sp.

<400> SEQUENCE: 124

Val Gly Arg Lys Gly Gly Leu Leu Pro Asp Ile Ile Ile Lys Ile
1               5                   10                  15

<210> SEQ ID NO 125
<211> LENGTH: 15
<212> TYPE: PRT
<213> ORGANISM: Borrelia sp.

<400> SEQUENCE: 125

Val Ser Arg Lys Ala Gly Leu Leu Pro Asp Ile Ile Ile Lys Ile
1               5                   10                  15

<210> SEQ ID NO 126
<211> LENGTH: 15
<212> TYPE: PRT
<213> ORGANISM: Borrelia sp.

<400> SEQUENCE: 126

Val Phe Ser Asn Asp Asn Phe Leu Ser Glu Leu Ile Ile Lys Ile
1               5                   10                  15

<210> SEQ ID NO 127
<211> LENGTH: 15
<212> TYPE: PRT
<213> ORGANISM: Borrelia sp.
```

<400> SEQUENCE: 127

Val Phe Ser Asn Asp Asn Phe Leu Ser Glu Leu Ile Ile Lys Ile
1               5                   10                  15

<210> SEQ ID NO 128
<211> LENGTH: 10
<212> TYPE: PRT
<213> ORGANISM: Borrelia sp.

<400> SEQUENCE: 128

Lys Ala Gly Ile Phe Pro Asp Leu Ile Ile
1               5                   10

<210> SEQ ID NO 129
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu or Gln
<220> FEATURE:
<221> NAME/KEY: MOD_RES
<222> LOCATION: (4)..(4)
<223> OTHER INFORMATION: Asp or Glu
<220> FEATURE:
<221> NAME/KEY: MOD_RES
<222> LOCATION: (5)..(5)
<223> OTHER INFORMATION: Val or Thr
<220> FEATURE:
<221> NAME/KEY: MOD_RES
<222> LOCATION: (6)..(7)
<223> OTHER INFORMATION: Pro or Ser
<220> FEATURE:
<221> NAME/KEY: MOD_RES
<222> LOCATION: (9)..(9)
<223> OTHER INFORMATION: Thr or Ser
<220> FEATURE:
<221> NAME/KEY: MOD_RES
<222> LOCATION: (10)..(10)
<223> OTHER INFORMATION: Phe or Ile
<220> FEATURE:
<221> NAME/KEY: MOD_RES
<222> LOCATION: (12)..(12)
<223> OTHER INFORMATION: Val or Ile
<220> FEATURE:
<221> NAME/KEY: MOD_RES
<222> LOCATION: (13)..(13)
<223> OTHER INFORMATION: Lys or Arg

<400> SEQUENCE: 129

Asn Thr Xaa Xaa Xaa Xaa Xaa Lys Xaa Xaa Val Xaa Xaa Leu Ala Leu
1               5                   10                  15

Gly Tyr Ala Glu
            20

<210> SEQ ID NO 130
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Leu or Gln
<220> FEATURE:

```
<221> NAME/KEY: MOD_RES
<222> LOCATION: (4)..(4)
<223> OTHER INFORMATION: Asp or Glu
<220> FEATURE:
<221> NAME/KEY: MOD_RES
<222> LOCATION: (5)..(5)
<223> OTHER INFORMATION: Val or Thr
<220> FEATURE:
<221> NAME/KEY: MOD_RES
<222> LOCATION: (6)..(7)
<223> OTHER INFORMATION: Pro or Ser
<220> FEATURE:
<221> NAME/KEY: MOD_RES
<222> LOCATION: (8)..(8)
<223> OTHER INFORMATION: Lys or Arg
<220> FEATURE:
<221> NAME/KEY: MOD_RES
<222> LOCATION: (9)..(9)
<223> OTHER INFORMATION: Thr or Asp
<220> FEATURE:
<221> NAME/KEY: MOD_RES
<222> LOCATION: (12)..(12)
<223> OTHER INFORMATION: Val or Ile
<220> FEATURE:
<221> NAME/KEY: MOD_RES
<222> LOCATION: (13)..(13)
<223> OTHER INFORMATION: Lys or Arg

<400> SEQUENCE: 130

Asn Thr Xaa Xaa Xaa Xaa Xaa Xaa Xaa Phe Val Xaa Xaa Leu Ala Leu
1               5                   10                  15

Gly Tyr Ala Glu
            20

<210> SEQ ID NO 131
<211> LENGTH: 19
<212> TYPE: PRT
<213> ORGANISM: Borrelia sp.

<400> SEQUENCE: 131

Thr Gln Asp Thr Pro Pro Lys Thr Phe Val Ile Lys Leu Ala Leu Gly
1               5                   10                  15

Tyr Ala Glu

<210> SEQ ID NO 132
<211> LENGTH: 18
<212> TYPE: PRT
<213> ORGANISM: Borrelia sp.

<400> SEQUENCE: 132

Thr Gln Asp Thr Pro Pro Lys Thr Phe Val Ile Lys Leu Ala Leu Gly
1               5                   10                  15

Tyr Ala

<210> SEQ ID NO 133
<211> LENGTH: 13
<212> TYPE: PRT
<213> ORGANISM: Borrelia sp.

<400> SEQUENCE: 133

Thr Leu Glu Val Ser Ser Lys Ser Ile Val Val Arg Leu
1               5                   10

<210> SEQ ID NO 134
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr or Gly
<220> FEATURE:
<221> NAME/KEY: MOD_RES
<222> LOCATION: (2)..(2)
<223> OTHER INFORMATION: Phe, Leu or Tyr
<220> FEATURE:
<221> NAME/KEY: MOD_RES
<222> LOCATION: (3)..(3)
<223> OTHER INFORMATION: Tyr or Ile
<220> FEATURE:
<221> NAME/KEY: MOD_RES
<222> LOCATION: (4)..(4)
<223> OTHER INFORMATION: Ala or Ser
<220> FEATURE:
<221> NAME/KEY: MOD_RES
<222> LOCATION: (5)..(5)
<223> OTHER INFORMATION: Phe or Leu
<220> FEATURE:
<221> NAME/KEY: MOD_RES
<222> LOCATION: (7)..(7)
<223> OTHER INFORMATION: Thr or Met
<220> FEATURE:
<221> NAME/KEY: MOD_RES
<222> LOCATION: (8)..(8)
<223> OTHER INFORMATION: His, Thr, Lys or Asn
<220> FEATURE:
<221> NAME/KEY: MOD_RES
<222> LOCATION: (9)..(9)
<223> OTHER INFORMATION: Ile or Val
<220> FEATURE:
<221> NAME/KEY: MOD_RES
<222> LOCATION: (14)..(14)
<223> OTHER INFORMATION: Asn or Asp

<400> SEQUENCE: 134

Xaa Xaa Xaa Xaa Xaa Asn Xaa Xaa Xaa Lys Pro Leu Asp Xaa
1               5                   10

<210> SEQ ID NO 135
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr or Gly
<220> FEATURE:
<221> NAME/KEY: MOD_RES
<222> LOCATION: (2)..(2)
<223> OTHER INFORMATION: Phe, Leu or Tyr
<220> FEATURE:
<221> NAME/KEY: MOD_RES
<222> LOCATION: (3)..(3)
<223> OTHER INFORMATION: Tyr, Phe, Ile or Leu
<220> FEATURE:
<221> NAME/KEY: MOD_RES
<222> LOCATION: (4)..(4)
<223> OTHER INFORMATION: Ala, Arg, Lys or Ser
<220> FEATURE:
<221> NAME/KEY: MOD_RES
<222> LOCATION: (5)..(5)
<223> OTHER INFORMATION: Phe or Leu
<220> FEATURE:
<221> NAME/KEY: MOD_RES
<222> LOCATION: (7)..(7)
<223> OTHER INFORMATION: Thr or Met
<220> FEATURE:
<221> NAME/KEY: MOD_RES
<222> LOCATION: (8)..(8)
```

```
<223> OTHER INFORMATION: His, Thr, Lys or Asn
<220> FEATURE:
<221> NAME/KEY: MOD_RES
<222> LOCATION: (9)..(9)
<223> OTHER INFORMATION: Ile, Val or Ala
<220> FEATURE:
<221> NAME/KEY: MOD_RES
<222> LOCATION: (13)..(13)
<223> OTHER INFORMATION: Asp or Asn

<400> SEQUENCE: 135

Xaa Xaa Xaa Xaa Xaa Asn Xaa Xaa Xaa Lys Pro Leu Xaa Asn
1               5                   10

<210> SEQ ID NO 136
<211> LENGTH: 15
<212> TYPE: PRT
<213> ORGANISM: Borrelia sp.

<400> SEQUENCE: 136

Ile Tyr Phe Tyr Ala Phe Asn Thr Thr Val Lys Pro Leu Asp Asn
1               5                   10                  15

<210> SEQ ID NO 137
<211> LENGTH: 15
<212> TYPE: PRT
<213> ORGANISM: Borrelia sp.

<400> SEQUENCE: 137

Ile Tyr Phe Tyr Ala Phe Asn Thr Lys Ala Lys Pro Leu Asp Asn
1               5                   10                  15

<210> SEQ ID NO 138
<211> LENGTH: 15
<212> TYPE: PRT
<213> ORGANISM: Borrelia sp.

<400> SEQUENCE: 138

Ile Tyr Leu Tyr Ser Phe Asn Thr Lys Ile Lys Pro Leu Asp Asp
1               5                   10                  15

<210> SEQ ID NO 139
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (2)..(2)
<223> OTHER INFORMATION: Lys or Glu
<220> FEATURE:
<221> NAME/KEY: MOD_RES
<222> LOCATION: (3)..(3)
<223> OTHER INFORMATION: Ile, Val or Gly
<220> FEATURE:
<221> NAME/KEY: MOD_RES
<222> LOCATION: (4)..(4)
<223> OTHER INFORMATION: Cys, Ala or Tyr
<220> FEATURE:
<221> NAME/KEY: MOD_RES
<222> LOCATION: (5)..(5)
<223> OTHER INFORMATION: Glu, Ala, Ser, Asn or Thr
<220> FEATURE:
<221> NAME/KEY: MOD_RES
<222> LOCATION: (7)..(7)
```

```
<223> OTHER INFORMATION: Ile or Leu
<220> FEATURE:
<221> NAME/KEY: MOD_RES
<222> LOCATION: (9)..(9)
<223> OTHER INFORMATION: Asn, Ser or Glu
<220> FEATURE:
<221> NAME/KEY: MOD_RES
<222> LOCATION: (11)..(11)
<223> OTHER INFORMATION: Trp or Phe
<220> FEATURE:
<221> NAME/KEY: MOD_RES
<222> LOCATION: (14)..(14)
<223> OTHER INFORMATION: Asn, Ile or Val
<220> FEATURE:
<221> NAME/KEY: MOD_RES
<222> LOCATION: (18)..(18)
<223> OTHER INFORMATION: Asp or Asn
<220> FEATURE:
<221> NAME/KEY: MOD_RES
<222> LOCATION: (19)..(19)
<223> OTHER INFORMATION: Val, Ile or Leu
<220> FEATURE:
<221> NAME/KEY: MOD_RES
<222> LOCATION: (20)..(20)
<223> OTHER INFORMATION: Glu or Gln

<400> SEQUENCE: 139

Xaa Xaa Xaa Xaa Xaa Phe Xaa Gln Xaa Gln Xaa Lys Lys Xaa Leu Asn
1               5                   10                  15

Ile Xaa Xaa Xaa
            20

<210> SEQ ID NO 140
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (2)..(2)
<223> OTHER INFORMATION: Lys or Glu
<220> FEATURE:
<221> NAME/KEY: MOD_RES
<222> LOCATION: (3)..(3)
<223> OTHER INFORMATION: Ile, Val or Gly
<220> FEATURE:
<221> NAME/KEY: MOD_RES
<222> LOCATION: (4)..(4)
<223> OTHER INFORMATION: Cys, Ala or Tyr
<220> FEATURE:
<221> NAME/KEY: MOD_RES
<222> LOCATION: (5)..(5)
<223> OTHER INFORMATION: Glu, Ala, Ser, Asn or Thr
<220> FEATURE:
<221> NAME/KEY: MOD_RES
<222> LOCATION: (7)..(7)
<223> OTHER INFORMATION: Ile or Leu
<220> FEATURE:
<221> NAME/KEY: MOD_RES
<222> LOCATION: (8)..(8)
<223> OTHER INFORMATION: Gln or Glu
<220> FEATURE:
<221> NAME/KEY: MOD_RES
<222> LOCATION: (9)..(9)
<223> OTHER INFORMATION: Asn, Ser or Glu
<220> FEATURE:
<221> NAME/KEY: MOD_RES
<222> LOCATION: (11)..(11)
<223> OTHER INFORMATION: Trp, Glu, Phe or Lys
<220> FEATURE:
```

```
<221> NAME/KEY: MOD_RES
<222> LOCATION: (12)..(12)
<223> OTHER INFORMATION: Lys, Asn or Ile
<220> FEATURE:
<221> NAME/KEY: MOD_RES
<222> LOCATION: (13)..(13)
<223> OTHER INFORMATION: Lys or Asn
<220> FEATURE:
<221> NAME/KEY: MOD_RES
<222> LOCATION: (14)..(14)
<223> OTHER INFORMATION: Asn, Ile or Val
<220> FEATURE:
<221> NAME/KEY: MOD_RES
<222> LOCATION: (18)..(18)
<223> OTHER INFORMATION: Asp or Asn
<220> FEATURE:
<221> NAME/KEY: MOD_RES
<222> LOCATION: (19)..(19)
<223> OTHER INFORMATION: Val, Ile or Leu
<220> FEATURE:
<221> NAME/KEY: MOD_RES
<222> LOCATION: (20)..(20)
<223> OTHER INFORMATION: Glu, Ala or Gln

<400> SEQUENCE: 140

Xaa Xaa Xaa Xaa Xaa Phe Xaa Xaa Xaa Gln Xaa Xaa Xaa Xaa Leu Asn
1               5                   10                  15

Ile Xaa Xaa Xaa
            20

<210> SEQ ID NO 141
<211> LENGTH: 20
<212> TYPE: PRT
<213> ORGANISM: Borrelia sp.

<400> SEQUENCE: 141

Lys Lys Ile Cys Glu Phe Ile Gln Asn Gln Trp Lys Lys Asn Leu Asn
1               5                   10                  15

Ile Asn Val Glu
            20

<210> SEQ ID NO 142
<211> LENGTH: 20
<212> TYPE: PRT
<213> ORGANISM: Borrelia sp.

<400> SEQUENCE: 142

Lys Lys Ile Cys Glu Phe Ile Gln Asn Gln Trp Lys Lys Ile Leu Asn
1               5                   10                  15

Ile Asp Val Glu
            20

<210> SEQ ID NO 143
<211> LENGTH: 20
<212> TYPE: PRT
<213> ORGANISM: Borrelia sp.

<400> SEQUENCE: 143

Arg Lys Ile Ala Glu Phe Ile Gln Asn Gln Trp Lys Lys Asn Leu Asn
1               5                   10                  15

Ile Asn Val Gln
            20

<210> SEQ ID NO 144
<211> LENGTH: 19
<212> TYPE: PRT
<213> ORGANISM: Borrelia sp.
```

<400> SEQUENCE: 144

Lys Lys Ile Ala Ala Phe Ile Gln Asn Gln Trp Lys Lys Ile Leu Asn
1               5                   10                  15

Ile Asn Leu

<210> SEQ ID NO 145
<211> LENGTH: 20
<212> TYPE: PRT
<213> ORGANISM: Borrelia sp.

<400> SEQUENCE: 145

Lys Glu Val Ala Ser Phe Ile Gln Ser Gln Trp Lys Lys Val Leu Asn
1               5                   10                  15

Ile Asp Val Glu
            20

<210> SEQ ID NO 146
<211> LENGTH: 19
<212> TYPE: PRT
<213> ORGANISM: Borrelia sp.

<400> SEQUENCE: 146

Lys Lys Val Ala Thr Phe Ile Gln Asn Gln Trp Lys Lys Ile Leu Asn
1               5                   10                  15

Ile Asn Ile

<210> SEQ ID NO 147
<211> LENGTH: 19
<212> TYPE: PRT
<213> ORGANISM: Borrelia sp.

<400> SEQUENCE: 147

Lys Gly Ala Glu Phe Leu Gln Glu Gln Phe Lys Lys Ile Leu Asn Ile
1               5                   10                  15

Lys Ile Glu

<210> SEQ ID NO 148
<211> LENGTH: 20
<212> TYPE: PRT
<213> ORGANISM: Borrelia sp.

<400> SEQUENCE: 148

Lys Lys Ile Ala Glu Phe Ile Gln Asn Gln Trp Lys Lys Asn Leu Asn
1               5                   10                  15

Ile Asp Val Glu
            20

<210> SEQ ID NO 149
<211> LENGTH: 20
<212> TYPE: PRT
<213> ORGANISM: Borrelia sp.

<400> SEQUENCE: 149

Lys Lys Ile Cys Glu Phe Ile Gln Asn Gln Trp Lys Lys Ile Leu Asn
1               5                   10                  15

Ile Asp Val Glu
            20

<210> SEQ ID NO 150
<211> LENGTH: 20

```
<212> TYPE: PRT
<213> ORGANISM: Borrelia sp.

<400> SEQUENCE: 150

Lys Glu Ile Ala Asn Phe Ile Gln Ser Gln Trp Lys Val Leu Asn
1               5                   10                  15

Ile Asp Ile Glu
            20

<210> SEQ ID NO 151
<211> LENGTH: 20
<212> TYPE: PRT
<213> ORGANISM: Borrelia sp.

<400> SEQUENCE: 151

Lys Ile Thr Ala Glu Phe Leu Gln Glu Gln Phe Lys Lys Val Leu Asn
1               5                   10                  15

Ile Asn Val Ala
            20

<210> SEQ ID NO 152
<211> LENGTH: 17
<212> TYPE: PRT
<213> ORGANISM: Borrelia sp.

<400> SEQUENCE: 152

Ala Glu Phe Leu Gln Glu Gln Phe Lys Lys Ile Leu Asn Ile Asn Leu
1               5                   10                  15

Glu

<210> SEQ ID NO 153
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Glu or Asp
<220> FEATURE:
<221> NAME/KEY: MOD_RES
<222> LOCATION: (3)..(3)
<223> OTHER INFORMATION: Leu, Ser or Ile
<220> FEATURE:
<221> NAME/KEY: MOD_RES
<222> LOCATION: (4)..(4)
<223> OTHER INFORMATION: Glu or Asp
<220> FEATURE:
<221> NAME/KEY: MOD_RES
<222> LOCATION: (5)..(5)
<223> OTHER INFORMATION: Ala, Ser, Glu or Ile
<220> FEATURE:
<221> NAME/KEY: MOD_RES
<222> LOCATION: (6)..(6)
<223> OTHER INFORMATION: Lys or Glu
<220> FEATURE:
<221> NAME/KEY: MOD_RES
<222> LOCATION: (10)..(10)
<223> OTHER INFORMATION: Leu or Ile
<220> FEATURE:
<221> NAME/KEY: MOD_RES
<222> LOCATION: (11)..(11)
<223> OTHER INFORMATION: Lys or Glu
<220> FEATURE:
<221> NAME/KEY: MOD_RES
<222> LOCATION: (18)..(18)
<223> OTHER INFORMATION: Glu or Asp
```

<400> SEQUENCE: 153

Xaa Lys Xaa Xaa Xaa Xaa Lys Thr Ser Xaa Xaa Thr Tyr Ser Glu Tyr
1               5                   10                  15

Glu Xaa Gln

<210> SEQ ID NO 154
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asn, Glu or Asp
<220> FEATURE:
<221> NAME/KEY: MOD_RES
<222> LOCATION: (4)..(4)
<223> OTHER INFORMATION: Leu, Ser or Ile
<220> FEATURE:
<221> NAME/KEY: MOD_RES
<222> LOCATION: (5)..(5)
<223> OTHER INFORMATION: Glu or Asp
<220> FEATURE:
<221> NAME/KEY: MOD_RES
<222> LOCATION: (6)..(6)
<223> OTHER INFORMATION: Ala, Ser, Glu or Ile
<220> FEATURE:
<221> NAME/KEY: MOD_RES
<222> LOCATION: (7)..(7)
<223> OTHER INFORMATION: Lys or Glu
<220> FEATURE:
<221> NAME/KEY: MOD_RES
<222> LOCATION: (8)..(8)
<223> OTHER INFORMATION: Lys, Asn or Ser
<220> FEATURE:
<221> NAME/KEY: MOD_RES
<222> LOCATION: (9)..(9)
<223> OTHER INFORMATION: Any amino acid or Thr
<220> FEATURE:
<221> NAME/KEY: MOD_RES
<222> LOCATION: (10)..(10)
<223> OTHER INFORMATION: Any amino acid or Ser
<220> FEATURE:
<221> NAME/KEY: MOD_RES
<222> LOCATION: (11)..(11)
<223> OTHER INFORMATION: Leu, Phe or Ile
<220> FEATURE:
<221> NAME/KEY: MOD_RES
<222> LOCATION: (12)..(12)
<223> OTHER INFORMATION: Lys, Glu, Gly or Thr
<220> FEATURE:
<221> NAME/KEY: MOD_RES
<222> LOCATION: (15)..(15)
<223> OTHER INFORMATION: Ser, Asn or Gly
<220> FEATURE:
<221> NAME/KEY: MOD_RES
<222> LOCATION: (16)..(16)
<223> OTHER INFORMATION: Glu, Asp or Ser
<220> FEATURE:
<221> NAME/KEY: MOD_RES
<222> LOCATION: (19)..(19)
<223> OTHER INFORMATION: Glu or Asp

<400> SEQUENCE: 154

Ile Xaa Lys Xaa Xaa Xaa Xaa Xaa Xaa Xaa Xaa Xaa Thr Tyr Xaa Xaa
1               5                   10                  15

Tyr Glu Xaa Gln
            20

<210> SEQ ID NO 155
<211> LENGTH: 19

```
<212> TYPE: PRT
<213> ORGANISM: Borrelia sp.

<400> SEQUENCE: 155

Ile Glu Lys Leu Glu Ala Lys Lys Thr Ser Leu Lys Thr Tyr Ser Glu
1               5                   10                  15

Tyr Glu Glu

<210> SEQ ID NO 156
<211> LENGTH: 19
<212> TYPE: PRT
<213> ORGANISM: Borrelia sp.

<400> SEQUENCE: 156

Ile Glu Lys Leu Asp Ser Lys Lys Thr Ser Leu Lys Thr Tyr Ser Glu
1               5                   10                  15

Tyr Glu Glu

<210> SEQ ID NO 157
<211> LENGTH: 19
<212> TYPE: PRT
<213> ORGANISM: Borrelia sp.

<400> SEQUENCE: 157

Ile Glu Lys Leu Asp Ser Lys Lys Thr Ser Ile Glu Thr Tyr Ser Glu
1               5                   10                  15

Tyr Glu Glu

<210> SEQ ID NO 158
<211> LENGTH: 18
<212> TYPE: PRT
<213> ORGANISM: Borrelia sp.

<400> SEQUENCE: 158

Ile Asp Lys Ser Asp Ala Lys Lys Thr Ser Leu Lys Thr Tyr Ser Glu
1               5                   10                  15

Tyr Glu

<210> SEQ ID NO 159
<211> LENGTH: 17
<212> TYPE: PRT
<213> ORGANISM: Borrelia sp.

<400> SEQUENCE: 159

Ile Glu Lys Ser Asp Pro Lys Ser Val Ser Leu Lys Thr Tyr Ser Asp
1               5                   10                  15

Tyr

<210> SEQ ID NO 160
<211> LENGTH: 18
<212> TYPE: PRT
<213> ORGANISM: Borrelia sp.

<400> SEQUENCE: 160

Lys Ile Glu Ile Glu Lys Thr Glu Leu Lys Thr Glu Tyr Asn Glu Ile
1               5                   10                  15

Glu Asp

<210> SEQ ID NO 161
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp, Glu, Arg, Asn or Thr
<220> FEATURE:
<221> NAME/KEY: MOD_RES
<222> LOCATION: (3)..(3)
<223> OTHER INFORMATION: Asp, Glu or Asn
<220> FEATURE:
<221> NAME/KEY: MOD_RES
<222> LOCATION: (4)..(4)
<223> OTHER INFORMATION: Any amino acid or Ser
<220> FEATURE:
<221> NAME/KEY: MOD_RES
<222> LOCATION: (5)..(5)
<223> OTHER INFORMATION: Ile, Leu, Phe or Ala
<220> FEATURE:
<221> NAME/KEY: MOD_RES
<222> LOCATION: (9)..(9)
<223> OTHER INFORMATION: Asp, Glu or Asn
<220> FEATURE:
<221> NAME/KEY: MOD_RES
<222> LOCATION: (11)..(11)
<223> OTHER INFORMATION: Glu or Ser
<220> FEATURE:
<221> NAME/KEY: MOD_RES
<222> LOCATION: (12)..(12)
<223> OTHER INFORMATION: Leu, Phe or Ile
<220> FEATURE:
<221> NAME/KEY: MOD_RES
<222> LOCATION: (13)..(13)
<223> OTHER INFORMATION: Lys or Leu
<220> FEATURE:
<221> NAME/KEY: MOD_RES
<222> LOCATION: (14)..(14)
<223> OTHER INFORMATION: Asn, Lys, Ser, Asp or Glu
<220> FEATURE:
<221> NAME/KEY: MOD_RES
<222> LOCATION: (15)..(15)
<223> OTHER INFORMATION: Thr, Ser or Ala

<400> SEQUENCE: 161

Ile Xaa Xaa Xaa Xaa Lys Lys Ile Xaa Glu Xaa Xaa Xaa Xaa Xaa
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp, Glu, Gly, Asn or Thr
<220> FEATURE:
<221> NAME/KEY: MOD_RES
<222> LOCATION: (3)..(3)
<223> OTHER INFORMATION: Asp, Glu or Asn
<220> FEATURE:
<221> NAME/KEY: MOD_RES
<222> LOCATION: (4)..(4)
<223> OTHER INFORMATION: Any amino acid or Ser
<220> FEATURE:
<221> NAME/KEY: MOD_RES
<222> LOCATION: (5)..(5)
<223> OTHER INFORMATION: Ile, Leu, Phe, Val or Ala
<220> FEATURE:
<221> NAME/KEY: MOD_RES
<222> LOCATION: (6)..(6)
<223> OTHER INFORMATION: Lys or Glu
<220> FEATURE:
```

```
<221> NAME/KEY: MOD_RES
<222> LOCATION: (7)..(7)
<223> OTHER INFORMATION: Lys or Asn
<220> FEATURE:
<221> NAME/KEY: MOD_RES
<222> LOCATION: (8)..(8)
<223> OTHER INFORMATION: Ile or Leu
<220> FEATURE:
<221> NAME/KEY: MOD_RES
<222> LOCATION: (9)..(9)
<223> OTHER INFORMATION: Asp, Glu or Asn
<220> FEATURE:
<221> NAME/KEY: MOD_RES
<222> LOCATION: (10)..(10)
<223> OTHER INFORMATION: Glu or Asp
<220> FEATURE:
<221> NAME/KEY: MOD_RES
<222> LOCATION: (11)..(11)
<223> OTHER INFORMATION: Glu, Ala or Ser
<220> FEATURE:
<221> NAME/KEY: MOD_RES
<222> LOCATION: (12)..(12)
<223> OTHER INFORMATION: Leu, Phe, Ile or Ala
<220> FEATURE:
<221> NAME/KEY: MOD_RES
<222> LOCATION: (13)..(13)
<223> OTHER INFORMATION: Lys or Asn
<220> FEATURE:
<221> NAME/KEY: MOD_RES
<222> LOCATION: (14)..(14)
<223> OTHER INFORMATION: Asn, Lys, Ser, Asp, Glu or Gly
<220> FEATURE:
<221> NAME/KEY: MOD_RES
<222> LOCATION: (15)..(15)
<223> OTHER INFORMATION: Thr, Ser, Val or Ala

<400> SEQUENCE: 162

Ile Xaa Xaa Xaa Xaa Xaa Xaa Xaa Xaa Xaa Xaa Xaa Xaa Xaa Xaa
1               5                   10                  15

<210> SEQ ID NO 163
<211> LENGTH: 15
<212> TYPE: PRT
<213> ORGANISM: Borrelia sp.

<400> SEQUENCE: 163

Ile Asp Asp Ser Ile Lys Lys Ile Glu Glu Glu Leu Lys Asn Thr
1               5                   10                  15

<210> SEQ ID NO 164
<211> LENGTH: 13
<212> TYPE: PRT
<213> ORGANISM: Borrelia sp.

<400> SEQUENCE: 164

Ile Asp Asp Ser Leu Lys Lys Ile Glu Glu Glu Leu Lys
1               5                   10

<210> SEQ ID NO 165
<211> LENGTH: 15
<212> TYPE: PRT
<213> ORGANISM: Borrelia sp.

<400> SEQUENCE: 165

Ile Asp Glu Asn Phe Lys Lys Ile Glu Glu Glu Phe Lys Asp Thr
1               5                   10                  15

<210> SEQ ID NO 166
<211> LENGTH: 15
<212> TYPE: PRT
<213> ORGANISM: Borrelia sp.
```

-continued

<400> SEQUENCE: 166

Ile Thr Asn Ser Leu Lys Lys Ile Glu Glu Leu Lys Glu Ala
1               5                   10                  15

<210> SEQ ID NO 167
<211> LENGTH: 14
<212> TYPE: PRT
<213> ORGANISM: Borrelia sp.

<400> SEQUENCE: 167

Ile Asp Glu Asn Phe Lys Lys Ile Glu Glu Phe Lys Asp
1               5                   10

<210> SEQ ID NO 168
<211> LENGTH: 14
<212> TYPE: PRT
<213> ORGANISM: Borrelia sp.

<400> SEQUENCE: 168

Ile Glu Asp Leu Ile Lys Lys Ile Asn Glu Glu Ile Leu Asn
1               5                   10

<210> SEQ ID NO 169
<211> LENGTH: 12
<212> TYPE: PRT
<213> ORGANISM: Borrelia sp.

<400> SEQUENCE: 169

Ile Asn Asp Ser Leu Lys Lys Ile Glu Glu Glu Leu
1               5                   10

<210> SEQ ID NO 170
<211> LENGTH: 14
<212> TYPE: PRT
<213> ORGANISM: Borrelia sp.

<400> SEQUENCE: 170

Asp Glu Asn Phe Lys Lys Ile Glu Glu Glu Phe Lys Asp Thr
1               5                   10

<210> SEQ ID NO 171
<211> LENGTH: 13
<212> TYPE: PRT
<213> ORGANISM: Borrelia sp.

<400> SEQUENCE: 171

Asp Glu Asn Phe Lys Lys Ile Glu Glu Glu Phe Lys Asp
1               5                   10

<210> SEQ ID NO 172
<211> LENGTH: 14
<212> TYPE: PRT
<213> ORGANISM: Borrelia sp.

<400> SEQUENCE: 172

Ile Asp Asp Ala Leu Glu Asn Ile Asn Glu Glu Leu Lys Lys
1               5                   10

<210> SEQ ID NO 173
<211> LENGTH: 13
<212> TYPE: PRT
<213> ORGANISM: Borrelia sp.

<400> SEQUENCE: 173

```
Ile Arg Glu Ser Ala Lys Lys Ile Asp Glu Ser Leu Lys
1               5                   10

<210> SEQ ID NO 174
<211> LENGTH: 13
<212> TYPE: PRT
<213> ORGANISM: Borrelia sp.

<400> SEQUENCE: 174

Glu Asp Leu Ile Lys Lys Ile Asn Glu Glu Ile Leu Asn
1               5                   10

<210> SEQ ID NO 175
<211> LENGTH: 12
<212> TYPE: PRT
<213> ORGANISM: Borrelia sp.

<400> SEQUENCE: 175

Asn Val Ile Lys Arg Ile Glu Glu Glu Ala Lys Asn
1               5                   10

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly or Ser
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (6)..(6)
<223> OTHER INFORMATION: Arg or Lys
<220> FEATURE:
<221> NAME/KEY: MOD_RES
<222> LOCATION: (8)..(8)
<223> OTHER INFORMATION: Ile, Lys or Arg
<220> FEATURE:
<221> NAME/KEY: MOD_RES
<222> LOCATION: (9)..(9)
<223> OTHER INFORMATION: Arg, Lys or Ala
<220> FEATURE:
<221> NAME/KEY: MOD_RES
<222> LOCATION: (10)..(10)
<223> OTHER INFORMATION: Tyr or Phe
<220> FEATURE:
<221> NAME/KEY: MOD_RES
<222> LOCATION: (12)..(12)
<223> OTHER INFORMATION: Arg or Lys
<220> FEATURE:
<221> NAME/KEY: MOD_RES
<222> LOCATION: (13)..(13)
<223> OTHER INFORMATION: Arg, His or Cys
<220> FEATURE:
<221> NAME/KEY: MOD_RES
<222> LOCATION: (14)..(14)
<223> OTHER INFORMATION: Val, Thr, Ile or Ala

<400> SEQUENCE: 176

Asp Thr Xaa Xaa Glu Xaa Ser Xaa Xaa Xaa Arg Xaa Xaa Xaa Tyr
1               5                   10                  15

<210> SEQ ID NO 177
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly or Ser
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Glu or Asp
<220> FEATURE:
<221> NAME/KEY: MOD_RES
<222> LOCATION: (6)..(6)
<223> OTHER INFORMATION: Arg or Lys
<220> FEATURE:
<221> NAME/KEY: MOD_RES
<222> LOCATION: (7)..(7)
<223> OTHER INFORMATION: Ser or Ala
<220> FEATURE:
<221> NAME/KEY: MOD_RES
<222> LOCATION: (8)..(8)
<223> OTHER INFORMATION: Ile, Lys or Arg
<220> FEATURE:
<221> NAME/KEY: MOD_RES
<222> LOCATION: (9)..(9)
<223> OTHER INFORMATION: Arg, Lys or Ala
<220> FEATURE:
<221> NAME/KEY: MOD_RES
<222> LOCATION: (10)..(10)
<223> OTHER INFORMATION: Tyr or Phe
<220> FEATURE:
<221> NAME/KEY: MOD_RES
<222> LOCATION: (12)..(12)
<223> OTHER INFORMATION: Arg or Lys
<220> FEATURE:
<221> NAME/KEY: MOD_RES
<222> LOCATION: (13)..(13)
<223> OTHER INFORMATION: Arg, His, Cys or Asn
<220> FEATURE:
<221> NAME/KEY: MOD_RES
<222> LOCATION: (14)..(14)
<223> OTHER INFORMATION: Val, Thr, Ile or Ala

<400> SEQUENCE: 177

Asp Thr Xaa Xaa Xaa Xaa Xaa Xaa Xaa Arg Xaa Xaa Xaa Tyr
1               5                   10                  15

<210> SEQ ID NO 178
<211> LENGTH: 15
<212> TYPE: PRT
<213> ORGANISM: Borrelia sp.

<400> SEQUENCE: 178

Asp Thr Ser Ser Glu Arg Ser Ile Arg Tyr Arg Arg His Val Tyr
1               5                   10                  15

<210> SEQ ID NO 179
<211> LENGTH: 15
<212> TYPE: PRT
<213> ORGANISM: Borrelia sp.

<400> SEQUENCE: 179

Asp Thr Gly Thr Glu Arg Ser Ile Arg Tyr Arg Lys Arg Thr Tyr
1               5                   10                  15

<210> SEQ ID NO 180
```

```
<211> LENGTH: 15
<212> TYPE: PRT
<213> ORGANISM: Borrelia sp.

<400> SEQUENCE: 180

Asp Thr Gly Thr Glu Arg Ser Ile Arg Phe Arg Arg His Thr Tyr
1               5                   10                  15

<210> SEQ ID NO 181
<211> LENGTH: 15
<212> TYPE: PRT
<213> ORGANISM: Borrelia sp.

<400> SEQUENCE: 181

Asp Thr Gly Thr Glu Arg Ser Ile Lys Phe Arg Arg His Thr Tyr
1               5                   10                  15

<210> SEQ ID NO 182
<211> LENGTH: 15
<212> TYPE: PRT
<213> ORGANISM: Borrelia sp.

<400> SEQUENCE: 182

Asp Thr Gly Thr Glu Arg Ser Lys Ala Tyr Arg Lys Arg Ala Tyr
1               5                   10                  15

<210> SEQ ID NO 183
<211> LENGTH: 15
<212> TYPE: PRT
<213> ORGANISM: Borrelia sp.

<400> SEQUENCE: 183

Asp Thr Gly Thr Glu Arg Ser Ile Arg Tyr Arg Arg Arg Thr Tyr
1               5                   10                  15

<210> SEQ ID NO 184
<211> LENGTH: 12
<212> TYPE: PRT
<213> ORGANISM: Borrelia sp.

<400> SEQUENCE: 184

Thr Glu Arg Ser Ile Arg Tyr Arg Lys Arg Thr Tyr
1               5                   10

<210> SEQ ID NO 185
<211> LENGTH: 12
<212> TYPE: PRT
<213> ORGANISM: Borrelia sp.

<400> SEQUENCE: 185

Thr Glu Arg Ser Ile Arg Tyr Arg Arg His Thr Tyr
1               5                   10

<210> SEQ ID NO 186
<211> LENGTH: 12
<212> TYPE: PRT
<213> ORGANISM: Borrelia sp.

<400> SEQUENCE: 186

Thr Glu Arg Ser Ile Arg Phe Arg Arg His Thr Tyr
1               5                   10

<210> SEQ ID NO 187
<211> LENGTH: 12
<212> TYPE: PRT
```

```
<213> ORGANISM: Borrelia sp.

<400> SEQUENCE: 187

Ser Glu Lys Ala Arg Lys Tyr Arg Arg Asn Val Tyr
1               5                   10

<210> SEQ ID NO 188
<211> LENGTH: 12
<212> TYPE: PRT
<213> ORGANISM: Borrelia sp.

<400> SEQUENCE: 188

Thr Glu Arg Ser Lys Ala Tyr Arg Lys Arg Ala Tyr
1               5                   10

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala or Val
<220> FEATURE:
<221> NAME/KEY: MOD_RES
<222> LOCATION: (7)..(7)
<223> OTHER INFORMATION: Leu or Ile
<220> FEATURE:
<221> NAME/KEY: MOD_RES
<222> LOCATION: (9)..(9)
<223> OTHER INFORMATION: Leu or Ile
<220> FEATURE:
<221> NAME/KEY: MOD_RES
<222> LOCATION: (10)..(10)
<223> OTHER INFORMATION: Ala or Thr

<400> SEQUENCE: 189

Phe Glu Asp Xaa Met Lys Xaa Gly Xaa Xaa Leu Tyr Leu Asp Tyr
1               5                   10                  15

<210> SEQ ID NO 190
<211> LENGTH: 15
<212> TYPE: PRT
<213> ORGANISM: Borrelia sp.

<400> SEQUENCE: 190

Phe Glu Asp Ala Met Lys Leu Gly Ile Ala Leu Tyr Leu Asp Tyr
1               5                   10                  15

<210> SEQ ID NO 191
<211> LENGTH: 15
<212> TYPE: PRT
<213> ORGANISM: Borrelia sp.

<400> SEQUENCE: 191

Phe Glu Asp Ala Met Lys Ile Gly Ile Ala Leu Tyr Leu Asp Tyr
1               5                   10                  15

<210> SEQ ID NO 192
<211> LENGTH: 15
<212> TYPE: PRT
<213> ORGANISM: Borrelia sp.

<400> SEQUENCE: 192

Phe Glu Asp Ala Met Lys Leu Gly Leu Thr Leu Tyr Leu Asp Tyr
```

```
<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Phe
<220> FEATURE:
<221> NAME/KEY: MOD_RES
<222> LOCATION: (5)..(5)
<223> OTHER INFORMATION: Thr or Ser
<220> FEATURE:
<221> NAME/KEY: MOD_RES
<222> LOCATION: (6)..(6)
<223> OTHER INFORMATION: Thr or Ala
<220> FEATURE:
<221> NAME/KEY: MOD_RES
<222> LOCATION: (9)..(9)
<223> OTHER INFORMATION: Leu or Ile
<220> FEATURE:
<221> NAME/KEY: MOD_RES
<222> LOCATION: (11)..(11)
<223> OTHER INFORMATION: Trp or Ser

<400> SEQUENCE: 193

Leu Xaa Arg Phe Xaa Xaa Ile Ser Xaa Gly Xaa Asp Ser Asn Asn
1               5                   10                  15

<210> SEQ ID NO 194
<211> LENGTH: 11
<212> TYPE: PRT
<213> ORGANISM: Borrelia sp.

<400> SEQUENCE: 194

Leu Phe Arg Phe Ser Ala Ile Ser Ile Gly Ser
1               5                   10

<210> SEQ ID NO 195
<211> LENGTH: 15
<212> TYPE: PRT
<213> ORGANISM: Borrelia sp.

<400> SEQUENCE: 195

Leu Phe Arg Phe Ser Ala Ile Ser Ile Gly Ser Asp Ser Asn Asn
1               5                   10                  15

<210> SEQ ID NO 196
<211> LENGTH: 11
<212> TYPE: PRT
<213> ORGANISM: Borrelia sp.

<400> SEQUENCE: 196

Leu Phe Arg Phe Ser Ala Ile Ser Ile Gly Ser
1               5                   10

<210> SEQ ID NO 197
<211> LENGTH: 15
<212> TYPE: PRT
<213> ORGANISM: Borrelia sp.

<400> SEQUENCE: 197

Leu Ile Arg Phe Ser Ala Ile Ser Leu Gly Ser Asp Ser Asn Asn
1               5                   10                  15
```

<210> SEQ ID NO 198
<211> LENGTH: 15
<212> TYPE: PRT
<213> ORGANISM: Borrelia sp.

<400> SEQUENCE: 198

Leu Ile Arg Phe Thr Ala Ile Ser Ile Gly Trp Asp Ser Asn Asn
1               5                   10                  15

<210> SEQ ID NO 199
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Gly
<220> FEATURE:
<221> NAME/KEY: MOD_RES
<222> LOCATION: (7)..(7)
<223> OTHER INFORMATION: Asn or Asp
<220> FEATURE:
<221> NAME/KEY: MOD_RES
<222> LOCATION: (9)..(9)
<223> OTHER INFORMATION: Phe, Ser or Tyr
<220> FEATURE:
<221> NAME/KEY: MOD_RES
<222> LOCATION: (18)..(18)
<223> OTHER INFORMATION: Gly or Ile

<400> SEQUENCE: 199

Asn Ser Arg Xaa Arg Tyr Xaa Asn Xaa Tyr Lys Lys Glu Ala Asp Phe
1               5                   10                  15

Leu Xaa Ala Ala
            20

<210> SEQ ID NO 200
<211> LENGTH: 20
<212> TYPE: PRT
<213> ORGANISM: Borrelia sp.

<400> SEQUENCE: 200

Asn Ser Arg Ser Arg Tyr Asp Asn Phe Tyr Lys Lys Glu Ala Asp Phe
1               5                   10                  15

Leu Gly Ala Ala
            20

<210> SEQ ID NO 201
<211> LENGTH: 20
<212> TYPE: PRT
<213> ORGANISM: Borrelia sp.

<400> SEQUENCE: 201

Asn Ser Arg Ser Arg Tyr Asn Asn Tyr Tyr Lys Lys Glu Ala Asp Phe
1               5                   10                  15

Leu Gly Ala Ala
            20

<210> SEQ ID NO 202
<211> LENGTH: 20
<212> TYPE: PRT
<213> ORGANISM: Borrelia sp.

```
<400> SEQUENCE: 202

Asn Ser Arg Gly Arg Tyr Asn Asn Ser Tyr Lys Lys Glu Ala Asp Phe
1               5                   10                  15

Leu Ile Ala Ala
            20

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Thr, Glu or Ala
<220> FEATURE:
<221> NAME/KEY: MOD_RES
<222> LOCATION: (4)..(4)
<223> OTHER INFORMATION: Phe or Tyr
<220> FEATURE:
<221> NAME/KEY: MOD_RES
<222> LOCATION: (5)..(5)
<223> OTHER INFORMATION: Asn, Lys or Gly
<220> FEATURE:
<221> NAME/KEY: MOD_RES
<222> LOCATION: (7)..(7)
<223> OTHER INFORMATION: Leu, Val or Ile
<220> FEATURE:
<221> NAME/KEY: MOD_RES
<222> LOCATION: (8)..(8)
<223> OTHER INFORMATION: Leu or Ile
<220> FEATURE:
<221> NAME/KEY: MOD_RES
<222> LOCATION: (11)..(11)
<223> OTHER INFORMATION: Thr or Gly

<400> SEQUENCE: 203

Asn Lys Xaa Xaa Xaa Asn Xaa Xaa Lys Leu Xaa Ile Leu Val Asn
1               5                   10                  15

<210> SEQ ID NO 204
<211> LENGTH: 15
<212> TYPE: PRT
<213> ORGANISM: Borrelia sp.

<400> SEQUENCE: 204

Asn Lys Ala Phe Gly Asn Leu Leu Lys Glu Gly Ile Leu Val Asn
1               5                   10                  15

<210> SEQ ID NO 205
<211> LENGTH: 15
<212> TYPE: PRT
<213> ORGANISM: Borrelia sp.

<400> SEQUENCE: 205

Asn Lys Ile Tyr Lys Asp Leu Leu Lys Ile Ala Ile Leu Val Asn
1               5                   10                  15

<210> SEQ ID NO 206
<211> LENGTH: 15
<212> TYPE: PRT
<213> ORGANISM: Borrelia sp.

<400> SEQUENCE: 206

Asn Lys Thr Tyr Lys Asn Leu Leu Lys Leu Thr Ile Leu Val Asn
1               5                   10                  15
```

<210> SEQ ID NO 207
<211> LENGTH: 15
<212> TYPE: PRT
<213> ORGANISM: Borrelia sp.

<400> SEQUENCE: 207

Asn Lys Thr Phe Asn Asn Val Ile Lys Leu Thr Ile Leu Val Asn
1               5                   10                  15

<210> SEQ ID NO 208
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pro or Ser
<220> FEATURE:
<221> NAME/KEY: MOD_RES
<222> LOCATION: (4)..(4)
<223> OTHER INFORMATION: Leu or Lys
<220> FEATURE:
<221> NAME/KEY: MOD_RES
<222> LOCATION: (5)..(5)
<223> OTHER INFORMATION: Glu, Lys or Gln
<220> FEATURE:
<221> NAME/KEY: MOD_RES
<222> LOCATION: (6)..(6)
<223> OTHER INFORMATION: Ala or Ser
<220> FEATURE:
<221> NAME/KEY: MOD_RES
<222> LOCATION: (8)..(8)
<223> OTHER INFORMATION: Val, Met or Ile
<220> FEATURE:
<221> NAME/KEY: MOD_RES
<222> LOCATION: (9)..(9)
<223> OTHER INFORMATION: Arg, Lys or Gln
<220> FEATURE:
<221> NAME/KEY: MOD_RES
<222> LOCATION: (10)..(10)
<223> OTHER INFORMATION: Ala or Gly
<220> FEATURE:
<221> NAME/KEY: MOD_RES
<222> LOCATION: (11)..(11)
<223> OTHER INFORMATION: Thr or Ile
<220> FEATURE:
<221> NAME/KEY: MOD_RES
<222> LOCATION: (12)..(12)
<223> OTHER INFORMATION: Thr, Glu, Ala, Asp, Lys or Gln

<400> SEQUENCE: 208

Xaa Phe Ile Xaa Xaa Xaa Lys Xaa Xaa Xaa Xaa Xaa Val Ala Glu
1               5                   10                  15

<210> SEQ ID NO 209
<211> LENGTH: 15
<212> TYPE: PRT
<213> ORGANISM: Borrelia sp.

<400> SEQUENCE: 209

Ser Phe Ile Leu Glu Ala Lys Val Arg Ala Thr Thr Val Ala Glu
1               5                   10                  15

<210> SEQ ID NO 210
<211> LENGTH: 15
<212> TYPE: PRT
<213> ORGANISM: Borrelia sp.

<400> SEQUENCE: 210

```
Ser Phe Ile Leu Glu Ala Lys Met Arg Gly Thr Thr Val Ala Glu
1               5                   10                  15

<210> SEQ ID NO 211
<211> LENGTH: 15
<212> TYPE: PRT
<213> ORGANISM: Borrelia sp.

<400> SEQUENCE: 211

Pro Phe Ile Leu Lys Ala Lys Met Arg Gly Thr Glu Val Thr Glu
1               5                   10                  15

<210> SEQ ID NO 212
<211> LENGTH: 14
<212> TYPE: PRT
<213> ORGANISM: Borrelia sp.

<400> SEQUENCE: 212

Phe Ile Lys Gln Ala Lys Val Arg Ala Ile Lys Val Ala Glu
1               5                   10

<210> SEQ ID NO 213
<211> LENGTH: 14
<212> TYPE: PRT
<213> ORGANISM: Borrelia sp.

<400> SEQUENCE: 213

Phe Ile Leu Lys Ala Lys Ile Lys Ala Ile Gln Val Ala Glu
1               5                   10

<210> SEQ ID NO 214
<211> LENGTH: 14
<212> TYPE: PRT
<213> ORGANISM: Borrelia sp.

<400> SEQUENCE: 214

Phe Ile Leu Lys Ala Lys Ile Gln Ala Ile Gln Val Ala Glu
1               5                   10

<210> SEQ ID NO 215
<211> LENGTH: 35
<212> TYPE: PRT
<213> ORGANISM: Borrelia burgdorferi

<400> SEQUENCE: 215

Ser Asp Tyr Tyr Ser Ser Ala Val Asn Ala Ile Tyr Phe Tyr Ser Phe
1               5                   10                  15

Asn Thr His Ile Lys Pro Leu Asp Asn Val Lys Ile Arg Lys Ala Leu
            20                  25                  30

Thr Leu Ala
        35

<210> SEQ ID NO 216
<211> LENGTH: 528
<212> TYPE: PRT
<213> ORGANISM: Borrelia burgdorferi

<400> SEQUENCE: 216

Met Lys Leu Gln Arg Ser Leu Phe Leu Ile Ile Phe Phe Leu Thr Phe
1               5                   10                  15

Leu Cys Cys Asn Asn Lys Glu Arg Lys Glu Gly Val Ser Phe Lys Ile
            20                  25                  30
```

```
Ser Leu Gly Ala Glu Pro Ser Leu Asp Pro Gln Leu Ala Glu Asp
         35                  40                  45

Asn Val Ala Ser Lys Met Ile Asp Thr Met Phe Arg Gly Ile Val Thr
 50                  55                  60

Gly Asp Pro Asn Thr Gly Gly Asn Lys Pro Gly Leu Ala Lys Gly Trp
 65                  70                  75                  80

Asp Ile Ser Ser Asp Gly Thr Val Tyr Thr Phe Asn Leu Arg Glu Lys
                 85                  90                  95

Ile Thr Trp Ser Asp Gly Val Ala Ile Thr Ala Glu Gly Ile Arg Lys
                100                 105                 110

Ser Tyr Leu Arg Ile Leu Asn Lys Glu Thr Gly Ser Lys Tyr Val Glu
        115                 120                 125

Met Val Lys Ser Val Ile Lys Asn Gly Gln Lys Tyr Phe Asp Gly Gln
    130                 135                 140

Val Thr Asp Ser Glu Leu Gly Ile Arg Ala Ile Asp Glu Lys Thr Leu
145                 150                 155                 160

Glu Ile Thr Leu Glu Ser Pro Lys Pro Tyr Phe Ile Asp Met Leu Val
                165                 170                 175

His Gln Ser Phe Ile Pro Val Pro Val His Val Thr Glu Lys Tyr Gly
                180                 185                 190

Gln Asn Trp Thr Asn Pro Glu Asn Met Val Thr Ser Gly Pro Phe Lys
        195                 200                 205

Leu Lys Glu Arg Ile Pro Asn Glu Lys Ile Val Phe Lys Glu Asn Asn
    210                 215                 220

Lys Tyr Tyr Asp Ser Asn Glu Val Glu Leu Glu Glu Ile Thr Phe Tyr
225                 230                 235                 240

Thr Thr Asn Asp Ser Ser Thr Ala Tyr Lys Met Tyr Glu Asn Glu Glu
                245                 250                 255

Leu Asp Ala Ile Phe Gly Ser Ile Pro Pro Asp Leu Ile Lys Asn Leu
                260                 265                 270

Lys Leu Arg Ser Asp Tyr Tyr Ser Ser Ala Val Asn Ala Ile Tyr Phe
        275                 280                 285

Tyr Ser Phe Asn Thr His Ile Lys Pro Leu Asp Asn Val Lys Ile Arg
    290                 295                 300

Lys Ala Leu Thr Leu Ala Ile Asp Arg Glu Thr Leu Thr Tyr Lys Val
305                 310                 315                 320

Leu Asp Asn Gly Thr Thr Pro Thr Arg Arg Ala Thr Pro Asn Phe Ser
                325                 330                 335

Ser Tyr Ser Tyr Ala Lys Ser Leu Glu Leu Phe Asn Pro Glu Ile Ala
                340                 345                 350

Lys Thr Leu Leu Ala Glu Ala Gly Tyr Pro Asn Gly Asn Gly Phe Pro
        355                 360                 365

Ile Leu Lys Leu Lys Tyr Asn Thr Asn Glu Ala Asn Lys Lys Ile Cys
    370                 375                 380

Glu Phe Ile Gln Asn Gln Trp Lys Lys Asn Leu Asn Ile Asp Val Glu
385                 390                 395                 400

Leu Glu Asn Glu Glu Trp Thr Thr Tyr Leu Asn Thr Lys Ala Asn Gly
                405                 410                 415

Asn Tyr Glu Ile Ala Arg Ala Gly Trp Ile Gly Asp Tyr Ala Asp Pro
                420                 425                 430

Leu Thr Phe Leu Ser Ile Phe Thr Gln Gly Tyr Thr Gln Phe Ser Ser
        435                 440                 445

His Asn Tyr Ser Asn Pro Glu Tyr Asn Glu Leu Ile Lys Lys Ser Asp
```

```
                450             455             460
Leu Glu Leu Asp Pro Ile Lys Arg Gln Asp Ile Leu Arg Gln Ala Glu
465                 470                 475                 480

Glu Ile Ile Ile Glu Lys Asp Phe Pro Ile Ala Pro Ile Tyr Ile Tyr
                485                 490                 495

Gly Asn Ser Tyr Leu Phe Arg Asn Asp Lys Trp Thr Gly Trp Asn Thr
                500                 505                 510

Asn Ile Leu Glu Arg Phe Asp Leu Ser Gln Leu Lys Leu Lys Asn Lys
                515                 520                 525

<210> SEQ ID NO 217
<211> LENGTH: 45
<212> TYPE: PRT
<213> ORGANISM: Borrelia sp.

<400> SEQUENCE: 217

Met Thr Leu Phe Leu Phe Ile Ser Cys Asn Asn Ser Gly Lys Asp Gly
1               5                   10                  15

Asn Thr Ser Ala Ala Lys Glu Ala Ile Leu Lys Thr Asn Gly Thr Lys
                20                  25                  30

Thr Lys Gly Pro Val Val Ala Glu Ser Pro Lys Lys Pro
            35                  40                  45

<210> SEQ ID NO 218
<211> LENGTH: 46
<212> TYPE: PRT
<213> ORGANISM: Borrelia sp.

<400> SEQUENCE: 218

Met Thr Leu Phe Leu Phe Ile Ser Cys Asn Asn Ser Gly Lys Asp Gly
1               5                   10                  15

Asn Thr Ser Ala Ala Lys Lys

Asp Lys Gly Pro Val Val Ala Glu Ser Pro Lys Lys Pro
         35                  40                  45

<210> SEQ ID NO 221
<211> LENGTH: 45
<212> TYPE: PRT
<213> ORGANISM: Borrelia sp.

<400> SEQUENCE: 221

Met Thr Leu Phe Leu Phe Ile Ser Cys Asn Asn Ser Gly Lys Asp Gly
1               5                   10                  15

Asn Ala Ser Ala Ala Gln Arg Ala Ile Leu Lys Lys His Ala Asn Lys
            20                  25                  30

Asp Lys Gly Pro Ile Val Ala Glu Ser Pro Lys Lys Pro
         35                  40                  45

<210> SEQ ID NO 222
<211> LENGTH: 45
<212> TYPE: PRT
<213> ORGANISM: Borrelia pacificus

<400> SEQUENCE: 222

Met Thr Leu Phe Leu Phe Ile Ser Cys Asn Asn Ser Gly Lys Asp Gly
1               5                   10                  15

Asn Thr Ser Ala Ala Lys Ala Ala Ile Leu Lys Thr Asn Gly Thr Asn
            20                  25                  30

Asp Lys Gly Pro Val Val Ala Glu Ser Pro Lys Lys Pro
         35                  40                  45

<210> SEQ ID NO 223
<211> LENGTH: 35
<212> TYPE: PRT
<213> ORGANISM: Borrelia sp.

<400> SEQUENCE: 223

Met Thr Leu Phe Leu Phe Ile Ser Cys Asn Asn Ser Gly Lys Asp Gly
1               5                   10                  15

Asn Ser Ser Thr Ala Lys Arg Ala Ile Leu Lys Thr His Gly His Glu
            20                  25                  30

Asp Lys Gly
         35

<210> SEQ ID NO 224
<211> LENGTH: 36
<212> TYPE: PRT
<213> ORGANISM: Borrelia sp.

<400> SEQUENCE: 224

Asn Asn Ser Gly Lys Asp Gly Asn Ala Ser Ala Ala Lys Lys Ala Ile
1               5                   10                  15

Leu Lys Thr His Gly Asn Thr Asp Lys Gly Pro Val Val Ala Glu Ser
            20                  25                  30

Pro Lys Lys Pro
         35

<210> SEQ ID NO 225
<211> LENGTH: 35
<212> TYPE: PRT
<213> ORGANISM: Borrelia sp.

<400> SEQUENCE: 225

-continued

Met Thr Leu Phe Leu Phe Ile Ser Cys Asn Asn Ser Gly Lys Asp Gly
1               5                   10                  15

Asn Thr Ser Ala Ala Lys Lys Ala Ile Leu Lys Thr His Gly Asn Thr
            20                  25                  30

Asp Lys Gly
        35

<210> SEQ ID NO 226
<211> LENGTH: 45
<212> TYPE: PRT
<213> ORGANISM: Borrelia sp.

<400> SEQUENCE: 226

Met Thr Leu Phe Leu Phe Ile Ser Cys Asn Asn Ser Gly Lys Asp Gly
1               5                   10                  15

Asn Thr Ser Ala Ala Lys Lys Ala Ile Leu Lys Thr Asn Asn Asp Lys
            20                  25                  30

Thr Lys Gly Pro Val Val Ala Glu Ser Pro Lys Lys Pro
        35                  40                  45

<210> SEQ ID NO 227
<211> LENGTH: 34
<212> TYPE: PRT
<213> ORGANISM: Borrelia sp.

<400> SEQUENCE: 227

Thr Leu Phe Leu Phe Ile Ser Cys Asn Asn Ser Gly Lys Asp Gly Asn
1               5                   10                  15

Thr Ser Ala Ala Lys Lys Ala Ile Leu Lys Thr Asn Gln Ala Asn Asp
            20                  25                  30

Lys Gly

<210> SEQ ID NO 228
<211> LENGTH: 35
<212> TYPE: PRT
<213> ORGANISM: Borrelia sp.

<400> SEQUENCE: 228

Met Thr Leu Phe Leu Phe Ile Ser Cys Asn Asn Ser Gly Lys Asp Gly
1               5                   10                  15

Asn Thr Ser Ala Ala Lys Lys Ala Ile Leu Lys Thr Asn Gln Ala Asn
            20                  25                  30

Asp Lys Gly
        35

<210> SEQ ID NO 229
<211> LENGTH: 38
<212> TYPE: PRT
<213> ORGANISM: Borrelia sp.

<400> SEQUENCE: 229

Met Thr Leu Phe Leu Phe Ile Ser Cys Asn Asn Ser Gly Lys Asp Gly
1               5                   10                  15

Asn Thr Ser Ala Ala Lys Lys Ala Ile Leu Ile Thr Asp Ala Ala Lys
            20                  25                  30

Asp Lys Gly Pro Ile Val
        35

<210> SEQ ID NO 230
<211> LENGTH: 36

-continued

```
<212> TYPE: PRT
<213> ORGANISM: Borrelia sp.

<400> SEQUENCE: 230

Asn Asn Ser Gly Lys Asp Gly Asn Thr Ser Ala Ala Lys Lys Ala Ile
1               5                   10                  15

Leu Ile Thr Asp Ala Ala Lys Asp Lys Gly Pro Ile Val Ala Glu Ser
            20                  25                  30

Pro Lys Lys Pro
        35

<210> SEQ ID NO 231
<211> LENGTH: 45
<212> TYPE: PRT
<213> ORGANISM: Borrelia sp.

<400> SEQUENCE: 231

Met Thr Leu Phe Leu Phe Ile Ser Cys Asn Asn Ser Gly Lys Asp Gly
1               5                   10                  15

Asn Ala Ser Val Ala Lys Lys Ala Ile Leu Lys Thr His Asn Asp Ile
            20                  25                  30

Thr Lys Gly Pro Val Val Ala Glu Ser Pro Lys Lys Pro
        35                  40                  45

<210> SEQ ID NO 232
<211> LENGTH: 45
<212> TYPE: PRT
<213> ORGANISM: Borrelia sp.

<400> SEQUENCE: 232

Met Thr Leu Phe Leu Phe Ile Ser Cys Asn Asn Ser Gly Lys Asp Gly
1               5                   10                  15

Asn Thr Ser Ala Ala Lys Ala Ala Ile Leu Lys Thr Asn Gly Thr Lys
            20                  25                  30

Asp Lys Gly Pro Val Val Ala Glu Ser Pro Lys Lys Pro
        35                  40                  45

<210> SEQ ID NO 233
<211> LENGTH: 45
<212> TYPE: PRT
<213> ORGANISM: Borrelia sp.

<400> SEQUENCE: 233

Met Thr Leu Phe Leu Phe Ile Ser Cys Asn Asn Ser Gly Lys Asp Gly
1               5                   10                  15

Asn Thr Ser Ala Ala Lys Ala Ala Ile Leu Lys Thr Asn Gly Thr Lys
            20                  25                  30

Asp Lys Gly Pro Val Val Ala Glu Asn Pro Lys Lys Pro
        35                  40                  45

<210> SEQ ID NO 234
<211> LENGTH: 37
<212> TYPE: PRT
<213> ORGANISM: Borrelia sp.

<400> SEQUENCE: 234

Cys Asn Asn Ser Gly Lys Asp Gly Asn Ala Ser Thr Ala Lys Lys Ala
1               5                   10                  15

Ile Leu Arg Thr Asn Ala Ile Lys Asp Lys Gly Pro Val Val Ala Glu
            20                  25                  30
```

-continued

```
Thr Pro Lys Lys Pro
        35

<210> SEQ ID NO 235
<211> LENGTH: 42
<212> TYPE: PRT
<213> ORGANISM: Borrelia sp.

<400> SEQUENCE: 235

Met Thr Leu Phe Leu Phe Ile Ser Cys Asn Asn Ser Gly Lys Asp Gly
1               5                   10                  15

Asn Ala Ser Ala Ala Lys Asp Ala Ile Leu Lys Thr Asn Pro Thr Lys
            20                  25                  30

Thr Lys Gly Leu Leu Trp Pro Glu Ser Pro
        35                  40

<210> SEQ ID NO 236
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Thr, Ala, Asn, His, Asp or Ile

<400> SEQUENCE: 236

Met Thr Leu Phe Leu Phe Ile Ser Cys Asn Asn Ser Gly Lys Asp Gly
1               5                   10                  15

Asn Thr Ser Ala Ala Lys Lys Ala Ile Leu Lys Thr Asn Gly Xaa Lys
            20                  25                  30

Asp Lys Gly Pro Val Val Ala Glu Ser Pro Lys Lys Pro
        35                  40                  45

<210> SEQ ID NO 237
<211> LENGTH: 35
<212> TYPE: PRT
<213> ORGANISM: Borrelia burgdorferi

<400> SEQUENCE: 237

Tyr Gly Gln Asn Trp Thr Ser Pro Glu Asn Met Val Thr Ser Gly Pro
1               5                   10                  15

Phe Lys Leu Lys Glu Arg Ile Pro Asn Glu Lys Tyr Val Phe Glu Lys
            20                  25                  30

Asn Asn Lys
        35

<210> SEQ ID NO 238
<211> LENGTH: 35
<212> TYPE: PRT
<213> ORGANISM: Borrelia burgdorferi

<400> SEQUENCE: 238

Tyr Gly Gln Asn Trp Thr Ser Pro Glu Asn Met Val Thr Ser Gly Pro
1               5                   10                  15

Phe Lys Leu Lys Glu Arg Ile Pro Asn Glu Lys Tyr Val Phe Glu Lys
            20                  25                  30

Asn Asn Lys
        35
```

-continued

```
<210> SEQ ID NO 239
<211> LENGTH: 35
<212> TYPE: PRT
<213> ORGANISM: Borrelia burgdorferi

<400> SEQUENCE: 239

Tyr Gly Gln Arg Trp Thr Asp Pro Glu Asn Met Val Val Ser Gly Pro
1               5                   10                  15

Phe Lys Leu Lys Ser Arg Val Leu Asn Glu Lys Val Val Leu Glu Lys
            20                  25                  30

Asn Asn Lys
        35

<210> SEQ ID NO 240
<211> LENGTH: 35
<212> TYPE: PRT
<213> ORGANISM: Borrelia garinii

<400> SEQUENCE: 240

Tyr Gly Gln Ser Trp Thr Ser Pro Glu Asn Ile Val Thr Ser Gly Pro
1               5                   10                  15

Phe Lys Leu Lys Glu Arg Ile Pro Asn Glu Lys Tyr Val Val Glu Lys
            20                  25                  30

Asn Asp Lys
        35

<210> SEQ ID NO 241
<211> LENGTH: 35
<212> TYPE: PRT
<213> ORGANISM: Borrelia garinii

<400> SEQUENCE: 241

Tyr Gly Gln Ser Trp Thr Ser Pro Glu Asn Met Val Thr Ser Gly Pro
1               5                   10                  15

Phe Lys Leu Lys Glu Arg Ile Pro Asn Glu Lys Tyr Val Val Glu Lys
            20                  25                  30

Asn Asp Lys
        35

<210> SEQ ID NO 242
<211> LENGTH: 35
<212> TYPE: PRT
<213> ORGANISM: Borrelia garinii

<400> SEQUENCE: 242

Tyr Gly Gln Glu Trp Thr Asn Pro Glu Asn Met Val Val Ser Gly Pro
1               5                   10                  15

Phe Lys Leu Lys Ser Arg Val Leu Asn Glu Lys Val Val Leu Glu Lys
            20                  25                  30

Asn Asp Lys
        35

<210> SEQ ID NO 243
<211> LENGTH: 35
<212> TYPE: PRT
<213> ORGANISM: Borrelia afzelii

<400> SEQUENCE: 243

His Gly Gln Glu Trp Thr Asn Pro Glu Asn Met Val Val Ser Gly Pro
1               5                   10                  15

Phe Lys Leu Lys Ser Arg Val Leu Asn Glu Lys Ile Ile Leu Glu Lys
```

Asn Asn Lys
        35

<210> SEQ ID NO 244
<211> LENGTH: 35
<212> TYPE: PRT
<213> ORGANISM: Borrelia afzelii

<400> SEQUENCE: 244

Tyr Gly Glu Asn Trp Thr Asn Pro Glu Asn Ile Val Val Ser Gly Ala
1               5                   10                  15

Tyr Lys Leu Lys Glu Arg Ser Ile Asn Asp Lys Ile Val Ile Glu Lys
            20                  25                  30

Asn Glu Lys
        35

<210> SEQ ID NO 245
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Phe, Leu, Val or Ile

<400> SEQUENCE: 245

Tyr Gly Gln Asn Trp Thr Ser Pro Glu Asn Met Val Thr Ser Gly Pro
1               5                   10                  15

Phe Lys Leu Lys Glu Arg Ile Pro Asn Glu Lys Tyr Val Xaa Glu Lys
            20                  25                  30

Asn Asn Lys
        35

<210> SEQ ID NO 246
<211> LENGTH: 20
<212> TYPE: PRT
<213> ORGANISM: Borrelia burgdorferi

<400> SEQUENCE: 246

Lys Lys Ile Cys Glu Phe Ile Gln Asn Gln Trp Lys Lys Asn Leu Asn
1               5                   10                  15

Ile Asp Val Glu
        20

<210> SEQ ID NO 247
<211> LENGTH: 20
<212> TYPE: PRT
<213> ORGANISM: Borrelia burgdorferi

<400> SEQUENCE: 247

Arg Lys Ile Ala

```
<400> SEQUENCE: 248

Arg Lys Ile Ala Glu Phe Ile Gln Asn Gln Trp Lys Lys Asn Leu Asn
1               5                   10                  15

Ile Asn Val Gln
            20

<210> SEQ ID NO 249
<211> LENGTH: 20
<212> TYPE: PRT
<213> ORGANISM: Borrelia garinii

<400> SEQUENCE: 249

Lys Lys Ile Cys Glu Phe Ile Gln Asn Gln Trp Lys Lys Asn Leu Asn
1               5                   10                  15

Ile Asp Val Glu
            20

<210> SEQ ID NO 250
<211> LENGTH: 20
<212> TYPE: PRT
<213> ORGANISM: Borrelia garinii

<400> SEQUENCE: 250

Lys Lys Ile Cys Glu Phe Ile Gln Asn Gln Trp Lys Lys Ile Leu Asn
1               5                   10                  15

Ile Asp Val Glu
            20

<210> SEQ ID NO 251
<211> LENGTH: 20
<212> TYPE: PRT
<213> ORGANISM: Borrelia garinii

<400> SEQUENCE: 251

Arg Lys Ile Ala Glu Phe Ile Gln Asn Gln Trp Lys Lys Asn Leu Asn
1               5                   10                  15

Ile Asn Val Gln
            20

<210> SEQ ID NO 252
<211> LENGTH: 20
<212> TYPE: PRT
<213> ORGANISM: Borrelia afzelii

<400> SEQUENCE: 252

Lys Lys Ile Cys Glu Phe Ile Gln Asn Gln Trp Lys Lys Ile Leu Asn
1               5                   10                  15

Ile Asp Val Glu
            20

<210> SEQ ID NO 253
<211> LENGTH: 20
<212> TYPE: PRT
<213> ORGANISM: Borrelia afzelii

<400> SEQUENCE: 253

Arg Lys Ile Ala Glu Phe Ile Gln Asn Gln Trp Lys Lys Asn Leu Asn
1               5                   10                  15

Ile Asn Val Gln
            20
```

<210> SEQ ID NO 254
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 254

Lys Lys Ile Cys Glu Phe Ile Gln Asn Gln Trp Lys Lys Asn Leu Asn
1               5                   10                  15

Ile Asp Val Glu
            20

<210> SEQ ID NO 255
<211> LENGTH: 16
<212> TYPE: PRT
<213> ORGANISM: Borrelia sp.

<400> SEQUENCE: 255

Leu Ile Arg Phe Thr Thr Ile Ser Leu Gly Trp Asp Ser Asn Cys Asn
1               5                   10                  15

<210> SEQ ID NO 256
<211> LENGTH: 15
<212> TYPE: PRT
<213> ORGANISM: Borrelia sp.

<400> SEQUENCE: 256

Leu Ile Arg Phe Thr Thr Ile Ser Leu Gly Trp Asp Ser Asn Cys
1               5                   10                  15

<210> SEQ ID NO 257
<211> LENGTH: 35
<212> TYPE: PRT
<213> ORGANISM: Borrelia sp.

<400> SEQUENCE: 257

Tyr Gly Gln Asn Trp Thr Asn Pro Glu Asn Met Val Thr Ser Gly Pro
1               5                   10                  15

Phe Lys Leu Lys Glu Arg Ile Pro Asn Glu Lys Ile Val Phe Glu Lys
            20                  25                  30

Asn Asn Lys
        35

<210> SEQ ID NO 258
<211> LENGTH: 34
<212> TYPE: PRT
<213> ORGANISM: Borrelia sp.

<400> SEQUENCE: 258

Gly Gln Asn Trp Thr Ser Pro Glu Asn Met Val Thr Ser Gly Pro Phe
1               5                   10                  15

Lys Leu Lys Glu Arg Ile Pro Asn Glu Lys Tyr Val Phe Glu Lys Asn
            20                  25                  30

Asn Lys

<210> SEQ ID NO 259
<211> LENGTH: 15
<212> TYPE: PRT
<213> ORGANISM: Borrelia sp.

<400> SEQUENCE: 259

-continued

Ser Asp Tyr Tyr Ser Ser Ala Val Asn Ala Ile Tyr Phe Tyr Ser
1               5                   10                  15

<210> SEQ ID NO 260
<211> LENGTH: 35
<212> TYPE: PRT
<213> ORGANISM: Borrelia sp.

<400> SEQUENCE: 260

Tyr Gly Gln Asn Trp Thr Asn Pro Glu Asn Met Val Thr Ser Gly Pro
1               5                   10                  15

Phe Lys Leu Lys Glu Arg Ile Pro Asn Glu Lys Ile Val Phe Lys Glu
            20                  25                  30

Asn Asn Lys
        35

<210> SEQ ID NO 261
<211> LENGTH: 14
<212> TYPE: PRT
<213> ORGANISM: Borrelia sp.

<400> SEQUENCE: 261

Ile Tyr Phe Tyr Ser Phe Asn Thr His Ile Lys Pro Leu Asp
1               5                   10

<210> SEQ ID NO 262
<211> LENGTH: 24
<212> TYPE: PRT
<213> ORGANISM: Borrelia sp.

<400> SEQUENCE: 262

Ser Asp Tyr Tyr Ser Ser Ala Val Asn Ala Ile Tyr Phe Tyr Ser Phe
1               5                   10                  15

Asn Thr His Ile Lys Pro Leu Asp
            20

<210> SEQ ID NO 263
<211> LENGTH: 15
<212> TYPE: PRT
<213> ORGANISM: Borrelia burgdorferi

<400> SEQUENCE: 263

Asn Ser Gly Lys Asp Gly Asn Thr Ser Ala Asn Ser Ala Asp Glu
1               5                   10                  15

<210> SEQ ID NO 264
<211> LENGTH: 15
<212> TYPE: PRT
<213> ORGANISM: Borrelia burgdorferi

<400> SEQUENCE: 264

Gly Asn Thr Ser Ala Asn Ser Ala Asp Glu Ser Val Lys Gly Pro
1               5                   10                  15

<210> SEQ ID NO 265
<211> LENGTH: 15
<212> TYPE: PRT
<213> ORGANISM: Borrelia burgdorferi

<400> SEQUENCE: 265

Asn Ser Ala Asp Glu Ser Val Lys Gly Pro Asn Leu Thr Glu Ile
1               5                   10                  15

<210> SEQ ID NO 266
<211> LENGTH: 15
<212> TYPE: PRT
<213> ORGANISM: Borrelia burgdorferi

<400> SEQUENCE: 266

Ser Val Lys Gly Pro Asn Leu Thr Glu Ile Ser Lys Lys Ile Thr
1               5                   10                  15

<210> SEQ ID NO 267
<211> LENGTH: 15
<212> TYPE: PRT
<213> ORGANISM: Borrelia burgdorferi

<400> SEQUENCE: 267

Asn Leu Thr Glu Ile Ser Lys Lys Ile Thr Glu Ser Asn Ala Val
1               5                   10                  15

<210> SEQ ID NO 268
<211> LENGTH: 15
<212> TYPE: PRT
<213> ORGANISM: Borrelia burgdorferi

<400> SEQUENCE: 268

Ser Lys Lys Ile Thr Glu Ser Asn Ala Val Val Leu Ala Val Lys
1               5                   10                  15

<210> SEQ ID NO 269
<211> LENGTH: 15
<212> TYPE: PRT
<213> ORGANISM: Borrelia burgdorferi

<400> SEQUENCE: 269

Glu Ser Asn Ala Val Val Leu Ala Val Lys Glu Ile Glu Thr Leu
1               5                   10                  15

<210> SEQ ID NO 270
<211> LENGTH: 15
<212> TYPE: PRT
<213> ORGANISM: Borrelia burgdorferi

<400> SEQUENCE: 270

Val Leu Ala Val Lys Glu Ile Glu Thr Leu Leu Ala Ser Ile Asp
1               5                   10                  15

<210> SEQ ID NO 271
<211> LENGTH: 15
<212> TYPE: PRT
<213> ORGANISM: Borrelia burgdorferi

<400> SEQUENCE: 271

Glu Ile Glu Thr Leu Leu Ala Ser Ile Asp Glu Leu Ala Thr Lys
1               5                   10                  15

<210> SEQ ID NO 272
<211> LENGTH: 15
<212> TYPE: PRT
<213> ORGANISM: Borrelia burgdorferi

<400> SEQUENCE: 272

Leu Ala Ser Ile Asp Glu Leu Ala Thr Lys Ala Ile Gly Lys Lys
1               5                   10                  15

<210> SEQ ID NO 273

```
<211> LENGTH: 15
<212> TYPE: PRT
<213> ORGANISM: Borrelia burgdorferi

<400> SEQUENCE: 273

Glu Leu Ala Thr Lys Ala Ile Gly Lys Lys Ile Gln Gln Asn Gly
1               5                   10                  15

<210> SEQ ID NO 274
<211> LENGTH: 15
<212> TYPE: PRT
<213> ORGANISM: Borrelia burgdorferi

<400> SEQUENCE: 274

Ala Ile Gly Lys Lys Ile Gln Gln Asn Gly Gly Leu Ala Val Glu
1               5                   10                  15

<210> SEQ ID NO 275
<211> LENGTH: 15
<212> TYPE: PRT
<213> ORGANISM: Borrelia burgdorferi

<400> SEQUENCE: 275

Ile Gln Gln Asn Gly Gly Leu Ala Val Glu Ala Gly His Asn Gly
1               5                   10                  15

<210> SEQ ID NO 276
<211> LENGTH: 15
<212> TYPE: PRT
<213> ORGANISM: Borrelia burgdorferi

<400> SEQUENCE: 276

Gly Leu Ala Val Glu Ala Gly His Asn Gly Thr Leu Leu Ala Gly
1               5                   10                  15

<210> SEQ ID NO 277
<211> LENGTH: 15
<212> TYPE: PRT
<213> ORGANISM: Borrelia burgdorferi

<400> SEQUENCE: 277

Ala Gly His Asn Gly Thr Leu Leu Ala Gly Ala Tyr Thr Ile Ser
1               5                   10                  15

<210> SEQ ID NO 278
<211> LENGTH: 15
<212> TYPE: PRT
<213> ORGANISM: Borrelia burgdorferi

<400> SEQUENCE: 278

Ala Tyr Thr Ile Ser Lys Leu Ile Thr Gln Lys Leu Asp Gly Leu
1               5                   10                  15

<210> SEQ ID NO 279
<211> LENGTH: 15
<212> TYPE: PRT
<213> ORGANISM: Borrelia burgdorferi

<400> SEQUENCE: 279

Lys Leu Ile Thr Gln Lys Leu Asp Gly Leu Lys Asn Ser Glu Lys
1               5                   10                  15

<210> SEQ ID NO 280
<211> LENGTH: 15
<212> TYPE: PRT
```

<213> ORGANISM: Borrelia burgdorferi

<400> SEQUENCE: 280

Lys Leu Asp Gly Leu Lys Asn Ser Glu Lys Leu Lys Glu Lys Ile
1               5                   10                  15

<210> SEQ ID NO 281
<211> LENGTH: 15
<212> TYPE: PRT
<213> ORGANISM: Borrelia burgdorferi

<400> SEQUENCE: 281

Lys Asn Ser Glu Lys Leu Lys Glu Lys Ile Glu Asn Ala Lys Lys
1               5                   10                  15

<210> SEQ ID NO 282
<211> LENGTH: 15
<212> TYPE: PRT
<213> ORGANISM: Borrelia burgdorferi

<400> SEQUENCE: 282

Leu Lys Glu Lys Ile Glu Asn Ala Lys Lys Cys Ser Glu Asp Phe
1               5                   10                  15

<210> SEQ ID NO 283
<211> LENGTH: 15
<212> TYPE: PRT
<213> ORGANISM: Borrelia burgdorferi

<400> SEQUENCE: 283

Glu Asn Ala Lys Lys Cys Ser Glu Asp Phe Thr Lys Lys Leu Glu
1               5                   10                  15

<210> SEQ ID NO 284
<211> LENGTH: 15
<212> TYPE: PRT
<213> ORGANISM: Borrelia burgdorferi

<400> SEQUENCE: 284

Cys Ser Glu Asp Phe Thr Lys Lys Leu Glu Gly Glu His Ala Gln
1               5                   10                  15

<210> SEQ ID NO 285
<211> LENGTH: 15
<212> TYPE: PRT
<213> ORGANISM: Borrelia burgdorferi

<400> SEQUENCE: 285

Thr Lys Lys Leu Glu Gly Glu His Ala Gln Leu Gly Ile Glu Asn
1               5                   10                  15

<210> SEQ ID NO 286
<211> LENGTH: 15
<212> TYPE: PRT
<213> ORGANISM: Borrelia burgdorferi

<400> SEQUENCE: 286

Gly Glu His Ala Gln Leu Gly Ile Glu Asn Val Thr Asp Glu Asn
1               5                   10                  15

<210> SEQ ID NO 287
<211> LENGTH: 15
<212> TYPE: PRT
<213> ORGANISM: Borrelia burgdorferi -continued

```
<400> SEQUENCE: 287

Leu Gly Ile Glu Asn Val Thr Asp Glu Asn Ala Lys Lys Ala Ile
1               5                   10                  15

<210> SEQ ID NO 288
<211> LENGTH: 15
<212> TYPE: PRT
<213> ORGANISM: Borrelia burgdorferi

<400> SEQUENCE: 288

Val Thr Asp Glu Asn Ala Lys Lys Ala Ile Leu Ile Thr Asp Ala
1               5                   10                  15

<210> SEQ ID NO 289
<211> LENGTH: 15
<212> TYPE: PRT
<213> ORGANISM: Borrelia burgdorferi

<400> SEQUENCE: 289

Leu Ile Thr Asp Ala Ala Lys Asp Lys Gly Ala Ala Glu Leu Glu
1               5                   10                  15

<210> SEQ ID NO 290
<211> LENGTH: 15
<212> TYPE: PRT
<213> ORGANISM: Borrelia burgdorferi

<400> SEQUENCE: 290

Ala Lys Asp Lys Gly Ala Ala Glu Leu Glu Lys Leu Phe Lys Ala
1               5                   10                  15

<210> SEQ ID NO 291
<211> LENGTH: 15
<212> TYPE: PRT
<213> ORGANISM: Borrelia burgdorferi

<400> SEQUENCE: 291

Ala Ala Glu Leu Glu Lys Leu Phe Lys Ala Val Glu Asn Leu Ala
1               5                   10                  15

<210> SEQ ID NO 292
<211> LENGTH: 15
<212> TYPE: PRT
<213> ORGANISM: Borrelia burgdorferi

<400> SEQUENCE: 292

Lys Leu Phe Lys Ala Val Glu Asn Leu Ala Lys Ala Ala Lys Glu
1               5                   10                  15

<210> SEQ ID NO 293
<211> LENGTH: 15
<212> TYPE: PRT
<213> ORGANISM: Borrelia burgdorferi

<400> SEQUENCE: 293

Val Glu Asn Leu Ala Lys Ala Ala Lys Glu Met Leu Ala Asn Ser
1               5                   10                  15

<210> SEQ ID NO 294
<211> LENGTH: 15
<212> TYPE: PRT
<213> ORGANISM: Borrelia burgdorferi

<400> SEQUENCE: 294
```

```
Lys Ala Ala Lys Glu Met Leu Ala Asn Ser Val Lys Glu Leu Thr
1               5                   10                  15

<210> SEQ ID NO 295
<211> LENGTH: 15
<212> TYPE: PRT
<213> ORGANISM: Borrelia burgdorferi

<400> SEQUENCE: 295

Glu Met Leu Ala Asn Ser Val Lys Glu Leu Thr Ser Pro Ile Val
1               5                   10                  15
```

We claim:

1. A composition consisting essentially of two or more peptides, wherein the composition comprises at least one peptide from each of groups (a) and (b):
   (a) MKKNDQI(V or G)AAIALRGVA (SEQ ID NO:49), and
   (b) one or more specific peptides selected from the group consisting of:

DTGSERSIRYRRRVY; (SEQ ID NO: 24)

KIEFSKFTVKIKNKD; (SEQ ID NO: 25)

GFISCDLFIRYEMKE; (SEQ ID NO: 22)

INKLEAKKTSLKTYSEYEEQ; (SEQ ID NO: 27)

KEEFKIELVLKESSS; (SEQ ID NO: 17)

FEDAMKLGLALYLDY; (SEQ ID NO: 1)

YGQNWTSPENMVTSGPFKLKERIPNEKYVFEKNNK; (SEQ ID NO: 11)

VSRKGGLLPDIIIKI; (SEQ ID NO: 20)

NKTFNNLLKLTILVN; (SEQ ID NO: 41)

LIRFTTISLGWDSNN; (SEQ ID NO: 2)

MTLFLFISCNNSGKDGNTSA; (SEQ ID NO: 8)

KKICEFIQNQWKKNLNIDVE; (SEQ ID NO: 45)

NTLDVPPKTFVVKLALGYAE; (SEQ ID NO: 19)

IDDSIKKIDEELKNT; (SEQ ID NO: 28)

PFILEAKVRATTVAE; (SEQ ID NO: 44)

KKPMNKKGKGKIARKKGKSKVSRKEPYIHS; (SEQ ID NO: 23)

KFYSSLRLEVRKIEQ; (SEQ ID NO: 3)

TILVNLLISCGLTGA; (SEQ ID NO: 43)

NSRSRYNNFYKKEADFLGAA; (SEQ ID NO: 26)
and

IYFYAFNTHIKPLDN; (SEQ ID NO: 13)

or an active variant of the specific peptides of group (b), wherein the active variants of the peptides of group (b) are selected from the groups consisting of:
for SEQ ID NO:24:

DTSSERSIRYRRHVY, (SEQ ID NO: 178)

DTGTERSIRYRKRTY, (SEQ ID NO: 179)

DTGTERSIRFRRHTY, (SEQ ID NO: 180)

DTGTERSIKFRRHTY, (SEQ ID NO: 181)

DTGTERSKAYRKRAY, (SEQ ID NO: 182)

DTGTERSIRYRRRTY, (SEQ ID NO: 183)

---TERSIRYRKRTY, (SEQ ID NO: 184)

---TERSIRYRRHTY, (SEQ ID NO: 185)

---TERSIRFRRHTY, (SEQ ID NO: 186)

---SEKARKYRRNVY, (SEQ ID NO: 187)
and

---TERSKAYRKRAY; (SEQ ID NO: 188)

for SEQ ID NO:25:

KIKFSKFTVKIKNKD, (SEQ ID NO: 117)

KIEFSEFTVKIKYK-, (SEQ ID NO: 118)

-IKFSEFTVNIKNK-, (SEQ ID NO: 119)

and

```
                                     (SEQ ID NO: 120)
-IKFSEFTVKIKYK-;
``` for SEQ ID NO:22:

```
                                     (SEQ ID NO: 95)
GFISCDLFIRDEIKE,
and (SEQ ID NO: 96)
SFISCNLFTRDEIKE;
``` for SEQ ID NO:27:

```
                                     (SEQ ID NO: 155)
IEKLEAKKTSLKTYSEYEE-, (SEQ ID NO: 156)
IEKLDSKKTSLKTYSEYEE-, (SEQ ID NO: 157)
IEKLDSKKTSIETYSEYEE-, (SEQ ID NO: 158)
IDKSDAKKTSLKTYSEYE--, (SEQ ID NO: 159)
IEKSDPKSVSLKTYSDY---,
and (SEQ ID NO: 160)
--KIEIEKTELKTEYNEIED-;
``` for SEQ ID NO:17:

```
                                     (SEQ ID NO: 55)
KEEFKIELVLKESST, (SEQ ID NO: 56)
KAERKIELVLKE---, (SEQ ID NO: 57)
KEEFKFELVLKESST, (SEQ ID NO: 58)
KEEFEIELVLKESST, (SEQ ID NO: 59)
KAERKIELV(N)(L)LKE,
and (SEQ ID NO: 60)
-EIFKIEKVL----;
``` for SEQ ID NO:1:

```
                                     (SEQ ID NO: 190)
FEDAMKLGIALYLDY, (SEQ ID NO: 191)
FEDAMKIGIALYLDY,
and (SEQ ID NO: 192)
FEDAMKLGLTLYLDY;
``` for SEQ ID NO:11:

```
                                     (SEQ ID NO 257)
YGQNWTNPENMVTSGPFKLKERIPNEKIVFEKNNK,
```

```
                                     (SEQ ID NO 63)
YGENWTNPENIVVSGAYKLKERLINDKIVIENNEK, (SEQ ID NO 64)
YGQEWTNPENMVVSGPFKLKSRVLNEKVVLEKNDK, (SEQ ID NO 65)
YKGNWTNPENMVTSGPFKLKKRLPNEKIIFEKN--, (SEQ ID NO 66)
HGQNWTNPENMVVSGPFKLKSRVLNEKIILEKNNK, (SEQ ID NO 67)
YGQSWTNPENIVTSGPFKLKERIPNEKYVVEKNDK, (SEQ ID NO 68)
YKGNWTSPENMVTSGPFKLKKRLPNEKIIFEKNER, (SEQ ID NO 69)
YGQRWTDPENMVVSGPFKLKSRVLNEKVVLEKNNK, (SEQ ID NO 70)
HGQEWTNPENMVVSGPFKLKSRVLNEKIILEKNNK, (SEQ ID NO 71)
FGNKWTNPENMVTSGPFKLKRRILNEEISLEKNKK,
and (SEQ ID NO 72)
FGNKWTSSENMVTSGPFKLKRRILNEEISLEKNEK;
``` for SEQ ID NO:20:

```
                                     (SEQ ID NO: 123)
IGRKGGLLPDIIIKI, (SEQ ID NO: 124)
VGRKGGLLPDIIIKI, (SEQ ID NO: 125)
VSRKAGLLPDIIIKI, (SEQ ID NO: 126)
VFSNDNFLSELIIKI, (SEQ ID NO: 127)
VFSNDNFLSELIIKI,
and (SEQ ID NO: 128)
---KAGIFPDLII--;
``` for SEQ ID NO:41:

```
                                     (SEQ ID NO: 204)
NKAFGNLLKEGILVN, (SEQ ID NO: 205)
NKIYKDLLKIAILVN, (SEQ ID NO: 206)
NKTYKNLLKLTILVN,
and (SEQ ID NO: 207)
NKTFNNVIKLTILVN;
``` for SEQ ID NO:2:

```
                                     (SEQ ID NO: 194)
LFRFSAISIGS----, (SEQ ID NO: 195)
LFRFSAISIGSDSNN, (SEQ ID NO: 196)
```

-continued

LFRFSAI-SIG----S, (SEQ ID NO: 197)
LIRFSAISLGSDSNN,
and (SEQ ID NO: 198)
LIRFTAISIGWDSNN;

for SEQ ID NO:8:

(SEQ ID NO 75)
---FLFISCNNSGKDGNTSA, (SEQ ID NO 76)
-TLFLFISCNNSGGD----T, (SEQ ID NO 31)
MTLFLFISCNNSGKGGDSAS, (SEQ ID NO 77)
MTLFLFISCNNSGKDGNSAS, (SEQ ID NO 78)
-----FISCNNSGKDGNTSA, (SEQ ID NO 79)
---FLFISCNNSGKDGN---, (SEQ ID NO 80)
MTLFLFISCNNSGKD, (SEQ ID NO 81)
MTLFLFISCNNSGKGGDSA-, (SEQ ID NO 82)
MTLFLFISCNNSGKDGNSA-, (SEQ ID NO 83)
MTLLLFISSNTSGKDGNSSA,
and (SEQ ID NO 84)
MTLFLFISCNNSGKDGNASA;

for SEQ ID NO:45:

(SEQ ID NO: 141)
KKICEFIQNQWKKNLNINVE, (SEQ ID NO: 142)
KKICEFIQNQWKKILNIDVE, (SEQ ID NO: 143)
RKIAEFIQNQWKKNLNINVQ, (SEQ ID NO: 144)
KKIAAFIQNQWKKILNINL -, (SEQ ID NO: 145)
KEVASFIQSQWKKVLNIDVE, (SEQ ID NO: 146)
KKVATFIQNQWKKILNINI-, (SEQ ID NO: 147)
KGAEFLQEQFKKILNIKIE, (SEQ ID NO: 148)
KKIAEFIQNQWKKNLNIDVE, (SEQ ID NO: 149)
KKICEFIQNQWKKILNIDVE, (SEQ ID NO: 150)
KEIANFIQSQWKKVLNIDIE, (SEQ ID NO: 151)

-continued
KITAEFLQEQFKKVLNINVA,
and (SEQ ID NO: 152)
---AEFLQEQFKKILNINLE;

for SEQ ID NO:19:

(SEQ ID NO: 123)
IGRKGGLLPDIIIKI, (SEQ ID NO: 124)
VGRKGGLLPDIIIKI, (SEQ ID NO 131)
-TQDTPPKTFVIKLALGYAE, (SEQ ID NO: 132)
-TQDTPPKTFVIKLALGYA-,
and (SEQ ID NO: 133)
-TLEVSSKSIVVRL------;

for SEQ ID NO:28:

(SEQ ID NO: 163)
IDDSIKKIEEELKNT, (SEQ ID NO: 164)
IDDSLKKIEEELK--, (SEQ ID NO: 165)
IDENFKKIEEEFKDT, (SEQ ID NO: 166)
ITNSLKKIEEELKEA, (SEQ ID NO: 167)
IDENFKKIEEEFKD, (SEQ ID NO: 168)
IEDLIKKINEEILN-, (SEQ ID NO: 169)
INDSLKKIEEEL---, (SEQ ID NO: 170)
-DENFKKIEEEFKDT, (SEQ ID NO: 171)
-DENFKKIEEEFKD-, (SEQ ID NO: 172)
IDDALENINEELKK, (SEQ ID NO: 173)
IRESAKKIDESLK-, (SEQ ID NO: 174)
-EDLIKKINEEILN,
and (SEQ ID NO: 175)
--NVIKRIEEEAKN-;

for SEQ ID NO:44:

(SEQ ID NO: 209)
SFILEAKVRATTVAE, (SEQ ID NO: 210)
SFILEAKMRGTTVAE, (SEQ ID NO: 211)
PFILKAKMRGTEVTE,

-continued

```
                        (SEQ ID NO: 212)
-FIKQAKVRAIKVAE, (SEQ ID NO: 213)
-FILKAKIKAIQVAE,
and (SEQ ID NO: 214)
-FILKAKIQAIQVAE;
``` for SEQ ID NO:23:

```
                         (SEQ ID NO: 99)
KNSMNKKGKGKIARKKGKSKVSRKEPSIHS, (SEQ ID NO: 100)
KKSLNKKGKDKVARKKVEGNAVKKDPFNH-, (SEQ ID NO: 101)
KKPMNKKGKGKIARKNGKSKVSGKEPFIHS, (SEQ ID NO: 102)
KKPMNKKGKGKIARKKVKSKVSRKEPYIHS,
and (SEQ ID NO: 103)
KKPIN KQGKS KVSRK QGKSN VSRKE PSIHS;
``` for SEQ ID NO:3:

```
                         (SEQ ID NO: 87)
KFYASLRLEVRKIEQ, (SEQ ID NO: 88)
KFYASLRLEVRKVEQ, (SEQ ID NO: 89)
KFYSNRFLEIVKSE-, (SEQ ID NO: 90)
-IFSNLQNEAKKIEQ, (SEQ ID NO: 91)
KFYSSLRLEVRKVEQ, (SEQ ID NO: 92)
-FYSSLNYDENKI--,
and (SEQ ID NO: 93)
KFYISVKLEYK----;
``` for SEQ ID NO:43:

```
                         (SEQ ID NO 43)
TILVNLLISCGLTGA, (SEQ ID NO: 106)
TILVSLLISCGLTGA, (SEQ ID NO: 107)
TILVNLLVACGLTGA, (SEQ ID NO: 108)
TILVSLLVACGLTGA, (SEQ ID NO: 109)
---VSLLVACGLTG-, (SEQ ID NO: 110)
-ILVNLFLSCG----, (SEQ ID NO: 111)
TILVNLFLVS-----, (SEQ ID NO: 112)
TLIVGLLVACSLTG-, (SEQ ID NO: 113)
-ILVFFLISC-----, (SEQ ID NO: 114)
TVLI--LISCSL---,
and (SEQ ID NO: 115)
TLLVSLFIACSLTG-;
``` for SEQ ID NO:26:

```
                         (SEQ ID NO: 200)
NSRSRYDNFYKKEADFLGAA, (SEQ ID NO: 201)
NSRSRYNNYYKKEADFLGAA,
and (SEQ ID NO: 202)
NSRGRYNNSYKKEADFLIAA;
``` for SEQ ID NO:13:

```
                         (SEQ ID NO: 136)
IYFYAFNTTVKPLDN, (SEQ ID NO: 137)
IYFYAFNTKAKPLDN,
and (SEQ ID NO: 138)
IYLYSFNTKIKPLDD-,
``` wherein the specific peptides or active variants optionally have 1-3 additional or 1-3 fewer amino acids present on either or both the N-terminal or C-terminal ends of the peptide sequence, and wherein each peptide or active variant specifically binds to the same antibody to a pathogenic *Borrelia* as the specified peptide sequences listed above.

2. A composition consisting essentially of two or more peptides, wherein the composition comprises at least one peptide from each of groups (a) and (b):

(a) MKKNDQI(V or G)AAIALRGVA (SEQ ID NO:49), and (b) one or more specific peptides selected from the group consisting of:

```
                         (SEQ ID NO: 24)
DTGSERSIRYRRRVY, (SEQ ID NO: 25)
KIEFSKFTVKIKNKD, (SEQ ID NO: 22)
GFISCDLFIRYEMKE, (SEQ ID NO: 27)
INKLEAKKTSLKTYSEYEEQ, (SEQ ID NO: 17)
KEEFKIELVLKESSS, (SEQ ID NO: 1)
FEDAMKLGLALYLDY, (SEQ ID NO: 9)
AKKAILITDAAKDKG,
```

```
                                        (SEQ ID NO: 11)
YGQNWTSPENMVTSGPFKLKERIPNEKYVFEKNNK, (SEQ ID NO: 20)
VSRKGGLLPDIIIKI, (SEQ ID NO: 41)
NKTFNNLLKLTILVN, (SEQ ID NO: 2)
LIRFTTISLGWDSNN, (SEQ ID NO: 8)
MTLFLFISCNNSGKDGNTSA, (SEQ ID NO: 45)
KKICEFIQNQWKKNLNIDVE, (SEQ ID NO: 19)
NTLDVPPKTFVVKLALGYAE, (SEQ ID NO: 28)
IDDSIKKIDEELKNT, (SEQ ID NO: 44)
PFILEAKVRATTVAE, (SEQ ID NO: 23)
KKPMNKKGKGKIARKKGKSKVSRKEPYIHS, (SEQ ID NO: 3)
KFYSSLRLEVRKIEQ, (SEQ ID NO: 43)
TILVNLLISCGLTGA, (SEQ ID NO: 26)
NSRSRYNNFYKKEADFLGAA, (SEQ ID NO: 13)
IYFYAFNTHIKPLDN, (SEQ ID NO: 7)
KNEGLKEKIDAAKKCSETFT,
and (SEQ ID NO: 16)
LVACSIGLVERTNAA,
``` or active variants of said specific peptides of groups (a) and (b), wherein one or two of the amino acids of the specified peptide sequences are substituted with another amino acid, wherein the specific peptides or active variants optionally have 1-3 additional or 1-3 fewer amino acids present on either or both the N-terminal or C-terminal ends of the specific peptide or active variant sequence, and
wherein each peptide or active variant specifically binds to the same antibody to a pathogenic *Borrelia* as the specified peptide sequences listed above.

3. The composition of claim 2, wherein the additional amino acids are present on either the N-terminal or C-terminal ends of the specific peptide sequence, and wherein said additional amino acids correspond to the consecutive amino acids from a protein of a *Borrelia* strain comprising the specified peptide sequence.

4. The composition of claim 2, wherein the peptides (a) and (b) are not covalently linked.

5. The composition of claim 2, wherein the specific peptides or active variants further comprise an N-terminal cysteine residue, and/or have 1-3 additional or 1-3 fewer amino acids present on either the N-terminal or C-terminal ends of the specific peptide sequence.

6. The composition of claim 2, wherein peptide (b) is selected from the group consisting of:

```
                                        (SEQ ID NO: 24)
DTGSERSIRYRRRVY, (SEQ ID NO: 25)
KIEFSKFTVKIKNKD, (SEQ ID NO: 22)
GFISCDLFIRYEMKE, (SEQ ID NO: 27)
INKLEAKKTSLKTYSEYEEQ, (SEQ ID NO: 17)
KEEFKIELVLKESSS, (SEQ ID NO: 1)
FEDAMKLGLALYLDY, (SEQ ID NO: 9)
AKKAILITDAAKDKG, (SEQ ID NO: 11)
YGQNWTSPENMVTSGPFKLKERIPNEKYVFEKNNK, (SEQ ID NO: 20)
VSRKGGLLPDIIIKI,
and (SEQ ID NO: 41)
NKTFNNLLKLTILVN,
``` or is an active variant of said peptide.

7. The composition of claim 6, wherein peptide (b) consists of a peptide selected from the group consisting of:

```
                                        (SEQ ID NO: 24)
DTGSERSIRYRRRVY
and
                                        (SEQ ID NO: 25)
KIEFSKFTVKIKNKD,
``` or is an active variant of said peptide.

8. The composition of claim 7, wherein peptide (a) is MKKNDQI(V or G)AAIALRGVA (SEQ ID NO:49) or is an active variant thereof, and peptide (b) is DTGSERSIRYR-RRVY (SEQ ID NO:24), or is an active variant thereof.

9. The composition of claim 7, wherein peptide (a) is MKKNDQI(V or G)AAIALRGVA (SEQ ID NO:49) or is an active variant thereof, and peptide (b) is KIEFSKFT-VKIKNKD (SEQ ID NO:25), or is an active variant thereof.

10. The composition of claim 2, wherein peptide (b) consists of one of the peptides selected from the group consisting of:

```
                                        (SEQ ID NO: 24)
DTGSERSIRYRRRVY, (SEQ ID NO: 25)
KIEFSKFTVKIKNKD, (SEQ ID NO: 22)
GFISCDLFIRYEMKE, (SEQ ID NO: 27)
INKLEAKKTSLKTYSEYEEQ, (SEQ ID NO: 17)
KEEFKIELVLKESSS, (SEQ ID NO: 1)
FEDAMKLGLALYLDY,
```

-continued

AKKAILITTDAAKDKG, (SEQ ID NO: 9)

YGQNWTSPENMVTSGPFKLKERIPNEKYVFEKNNK, (SEQ ID NO: 11)

VSRKGGLLPDIIIKI, (SEQ ID NO: 20)
and

NKTFNNLLKLTILVN. (SEQ ID NO: 41)

11. The composition of claim 10, wherein peptide (b) consists of a peptide selected from the group consisting of:

DTGSERSIRYRRRVY (SEQ ID NO: 24)
and

KIEFSKFTVKIKNKD. (SEQ ID NO: 25)

12. The composition of claim 11, wherein peptide (a) is MKKNDQI(V or G)AAIALRGVA (SEQ ID NO:49) or is an active variant thereof, and peptide (b) is DTGSERSIRYR-RRVY (SEQ ID NO:24) and/or KIEFSKFTVKIKNKD (SEQ ID NO:25).

13. The composition of claim 2, wherein the peptides (a) and (b) are covalently linked by a spacer comprising 1-5 uncharged aliphatic amino acids.

14. The composition of claim 13, wherein the spacer comprises glycine and/or alanine amino acids.

15. The compositions of claim 14, wherein the spacer consists of three glycines.

16. A diagnostic assay for detecting an antibody that specifically binds to a pathogenic *Borrelia* protein in a biological sample from a subject, comprising the composition of claim 2 and reagents for detecting the complex formed when one or more of the peptides of said composition binds to said antibody.

17. The diagnostic assay of claim 16, wherein the specific peptides or active variants further comprise an N-terminal cysteine residue, and/or have 1-3 additional or 1-3 fewer amino acids present on either the N-terminal or C-terminal ends of the specific peptide sequence.

18. A kit for diagnosing Lyme borreliosis in a biological sample from a subject, comprising in at least two separate containers,
  i. the composition of claim 2,
  ii. reagents for detecting the complex formed when one or more of the peptides of said composition binds to an antibody in a biological sample from said subject, and
  iii. a substrate for immobilizing the peptides.

19. The kit of claim 18, further comprising a control antibody that specifically binds to a pathogenic *Borrelia* protein.

20. The kit of claim 18, wherein the specific peptides or active variants further comprise an N-terminal cysteine residue, and/or have 1-3 additional or 1-3 fewer amino acids present on either the N-terminal or C-terminal ends of the specific peptide sequence.

21. A method for diagnosing Lyme disease in a subject, comprising contacting a biological sample from a subject suspected of having antibodies against a causative agent of Lyme disease with the composition of claim 2, under conditions effective for the formation of a peptide-antibody complex, and detecting the presence of the peptide-antibody complex.

22. The method of claim 21, wherein the specific peptides or active variants further comprise an N-terminal cysteine residue, and/or have 1-3 additional or 1-3 fewer amino acids present on either the N-terminal or C-terminal ends of the specific peptide sequence.

23. The method of claim 21, wherein the peptide-antibody complex is detected by adding a binding partner which is specific for the peptide or for the antibody, wherein the binding partner is directly labeled or is labeled with a signal generating reagent.

24. The method of claim 23, wherein the binding partner is an antibody attached to an enzyme, and a signal is generated when the enzyme reacts with a suitable substrate.

25. The method of claim 23, wherein the detecting is performed with an ELISA assay.

26. The method of claim 23, wherein the detecting is performed with a Luminex bead based assay.

27. The method of claim 23, wherein the subject is a cat or a dog.

28. The method of claim 23, wherein the subject is a human.

29. The composition of claim 2, wherein the composition comprises at least one peptide from each of groups (a) and (b):
  (a) MKKNDQI(V or G)AAIALRGVA (SEQ ID NO:49), and
  (b) one or more specific peptides selected from the group consisting of:
    DTGSERSIRYRRRVY (SEQ ID NO:24), or an active variant thereof wherein one or more of amino acids G3, S4, R6, I8, R9, Y10, R12, R13, and/or V14 can be substituted with an amino acid replacement, or one or more of amino acids G3, S4, E5, R6, S7, I8, R9, Y10, R12, R13, V14 can be substituted;
    KIEFSKFTVKIKNKD (SEQ ID NO:25), or an active variant thereof wherein one or more of amino acids E3, K6, K10 and/or N13 can be substituted with an amino acid replacement, or one or more of amino acids I2, E3, S5, K6, T8, V9, K10, N13, and/or K14 is substituted;
    GFISCDLFIRYEMKE (SEQ ID NO:22), or an active variant thereof wherein one or more of amino acids S4, and/or I13 can be substituted with an amino acid replacement, or one or more of amino acids G1, D6, I9, Y11, M13 can be substituted;
    INKLEAKKTSLKTYSEYEEQ (SEQ ID NO:27), or an active variant thereof wherein one or more of amino acids N2, L4, E5, A6, K7, L11, K12, and/or E19 can be substituted with an amino acid replacement, or one or more of amino acids N2, L4, E5, A6, K7, K8, T9, S10, L11, K12, S15, E16, and/or E19 can be substituted;
    KEEFKIELVLKESSS (SEQ ID NO:17), or an active variant thereof wherein one or more of amino acids E2, F4, K5, I6, and/or S15 can be substituted with an amino acid replacement; or amino acids E2, E3, F4, K5, I6, L8, and/or S15 can be substituted;
    FEDAMKLGLALYLDY (SEQ ID NO:1), or an active variant thereof wherein one or more of amino acids A4, L7, L9, and/or A10 can be substituted with an amino acid replacement;
    YGQNWTSPENMVTSGPFKLKERIP-NEKYVFEKNNK (SEQ ID NO:11), or an active variant thereof wherein one or more of amino acids Y1, G2, Q3, N4, S7, M11, T13, P16, F17, E21, I23, P24, E26, Y28, V29, F30, and/or N34 can be substituted with an amino acid replacement;

VSRKGGLLPDIIIKI (SEQ ID NO:20), or an active variant thereof wherein one or more of amino acids V1, S2, R3, K4, G5, G6, L7, L8, P9, D10, I11 can be substituted with an amino acid replacement;

NKTFNNLLKLTILVN (SEQ ID NO:41), or an active variant thereof wherein one or more of amino acids T3, F4, N5, L7, L8, and/or T11 can be substituted with an amino acid replacement;

LIRFTTISLGWDSNN (SEQ ID NO:2), or an active variant thereof wherein one or more of amino acids A4, L7, L9, and/or A10 can be substituted with an amino acid replacement;

MTLFLFISCNNSGKDGNTSA (SEQ ID NO:8), or an active variant thereof wherein one or more of amino acids K14, G15, N17, T18, S19, and/or A20 can be substituted with an amino acid replacement, or one or more of amino acids F4, C9, N11, D15, G16, N17, T18, S19, and/or A20 can be substituted;

KKICEFIQNQWKKNLNIDVE (SEQ ID NO:45), or an active variant thereof wherein one or more of amino acids K1, K2, I3, C4, E5, I7, N9, W11, N14, D18, V19, E20 can be substituted with an amino acid replacement, or one or more amino acids K1, K2, I3, C4, E5, I7, Q8, N9, W11, K12, K13, N14, D18, V19, E20 is substituted;

NTLDVPPKTFVVKLALGYAE (SEQ ID NO:19), or an active variant thereof wherein one or more of amino acids L3, D4, V5, P6, P7, T9, F10, V12, K13 can be substituted with an amino acid replacement, or one or more of amino acids L3, D4, V5, P6, P7, K8, T9, V12, K13 can be substituted;

IDDSIKKIDEELKNT (SEQ ID NO:28), or an active variant thereof wherein one or more of amino acids D2, D3, S4, I5, D9, E11, L12, K13, N14, and/or T15 can be substituted with an amino acid replacement, or one or more of amino acids D2, D3, S4, I5, K6, K7, I8, D9, E10, E11, L12, K13, N14, and/or T15 can be substituted;

PFILEAKVRATTVAE (SEQ ID NO:44), or an active variant thereof wherein one or more of amino acids P1, L4, E5, A6, V8, R9, A10, T11, T12 can be substituted with an amino acid replacement;

KKPMNKKGKGKIARKKGKSKVSRKEPYIHS (SEQ ID NO:23), or an active variant thereof wherein one or more of amino acids P3, M4, G8, G10, I12, K16, G17, K18, S19, K20, V21, S22, R23, E25, Y27, and/or I28 can be substituted with an amino acid replacement; or one or more of amino acids K2, P3, M4, N5, K6, K7, G8, G10, K11, I12, A13, R14, K16, G17, K18, S19, K20, V21, S22, R23, K24, E25, Y27, I28, H29 can be substituted;

KFYSSLRLEVRKIEQ (SEQ ID NO:3), or an active variant thereof wherein one or more of amino acids S4, and/or I13 can be substituted with an amino acid replacement, or one or more of amino acids K1, F2, Y3, S4, S5, L6, R7, L8, E9, V10, R11, and/or I13 can be substituted;

TILVNLLISCGLTGA (SEQ ID NO:43), or an active variant thereof wherein one or more of amino acids N5, I8, and/or S9 can be substituted with an amino acid replacement; or one or more of amino acids I2, V4, N5, L6, L7, I8, S9, G11, and/or T13 can be substituted;

NSRSRYNNFYKKEADFLGAA (SEQ ID NO:26), or an active variant thereof wherein one or more of amino acids S4, N7, F9, G18 can be substituted with an amino acid replacement; and IYFYAFNTHIKPLDN (SEQ ID NO:13), or an active variant thereof wherein one or more of amino acids Y2, F3, Y4, A5, F6, T8, H9, I10, and/or N15 can be substituted with an amino acid replacement, or one or more of amino acids Y2, F3, Y4, A5, F6, T8, H9, I10, D14 can be substituted;

wherein the specific peptides or active variants optionally have 1-3 additional or 1-3 fewer amino acids present on either or both the N-terminal or C-terminal ends of the specific peptide or active variant sequence, and wherein each peptide or active variant specifically binds to the same antibody to a pathogenic *Borrelia* as the specified peptide sequences listed above.

30. The composition of claim 29, wherein the consensus sequence for the peptides of group (b) and active variants thereof are selected from the groups consisting of:

for SEQ ID NO:24:
D T (G or S) (S or T) E (R or K) S (I, K, or R) (R, K, or A) (Y or F) R (R or K) (R, H, or C) (V, T, I, or A) Y (SEQ ID NO: 176) and
D T (G or S) (S or T) (E or D) (R or K) (S or A) (I, K, or R) (R, K, or A) (Y or F) R (R or K) (R, H, C, or N) (V, T, I, or A) Y (SEQ ID NO: 177);

for SEQ ID NO:25:
K I (E or K) F S (K or E) F T V (K or N) I K (N or Y) K D (SEQ ID NO: 116);

for SEQ ID NO:22:
(G or S) F I S C (D or N) L F (I or T) R (Y or D) E (M or I) K E (SEQ ID NO: 94);

for SEQ ID NO:27:
I (N, E, or D) K (L, S, or I) (E or D) (A, S, E, or I) (K or E) K T S (L or I) (K or E) T Y S E Y E (E or D) Q (SEQ ID NO: 153), and
I (N, E, or D) K (L, S, or I) (E or D) (A, S, E, or I) (K or E) (K, N, or S) (T or X) (S or X) (L, F, or I) (K, E, G, or T) T Y (S, N, or G) (E, D, or S) Y E (E or D) Q (where X is any amino acid) (SEQ ID NO: 154);

for SEQ ID NO:17:
K (E or A) E (F or R) (K or E) (I or F) E L V L K E S S (S or T) (SEQ ID NO 54);

for SEQ ID NO:1:
F E D (A or V) M K (L or I) G (L or I) (A or T) L Y L D Y (SEQ ID NO: 189);

for SEQ ID NO:11:
(Y, H, or F) (G or K) (Q, G, E, or N) (N, K, S, R, or E) W T (S, N, or D) P E N (M or I) V (T or V) S G (P or A) (F or Y) K L K (E, K, S or R) R (I, S, L, or V) (P, L, or I) N (E or D) K (Y, V or I) (V or I) (F, V, L or I) E K N (N, D, or E) K (SEQ ID NO 61), and
Y1, G2, Q3, N4, S7, P8, M11, T13, P16, F17, E21, I23, P24, E26, K27, Y28, V29, F30, N34, and/or K35 (SEQ ID NO 62);

for SEQ ID NO:20:
(V or I) (S, or G) R K G G L L P D I I I K I (SEQ ID NO: 121), and
(V or I) (S, G, or F) (R or S) (K, D, or N) (G, A, or D) (G, N, or E) (L, I, or F) (L or F) (P, S, or A) (D or E) (I or L) I I K I (SEQ ID NO: 122);

for SEQ ID NO:41:
N K (T, E, or A) (F or Y) (N, K, or G) N (L, V, or I) (L or I) K L (T or G) I L V N (SEQ ID NO: 203);

for SEQ ID NO:2:
L (I or F) R F (T or S) (T or A) I S (L or I) G (W or S) D S N N (SEQ ID NO: 193);

for SEQ ID NO:8:
  M T L F L F I S C N N S G (K or G) (D or G) G (N or D) (T, A, or S) (S, A, or T) (A or S) (SEQ ID NO 73), and
  M T L (F, L, or Y) L F I S (C or S) N (N or T) S G K (D or G) (G, V, or A) (N, D, T or S) (T, A, or S) (S, A, or T) (A or T) (SEQ ID NO 74);

for SEQ ID NO:45:
  (K or R) (K or E) (I, V, or G) (C, A, or Y) (E, A, S, N, or T) F (I or L) Q (N, S, or E) Q (W or F) K K (N, I, or V) L N I (D or N) (V, I, or L) (E or Q) (SEQ ID NO: 139), and
  (K or R) (K or E) (I, V, or G) (C, A, or Y) (E, A, S, N, or D) F (I or L) (Q or E) (N, S, or E) Q (W, E, F, or K) (K, N, or I) (K or N) (N, I, or V) L N I (D or N) (V, I, or L) (E, A, or Q) (SEQ ID NO: 140);

for SEQ ID NO:19:
  N T (L or Q) (D or E) (V or T) (P or S) (P or S) K (T or S) (F or I) V (V or I) (K or R) L A L G Y A E (SEQ ID NO: 129), and
  N T (L or Q) (D or E) (V or T) (P or S) (P or S) (K or R) (T or D) F V (V or I) (K or R) L A L G Y A E (SEQ ID NO: 130);

for SEQ ID NO:28:
  I (D, E, R, N, or T) (D, E, or N) (S or X) (I, L, F, or A) K K I (D, E, or N) E (E or S) (L, F, or I) (K or L) (N, K, S, D, or E) (T, S, or A) (where X is any amino acid) (SEQ ID NO: 161), and
  I (D, E, G, N, or T) (D, E, or N) (S or X) (I, L, F, V, or A) (K or E) (K or N) (I or L) (D, E, or N) (E or D) (E, A, or S) (L, F, I, or A) (K or N) (N, K, S, D, E, or G) (T, S, V, or A) (where X is any amino acid) (SEQ ID NO: 162);

for SEQ ID NO:44:
  (P or S) F I (L or K) (E, K, or Q) (A or S) K (V, M, or I) (R, K, or Q) (A or G) (T or I) (T, E, A, D, K, Q) V A E (SEQ ID NO: 208);

for SEQ ID NO:23:
  K K (P or S) (M, I, or L) N K K (G or D) K (G or D) K (I or V) A R K (K or N) (G or V) (K or E) (S or G) (K or N) (V or A) (S or V) (R, G, or K) K (E or D) P (Y, S, or F) (I or N) H S (SEQ ID NO: 97), and
  K (K or N) (P, S, or D) (M, I, or L) (N, S, D, or T) (K or N) (K, Q, or E) (G, S, or D) K (G, S, or D) (K, E, or S) (I or V) (A, S or V) (R or K) K (K, Q, N, or L) (G, R, or V) (K, D, E, or N) (S, N, G, A, D, or W) (K, N, I, D, or R) (V, A, or E) (S, V, T, or F) (R, G, or K) (K or Q) (E or D) P (Y, S, or F) (I, N, T, or V) (H, N, or T) S (SEQ ID NO: 98);

for SEQ ID NO:3:
  K F Y (S or A) S L R L E V R K (I or V) E Q (SEQ ID NO 85), and
  (K or I) (F, I, or L) (Y, F, or D) (S or A) (S or N) (L or R) (R, F, N, or Q) (L, N or Y) (E or D) (V, A, I, or E) (R, V, I, K, or N) K (I, S, or V) E Q (SEQ ID NO 86);

for SEQ ID NO:43:
  T I L V (N or S) L L (I or V) (S or A) C G L T G A (SEQ ID NO: 104), and
  T (I, L, or V) L (V, I, or L) (N or S) (L or F) (L or F) (I or V) (S or A) C (G or S) L (T or K) G A (SEQ ID NO: 105);

for SEQ ID NO:26:
  N S R (S or G) R Y (N or D) N (F, S, or Y) Y K K E A D F L (G or I) A A (SEQ ID NO: 199); and for SEQ ID NO:13:
  I (Y or G) (F, L, or Y) (Y, or I) (A or S) (F or L) N (T or M) (H, T, K, or N) (I or V) K P L D (N or D) (SEQ ID NO: 134), and
  I (Y or G) (F, L, or Y) (Y, F, I, or L) (A, R, K or S) (F or L) N (T or M) (H, T, K, or N) (I, V, or A) K P L (D or N) N (SEQ ID NO: 135).

31. A diagnostic assay for detecting an antibody that specifically binds to a pathogenic *Borrelia* protein in a biological sample from a subject, comprising the composition of claim 29 and reagents for detecting the complex formed when one or more of the peptides of said composition binds to said antibody.

32. The diagnostic assay of claim 31, wherein the specific peptides or active variants further comprise an N-terminal cysteine residue, and/or have 1-3 additional or 1-3 fewer amino acids present on either the N-terminal or C-terminal ends of the specific peptide sequence.

33. A kit for diagnosing Lyme borreliosis in a biological sample from a subject, comprising in at least two separate containers,
  i. a composition of claim 29,
  ii. reagents for detecting the complex formed when one or more of the peptides of said composition binds to an antibody in a biological sample from said subject.

34. The kit of claim 33, wherein the specific peptides or active variants further comprise an N-terminal cysteine residue, and/or have 1-3 additional or 1-3 fewer amino acids present on either the N-terminal or C-terminal ends of the specific peptide sequence.

35. The kit of claim 33, further comprising a control antibody that specifically binds to a pathogenic *Borrelia* protein.

36. A method for diagnosing Lyme disease in a subject, comprising contacting a biological sample from a subject suspected of having antibodies against a causative agent of Lyme disease with a composition of claim 29, under conditions effective for the formation of a peptide-antibody complex, and detecting the presence of the peptide-antibody complex.

37. The method of claim 36, wherein the specific peptides or active variants further comprise an N-terminal cysteine residue, and/or have 1-3 additional or 1-3 fewer amino acids present on either the N-terminal or C-terminal ends of the specific peptide sequence.

38. The method of claim 36, wherein the peptide-antibody complex is detected by adding a binding partner which is specific for the peptide or for the antibody, wherein the binding partner is directly labeled or is labeled with a signal generating reagent.

39. The method of claim 38, wherein the binding partner is an antibody attached to an enzyme, and a signal is generated when the enzyme reacts with a suitable substrate.

40. The method of claim 38, wherein the detecting is performed with an ELISA assay.

41. The method of claim 38, wherein the detecting is performed with a Luminex bead based assay.

42. The method of claim 38, wherein the subject is a cat or a dog.

43. The method of claim 38, wherein the subject is a human.

* * * * *